United States Patent [19]

Carroll

[11] Patent Number: 5,904,922
[45] Date of Patent: *May 18, 1999

[54] TREATMENT WITH POLYVALENT ANTIVENOM CONTAINING IMMUNOGLOBULIN WHICH IS GREATER THAN 50% VENOM-REACTIVE

[75] Inventor: Sean B. Carroll, Cottage Grove, Wis.

[73] Assignee: Ophidian Pharmaceuticals, Inc., Madison, Wis.

[*] Notice: This patent is subject to a terminal disclaimer.

[21] Appl. No.: 08/442,000

[22] Filed: May 16, 1995

Related U.S. Application Data

[62] Division of application No. 08/275,304, Jul. 14, 1994, Pat. No. 5,443,976, which is a continuation of application No. 07/983,668, Dec. 1, 1992, abandoned, which is a division of application No. 07/429,791, Oct. 31, 1989, Pat. No. 5,196,193.

[51] Int. Cl.⁶ .................. A61K 39/395; A61K 38/55; C07K 16/18; C07K 17/02
[52] U.S. Cl. ............................. 424/130.1; 424/158.1; 424/542; 435/174; 435/178; 435/180; 436/518; 436/529; 436/824; 514/2; 514/21; 530/387.1; 530/389.1; 530/413; 530/810; 530/813; 530/856; 530/858
[58] Field of Search ................................ 530/387.1, 856, 530/858, 389.1, 413, 810, 813; 424/130.1, 542, 158.1; 514/2, 21; 435/174, 178, 180; 436/518, 529, 824

[56] References Cited

U.S. PATENT DOCUMENTS

| | | | |
|---|---|---|---|
| 3,836,433 | 9/1974 | Wirth et al. | 195/68 |
| 4,550,019 | 10/1985 | Polson | 424/85 |
| 5,196,193 | 3/1993 | Carroll | 424/85.8 |
| 5,340,923 | 8/1994 | Carroll | 530/389.1 |

OTHER PUBLICATIONS

Criley, B.R., Venoms, Buckley & Porges, eds., Am. Assoc. Advan. Sci., Washington, D.C. 1956, pp. 373–380.
Parrish, et al., Clinical Toxicology, 3(3), Sep. 1970, pp. 501–511.
Wingert and Wainschel, S. Med. J. 68:1015 (1975).
Christopher and Rodning, S. Med. J. 79:159 (1986).
Ellenhorn and Barceloux, In: *Medical Toxicology* (Elsevier Press) (1988) Ch. 39, pp. 1112–1132.
Parrish, Public Health Rpt. 81:269 (1966).
Russell et al., JAMA 233:341 (1975).
Ayeb and Delori, In: *Handbook of Natural Toxins*, vol. 2., Insect Poisons, Allergens, and Other Invertebrate Venoms (Anthony T. Tu, Ed.) (Marcel Dekker) (1984) Ch. 18, pp. 607–638.
Hassan, In: *Handbook of Natural Toxins*, vol. 2., Insect Poisons, Allergens, and Other Invertebrate Venoms (Anthony T. Tu, Ed.) (Marcel Dekker) (1984) Ch. 17, pp. 577–605.
Lumley et al., Med. J. Aust. 148:527 (1988).
Endean, Toxicon 25:483 (1987).
Olson et al., Toxicon 22:733 (1984).
Baxter and Marr, Toxicon 7:195 (1969).
Habermehl, In: *Venomous Animals and Their Toxins*, (Springer–Verlag, Berlin) (1981).
MacDonald et al., Am. J. Epidemiology 124:794 (1986).
Tacket et al., Am J. Med. 76:794 (1984).
Thorne and Gorbach, In: *International Encylcopedia of Pharmacology and Therapeutics,* Pharmacology of Bacterial Toxins (Dorner and Drews, Eds.) (Pergamon Press, Oxford) (1986), pp. 5–16.
Russell, JAMA, 215:1994 (1971).
Audibert et al., Proc. Natl. Acad. Sci. USA 79:5042 (1982).
Alouf, Ann. Inst. Pasteur/Microbiol. 136B:309 (1985).
New et al., New Eng. J. Med. 311:56 (1984).
Freitas et al., Toxicon 27:341 (1989).
Perez et al., Toxicon 22:967 (1984).
Iddon et al., Toxicon 26:167 (1988).
Martinez et al., Toxicon 27:239 (1989).
Russell et al., Toxicon 8:63 (1970).
Curry et al., J. Toxicol. Clin. Toxicol. 21:417 (1983–1984).
World Health Organization Publication No. 58, Geneva (1981).
Sutherland, Med. J. Aust. 1:613 (1977).
Christensen, In: *Snake Venoms,* (Springer–Verlag, Berlin) (1979) Ch. 20, pp. 825–846.
Parrish and Hayes, Clin. Tox. 3:501 (1970).
Yang et al., Toxicon 15:51 (1977).
Kukongviriyapan et al., J. Immunol. Meth. 49:97 (1982).
Karlsson et al., Eur. J. Biochem. 21:1 (1971).
Lomonte et al., Toxicon 23:807 (1985).

(List continued on next page.)

*Primary Examiner*—David M. Naff
*Attorney, Agent, or Firm*—Medlen & Carroll, LLP

[57] ABSTRACT

Antivenoms to snake, spider, scorpion and jelly fish venoms are produced for treatment of humans and animals, and for analytical use. Polyvalent antivenoms are produced containing immunoglobulin which is greater than fifty percent venom reactive. Purified polyvalent antivenom is derived from a first polyvalent antivenom having two or more monovalent subpopulations, and purified such that greater than fifty percent of the monovalent subpopulations are recovered by weight. The antivenoms can be horse or avian such as chicken antivenom. Chicken antivenom is obtained using a whole venom that is not glutaraldehyde pretreated, and the antivenom contains yolk immunoglobulin. Antivenoms are purified with an antigen matrix containing a single whole venom or a plurality of whole venoms covalently attached to an insoluble support such as aldehyde-activated agarose. Preferably, the whole venoms forming the plurality of whole venoms are selected from the four whole venoms of *C. atrox*, *B. atrox*, *C. adamanteus* and *C. durissus terrificus*. A combination of immobilized *C. atrox* and *C. durissus terrificus* whole venoms can substantially purify antivenom reactive with all four venoms. The antivenoms are intravenously injected to treat an envenomed mammalian subject.

12 Claims, 16 Drawing Sheets

OTHER PUBLICATIONS

Sullivan et al., J. Vet Hum. Toxicol. 24:192 (Suppl.) (1982).

Sullivan and Russell, Proc. West. Pharmacol. Soc. 25:185 (1982).

Sullivan and Russell, Toxicon Suppl. 3:429 (1983).

Jeter et al., Toxicon 21:729 (1983).

Bar–Or et al., Clin. Tox. 22:1 (1984).

Russell et al., Am J. Trop. Med. Hyg. 34:141 (1985).

Sullivan, Ann. Emerg. Med. 16:938 (1987).

Johnstone and Thorpe, In: *Immunochemistry in Practice*, 2nd Edition (Blackwell Scientific Publications 1987) p. 209.

Polson et al., Immunol. Comm. 9:495 (1980).

Benson et al., J. Immunol. 87:616 (1961).

Benedict and Yamaga, In: *Comparative Immunology*, Immunoglobulins and Antibody Production in Avian Species (J.J. Marchaloni, Ed.) (Blackwell, Oxford) (1966) Ch. 13, pp. 335–375.

Patterson et al., J. Immunol. 89:272 (1962).

Carroll and Stollar, J. Biol. Chem. 258:24 (1983).

Philpot, Jr., et al., Toxicon 16:603 (1978).

Towbin et al., Proc. Nat. Acad. Sci. USA 76:4350 (1979).

Weber and Osborn, In: *The Proteins*, 3rd Edition (H. Neurath and R.L. Hill, Eds.) (Academic Press, NY) (1975) pp. 179–223.

Carroll and Laughon, In: *DNA Cloning: A Practical Approach*, vol. III (D. Glover, Ed.) (IRL Press, Oxford) (1987) pp. 89–111.

Theakston, In: *Natural Toxins. Animal, Plant and Microbial* (J.B. Harris, Ed.) (Clarenden Press, Oxford) (1986) pp. 287–303.

Ohsaka, In: *Snake Venoms,* Handbook of Experimental Pharmacology, vol. 52 (C.Y. Lee, Ed.) (Springer–Verlag, Berlin) (1979) pp. 480–546.

Martin et al., J. Biol. Chem. 262:4452 (1987).

Kabat, In: *Structural Concepts in Immunology and Immunochemistry* (Holt, Rhinehart, and Winston, NY) (1968) pp. 35–40.

Ownby et al., Toxicon 21:849 (1983).

B.S. Thalley and S.B. Carroll, Bio/Technology 8:934 (1990).

Mebs et al., Toxicon 26:453 (1988).

dos Santos et al., Toxicon 27:297 (1989).

Sterogene Biochemicals, Brochure, "Actisep ™ Immunoaffinity Purification System".

Coulter et al., Med. J. Aust. 1:433 (1980).

Ho et al., Am. J. Trop. Med. Hyg. 35:579 (1986).

Ho et al., Toxicon 24:211 (1986).

Theakston and Reid, Toxicon 17:511 (1979).

Theakston, Toxicon 21:341 (1983).

Chandler and Hurrell, Clinica Chemica Acta 121:225 (1982).

Minton et al., Clin. Toxicol. 22:303 (1984).

Minton, Ann. Emerg. Med. 16:932 (1987).

Weinstein et al., Toxicon 23:825 (1985).

Schaeffer et al., Toxicon 26:67 (1988).

FIG. 11A — *C. durissus terrificus* - SPECIFIC MONOVALENT SUBPOPULATION
- ● ON *C. durissus terrificus*
- ▲ ON *C. atrox*
- × NON - IMMUNE HORSE IgG

FIG. 11B — *C. atrox*- SPECIFIC MONOVALENT SUBPOPULATION
- ● ON *C. durissus terrificus*
- ▲ ON *C. atrox*
- × NON - IMMUNE HORSE IgG

FIG. 11C — *C. atrox* / *C. durissus terrificus* - SPECIFIC POLYVALENT SUBPOPULATION
- ● ON *C. durissus terrificus*
- ▲ ON *C. atrox*
- × NON - IMMUNE HORSE IgG

TREATMENT WITH POLYVALENT ANTIVENOM CONTAINING IMMUNOGLOBULIN WHICH IS GREATER THAN 50% VENOM-REACTIVE

This application is a division of application Ser. No. 08/275,304, filed Jul. 14, 1994, now U.S. Pat. No. 5,443, 976, which is a continuation of application Ser. No. 07/983, 668, filed Dec. 1, 1992, abandoned, which is a division of application Ser. No. 07/429,791, filed Oct. 31, 1989, U.S. Pat. No. 5,196,193.

BACKGROUND OF THE INVENTION

The present invention relates to antivenoms suitable for treatment of humans and animals as well as for analytical use.

I. Venoms

A toxin is a single protein or peptide that has deleterious effects in man or animals. A venom comprises a plurality of toxins; they are relatively complex mixtures of proteins and peptides that can cause considerable morbidity and mortality in humans and animals.

The chemical actions of and biological reactions to venoms are as diverse as their sources. Depending on the nature of the venoms, their toxic effects may be evident in the cardiovascular, hematologic, nervous, and/or respiratory systems.

Each region of the world has its own particularly troublesome venomous species. Within Eukarvota (see Table 1), some specific venom sources from the Animalia kingdom are most notable.

A. Eukaryota.

i) Chordata. A number of Chordata classes are sources of venoms (e.g. Amphibians, Fish, Reptiles). Among Reptiles, the most significant order is snakes. Snake venom is a relatively complex mixture of enzymes, non-enzymatic proteins and peptides, and as yet unidentified compounds. W. A. Wingert and J. Wainschel, S. Med. J. 68:1015 (1975). D. C. Christopher and C. B. Rodning, S. Med. J. 79:159

TABLE 1

Phylogeny of Toxin- and Venom-Producing Organisms

SUPERKINGDOM: PROKARYOTA
KINGDOM: MONERA
DIVISION: BACTERIA
SUPERKINGDOM: EUKARYOTA
KINGDOM: FUNGI
KINGDOM: PLANTAE
KINGDOM: ANIMALIA
PHYLUM: CHORDATA
CLASSES:

Amphibia
Reptilia
Pisces
PHYLUM: ARTHROPODA
CLASSES:

Arachnida
Insecta
Myriapoda
PHYLUM: COELENTERATA
PHYLUM: MOLLUSCA (1986). While there are some chemical similarities, the venom of each species exhibits its own characteristic toxicity. M. J. Ellenhorn and D. G. Barceloux, Medical Toxicology, Ch. 39 (Elsevier Press 1988).

Of the over 100 species of snakes in the United States, approximately 10% are poisonous. H. M. Parrish, Public Health Rpt. 81:269 (1966). The majority of these are from the family Crotalidae. The venomous species include the rattlesnakes (Crotalus), cottonmouths and copperheads (Aqkistrodon), and pigmy and massassauga rattlesnakes (Sistrurus). There are also poisonous members of the Elapidae family, the coral snakes (Micruroides). F. E. Russell et al., JAMA 233:341 (1975).

ii) Arthropoda. In the Arthropoda phylum, an important class is Arachnida. Among Arachnida, scorpions (Order Scorpiones) produce the most significant venoms. While scorpion venoms are also complex mixtures, there has been some success identifying their active agents. Approximately thirty different protein neurotoxins, each having a molecular weight of about 7000 daltons, have been isolated. M. E. Ayeb and P. Delori, In: Handbook of Natural Toxins, Vol. 2, Insect Poisons, Allergens, and Other Invertebrate Venoms, (Anthony T. Tu, Ed.) (Marcel Dekker 1984), Chapter 18 (pp. 607–638). Of the approximately 650 scorpion species, the most dangerous belong to the Buthidae family and the genuses Tityus (North and South America), Centruroides (U.S. and Mexico), Centrurus (Mexico), Androctonus (Mediterranean/North Africa), Buthacus (Mediterranean/North Africa), Leiurus (Mediterranean/ North Africa), Buthotus (Mediterranean/North Africa), Buthus (Mediterranean/North Africa), and Parabuthus (South Africa). F. Hassan, In: Handbook of Natural Toxins, Vol. 2, Insect Poisons, Allergens, and Other Invertebrate Venoms, (Anthony T. Tu, Ed.) (Marcel Dekker 1984), Chapter 17 (pp. 577–605).

iii) Coelenterata. In the Coelenterata phylum, jelly fish are an important venomous species; the venom from *Chironex fleckeri* is among the most potent and medically significant. In the waters off Northern Australia, about one fatality occurs each year. J. Lumley et al., Med. J. Aust. 148, 527 (1988). Several toxic fractions have been characterized from *C. fleckeri* venom including two high molecular weight myotoxins (R. Endean, Toxicon 25, 483 (1987)) and several low molecular weight toxins having hemolytic or dermonecrotic properties (C. E. Olson et al., Toxicon 22, 733 (1984); E. H. Baxter and A. G. M. Marr, Toxicon 7, 195 (1969)).

iv) Mollusca. In the Mollusca phylum, the most significant venomous members are the coneshells (Conidae) which produce potent myotoxins that can be fatal. G. G. Habermehl, Venomous Animals and Their Toxins (Springer-Verlag, Berlin 1981). Little is known about the structure of the molluscan myotoxins.

B. ProkarYota.

Prokaryotes are an important source of toxins. Most bacterial toxins, for example, are well known. Among species of bacteria, the most notorious toxin sources are certainly *Clostridum botulinum* and *Clostridium parabotulinum*. The species produce the neurogenic toxin known as botulinus toxin. While a relatively rare occurrence in the United States, involving only 355 cases between 1976 and 1984 (K. L. MacDonald et al., Am J. Epidemiology 124, 794 (1986)), the death rate due to the botulism toxin is 12% and can be higher in particular risk groups. C. O. Tacket et al., Am. J. Med. 76, 794 (1984).

Many other bacteria produce protein toxins of significance to humans, including *Bacillus anthracis, Bordetella pertussis* (diptheria), *Pasteurella pestis, Pseudomonas aeruginosa, Streptococcos pyrogenes, Bacillus cereus, E.*

*coli, Shigella, Staphylococcus aureus, Vibrio cholerae,* and *Clostridium tetani.* Thorne and Gorbach, Pharmacology of Bacterial Toxins, In: International Encyclopedia of Pharmacology and Therapeutics, F. Dorner and J. Drews (eds.), Pergamon Press, Oxford (1986), pp. 5–16.

II. Treatment

As noted above, a toxin is defined as a single protein or peptide and a venom is defined as comprising a plurality of toxins. Both toxin and venom have been used as antigen for treatment.

Exposure to most venoms in humans does not result in protective immunity. Furthermore, all attempts to create protective immunity against venoms with vaccines have failed. F. E. Russell, JAMA 215:1994 (1971) (rattlesnake venom). By contrast, there has been success creating protective immunity against individual toxins, including diptheria (F. Audibert et al., Proc. Natl. Acad. Sci USA 79:5042 (1982)) and tetanus vaccines. J. E. Alouf, Ann Inst. Pasteur/Microbiol. 136B, 309 (1985).

A. Active Immunization

Tetanus toxoid injections provide an effective protection because they elicit a low level of circulating antibody and establish immunological memory. When exposed to a low dose of the tetanus organism and toxin, the immunized animal can neutralize the organism and toxin before the infection develops.

In the case of animal venoms, such prophylactic measures have not been feasible. First, many animal venoms are too difficult or too expensive to obtain to immunize a population where a relatively small percentage of that population will be exposed to the animal venom. Second, even if they can be obtained, animal venoms, unless detoxified, may cause more morbidity when administered to a large population than would be caused by the venomous animals themselves. Third, even if the venom is affordable, obtained in sufficient quantity, and detoxified, it is extremely difficult to achieve the titer of circulating antibody necessary to neutralize the infusion of what can be a large amount of venom (up to one gram of animal venom as compared with nanogram or picogram amounts of tetanus toxin)Finally, even with successful immunization, immunological memory is too slow to respond to the immediate crisis of envenomation.

Although active immunization with venoms has the above-named problems, some investigators have chosen to pursue research in this area rather than in the area of passive immunization, arguing that passive immunization is too long and expensive. These investigators have made some progress in the method of immunization by using liposomes. R. R. C. New et al., New Eng. J. Med. 311 56 (1984). T. V. Freitas et al., Toxicon 27:341 (1989).

B. Passive Immunization

Because the problems with active immunization have not been overcome, the only treatment available for venoms is passive immunization. Passive immunization, like active immunization, relies on antibodies binding to antigens. For our purposes here, antitoxin refers to antibody raised against a single toxin. Antivenom refers to antibody raised against whole venom.

In the case of passive immunization, the antibody used to bind the venom (antigen) is not made in the animal afflicted with the venom. Generally, an immune response is generated in a first animal. The serum of the first animal is then administered to the afflicted animal (the "host") to supply a source of specific and reactive antibody. The administered antibody functions to some extent as though it were endogenous antibody, binding the venom toxins and reducing their toxicity. (It is not known whether the antibody directly blocks the action of venom toxins or merely carries venom toxins out of the blood stream.)

i. Raising Antivenoms.

The first step in treatment by passive immunization involves raising an antibody with reactivity that is specific for the venom. Such an antibody is referred to as an antivenom. As noted above, venoms pose unique problems for immunization. They are often expensive and available in only small amounts. Furthermore, because they are toxic, they can do great damage before, and in some cases without, generating an immune response.

Usually the problem of a toxicity is approached by modifying the venom in some manner. Modification of venoms, however, creates new problems. On the one hand, the modification may have so damaged the venom that it is largely non-immunogenic. On the other hand, while not rendered non-immunogenic, the modification may have so altered the venom that a new antigenicity is created. That is, antibody raised to the modified venom is directed to the modification as part of the antigenic site. In this case, the antibody raised to the modified venom may not react with the unmodified venom (as it will be found in its natural state). Finally, the modification may itself be toxic or cause unexpected side effects.

Immunization with venoms is also complicated by their complex composition. Venoms are remarkably heterogeneous. Furthermore, the various components of venoms are present in different amounts. There is some concern that immunization with whole venom will not result in antibody reactive with all venom components.

ii. Administration. The second step in treatment by passive immunization (assuming, of course, the problems with the first step have been dealt with), involves the administering of antivenom to the host. The first concern is whether the host will tolerate the administration of "foreign" antibody In other words, will the host's immune system recognize the administered antibody as antigen and mount an adverse response?

Adverse host responses are typically of two types, immediate and delayed. Immediate reactions are also of two types: 1) anaphylaxis, and 2) Arthus reaction. Anaphylaxis is IgE mediated and requires sensitization to antigen. The Arthus reaction is complement dependent and requires only antibody-antigen complexes. Both immediate types of reactions are referred to as hypersensitivity reactions; the host responds as if primed by a first exposure. Such immediate reactions can be acute. Indeed, anaphylaxis, if untreated, can lead to respiratory failure and death.

Delayed reactions are caused by a host primary immune response to the foreign proteins of the antivenom. The reaction, called "serum sickness," is characterized by fever, enlarged lymph glands, and joint pain. These symptoms are apparent a number of days after passive immunization and gradually subside.

The next concern about administering antivenoms is the dose. Without knowing the amount of venom in the host it is difficult to know the amount of antivenom needed to treat the host. Furthermore, even if the amount of venom can be estimated, how is the amount of antivenom to be measured? Some approaches measure antivenom in units of volume. Such an approach does not account for different antivenom antibody concentrations within the same volume of serum.

iii Commercial Antivenoms. Antivenoms have been raised in a number of mammals. See J. C. Perez et al., Toxicon 22:967 (1984) (mice). D. Iddon et al., Toxicon 26:167 (1988) (mice). R. A. Martinez et al., Toxicon 27:239 (1989) (mice). M. E. Ayeb and P. Delori, In: Handbook of Natural Toxins, Vol. 2, Insect Poisons, Allergens, and Other Invertebrate Venoms, (Anthony T. Tu, Ed.) (Marcel Dekker 1984), Chapter 18 (pp. 607–638) (rabbits). F. E. Russell et al., Toxicon 8:63 (1970) (goats). S. C. Curry et al., J. Toxicol.—Clin. Toxicol. 21417 (1983–1984) (goats). F. Hassan, In: Handbook of Natural Toxins, Vol. 2, Insect Poisons, Allergens, and Other Invertebrate Venoms, (Anthony T. Tu, Ed.) (Marcel Dekker 1984), Chapter 17 (pp. 577–605) (cows). Horses, however, are the animal of choice by an overwhelming number of investigators and commercial antivenom producers. World Health Organization Publication No. 58 (Geneva 1981).

Horses are sturdy and tolerant to the antibody-raising process. Most importantly, they yield large volumes of blood (as much as ten liters per bleeding for large animals).

There are significant disadvantages, however, when using horses for antivenom production. First, for large production of antivenoms, horses more than 5 years old and usually less than 8 years old are required. Second, because new horses are easily killed or injured, production should be under veterinary care and supervision. Third, tetanus is known to be a common disease among horses; animals must be immunized as soon as they are introduced to the farm. F. Hassan, In: Handbook of Natural Toxins, Vol. 2, Insect Poisons, Allergens, and Other Invertebrate Venoms, (Anthony T. Tu, Ed.) (Marcel Dekker 1984), Chapter 17 (pp. 577–605). Fourth, large amounts of venom (antigen) are required for immunization in order to generate a satisfactory immune response in horses. Fifth, horse antibody binds and activates human and other mammalian complement pathways, leading (at the very least) to complement depletion and (at worst) to a more acute reaction by the host. Most commercial antivenoms contain anticomplementary activity. S. K. Sutherland, Med J. Australia 1: 613 (1977). Sixth, some humans are hypersensitive to horse serum proteins and may react acutely to even very small amounts of horse protein. P. A. Christensen, In: Snake Venoms (Springer-Verlag 1979), Chapter 20 (pp. 825–846).

In spite of these problems, horse antivenom is the only specific treatment of most venom poisonings known at the present time. It is considered vital for treating severe cases of snake envenomation. H. M. Parrish and R. H. Hayes, Clin. Tox. 3:501 (1970). Similarly, horse serum containing antivenoms is considered life-saving in the treatment of scorpion stings. F. Hassan, In: Handbook of Natural Toxins, Vol. 2, Insect Poisons, Allergens, and Other Invertebrate Venoms, (Anthony T. Tu, Ed.) (Marcel Dekker 1984), Chapter 17 (pp. 577–605).

In the United States, the primary commercial producer of antivenom to snake venoms is Wyeth Laboratories (Marietta, Pa.). To make a useful antivenom to members of the Crotalidae family, horses are immunized with a mixture of venom from four distinct species. To reduce their toxicity, the venoms are modified by treatment with formalin. To prolong their absorption, the modified venoms are mixed with aluminum hydroxide gel. H. M. Parrish and R. H. Hayes, Clin. Tox. 3:501 (1970). Serum is collected and total antibody is precipitated. During the collection process, it is reported that the ammonium sulfate precipitation destroys up to one half of the neutralizing antibodies of the crude antivenom. M. J. Ellenhorn and D. G. Barceloux, Medical Toxicology, Ch. 39 (Elsevier Press 1988).

One of the most difficult aspects of clinical management of envenomation is the lack of standardization of antivenoms. The recommended dosages of therapeutic horse-derived antivenoms is usually given in units of volume. For example, treatment with the Wyeth antivenom is measured in terms of vials of antivenom; each vial represents approximately 10 mls of antivenom in solution. D. C. Christopher and C. B. Rodning, S. Med. J. 79:159 (1986). M. J. Ellenhorn and D. G. Barceloux, Medical Toxicology, Ch. 39 (Elsevier Press 1988). H. M. Parrish and R. H. Hayes, Clin. Tox. 3:501 (1970). F. E. Russell et al., JAMA 233:341 (1975).

The potency of individual lots of antivenoms will vary because of two principal factors. First, because whole antisera or immunoglobulin fractions are used and the specific antibody titer per unit volume will vary from animal to animal and from day to day, the amount of venom-reactive antibodies will differ from preparation to preparation. Second, refinement procedures such as ammonium sulfate precipitation and pepsin digestion can reduce the yield of active antibody, causing variations in the titer of active ingredient per unit volume. These difficulties are exacerbated when antivenom is raised against a set of venoms in order to treat a range of species. That is, when certain species are more diverged from the immunizing group, it is more difficult to determine how much antivenom will be required.

Because of the array of common and serious side effects of unpurified antivenoms the physician must exercise caution not to give excessive amounts of horse product. Patients who receive seven or more vials of the Wyeth preparation are reported to invariably develop serum sickness; approximately 80% of patients overall who receive the preparation develop serum sickness within three weeks. M. J. Ellenhorn and D. G. Barceloux, Medical Toxicology, Ch. 39 (Elsevier Press 1988).

iv. Avoiding Side Effects. Because the commercial antivenoms presently available can cause their own adverse reactions, the risk of possible death or serious injury from the venom must be weighed against the risk of a hypersensitivity reaction to horse serum. Before administration of horse serum, good medical practice requires that serum sensitivity tests be performed. H. M. Parrish and R. H. Hayes, Clin. Tox. 3:501 (1970).

Serum sensitivity is typically performed by subcutaneously injecting a small amount of diluted serum in the arm of the patient. A salt solution is injected in the other arm as a control. Normally, a positive hypersensitivity test is indicated by no more than formation of a welt on the skin surface with surrounding swelling. Some patients, however, develop anaphylactic shock, i.e. a full hypersensitivity reaction. It is recommended in the medical literature that adrenalin be available for these cases.

While sensitivity testing has its advantages, it is generally acknowledged that it has no predictive value for serum sickness and reactions due to complement activation. World Health Organization Publication No. 58 (Geneva 1981). Thus, all patients must be regarded as potential "reactors" and all drugs and equipment required for dealing with reactions must be available before antivenoms are administered.

V. Purification.

One approach to avoiding side effects deserves special note. It has been theorized that the high incidence of side effects with current commercial horse antivenoms is due to the bulk of irrelevant protein in these preparations. (Protein other than specific antibody is considered to be irrelevant protein.) Under this theory, the removal of irrelevant protein would reduce the burden of foreign protein and, thereby, reduce the incidence of adverse immune responses.

F. Hassan, In: Handbook of Natural Toxins, Vol. 2, Insect Poisons, Allergens, and Other Invertebrate Venoms, (Anthony T. Tu, Ed.) (Marcel Dekker 1984), Chapter 17 (pp. 577–605) attempted a crude purification of horse antivenom. First, the horse serum was subjected to a mild pepsin digestion followed by ammonium sulfate precipitation. Then, the precipitate was heat denatured; the heat-labile fraction was removed. Unfortunately, approximately one-third of the initial antivenom activity was reported to be lost by this method.

A handful of antivenom investigators have considered immunoaffinity purification. However, most studies have only examined antibodies to a single toxin. C. C. Yang et al., Toxicon 15, 51 (1977) attempted immunoaffinity purification of antibody to a toxin in a snake venom. These investigators used cobrotoxin, a neurotoxic crystalline protein isolated from the venom of Taiwan cobra (*Naja naja atra*); whole venom was not used. Cobratoxin attached to Sepharose (CNBr-activated Sepharose 4B) was used as an antigen matrix and formic acid was used to elute the toxin-specific antibodies. The immunoaffinity purified antibody was reported to have a greater toxin-neutralizing capability than the unpurified antiserum.

V. Kukongviriyapan et al., J. Immunol. Meth. 49:97 (1982) followed with a similar purification scheme. Again, whole venom was not used. These investigators used *Naja naja siamensis* toxin 3, purified according to the method of E. Karlsson et al., Eur. J. Biochem. 21, 1 (1971). A number of antigen matrices were studied, including toxin-Sepharose (CNBr-activated Sepharose 4B), toxin-succinylaminoethyl Sepharose, toxin-albumin Sepharose, and toxin-succinylaminoethyl Biogel. Horse antibody was used. Unfortunately, only approximately 5% of the applied protein was reportedly bound and the destruction of antigenic sites on the immobilized toxin occurred extensively. Most importantly, the toxin-neutralizing capacity recovered in the purified antibody represented only approximately one-third that of the unpurified globulin.

M. E. Ayeb and P. Delori, In: Handbook of Natural Toxins, Vol. 2, Insect Poisons, Allergens, and Other Invertebrate Venoms, (Anthony T. Tu, Ed.) (Marcel Dekker 1984), Chapter 18 (pp. 607–638) also followed the Yang et al. procedure and applied it to purifying antibodies against individual scorpion neurotoxins. Again, whole venom was not used. These investigators used toxin II of *A. australis Hector*. While these investigators did not report yields, they noted that formic acid caused denaturation of the antibody.

B. Lomonte et al., Toxicon 23:807 (1985), purified antibodies against *B. Asper* myotoxin coupled to CNBr-activated Sepharose 4B. The anti-myotoxin was only 0.5–1.0% of the antivenom protein and was found to be less effective than crude antivenom in neutralizing the lethal effects of the venom.

J. B. Sullivan's research group examined immunoaffinity purification with whole venoms. See J. B. Sullivan et al., J. Vet. Hum. Toxicol. 24:192 (Suppl.) (1982). J. B. Sullivan and F. E. Russell, Proc. Western Pharmacol. Soc. 25:185 (1982). J. B. Sullivan and F. E. Russell, Toxicon Suppl. 3:429 (1983). W. S. Jeter et al., Toxicon 21:729 (1983). D. Bar-Or et al., Clin. Tox. 22:1 (1984). F. E. Russell et al., Am. J. Trop. Med. Hyg. 34:141 (1985). J. B. Sullivan, Ann. Emerg. Med. 16:938 (1987). All of this work was performed with a polyacrylamide resin and trapping as the means for associating the venom with the resin.

Trapping involves suspending molecules in a gel. Trapping does not involve attachment (covalent or non-covalent) of the venom via a reactive group on the resin; without such an attachment, venom can find its way through the matrix and end up in the eluate. Furthermore, as venom from the antigen matrix finds its way out of the suspension, there is a progressive reduction in the antibody binding capacity of the antigen matrix. Loss of binding capacity renders the matrix non-recyclable, i.e. one cannot recover the same amount of purified antibody in subsequent purifications.

Polyacrylamide has several drawbacks. First, polyacrylamide has low porosity and, hence, can sterically hinder some antibody-antigen interactions, thereby reducing the antibody binding capacity of the polyacrylamide-antigen matrix. A. Johnstone and R. Thorpe, Immunochemistry in Practice, 2d Edition (Blackwell Scientific Publications 1987), p. 209. Second, polyacrylamide itself is a neurotoxin; there is a concern that polyacrylamide may leech from the polyacrylamide-antigen matrix into the eluate and contaminate purified antibody.

vi. Non-mammalian Sources of Antivenoms. As mentioned above, most antivenoms are made in mammals and the overwhelming majority have been made in horses. There have been only a few attempts made at raising antivenoms in non-mammals. A. Polson et al., Immunol. Comm. 9:495 (1980), attempted to raise antivenoms against snake venoms in chickens. Their work was unsuccessful; the chicken immunoglobulin showed no protective activity against the venom in an assay performed in mice. It was speculated that chicken antibody interactions with venom are inherently weaker and less stable than those of horse antibody.

SUMMARY OF THE INVENTION

The present invention relates to antivenoms suitable for treatment of humans and animals as well as for analytical use.

In one embodiment, the present invention contemplates a composition comprising polyvalent antivenom, comprised of immunoglobulin of which greater than fifty percent is venom-reactive, and having two or more monovalent subpopulations. The composition is preferably in an aqueous solution in therapeutic amounts and intravenously injectable. The polyvalent antivenom preferably has reactivity to *C. atrox, B. atrox, C. adamanteus* and *C. durissus terrificus* venom. Preferably, one of the monovalent subpopulations comprises antibody with reactivity to *C. durissus terrificus* venom. The polyvalent antivenom preferably comprises horse antibody.

In another embodiment, the present invention contemplates a composition comprising polyvalent antivenom, comprised of immunoglobulin of which greater than fifty percent is venom-reactive, and having two or more monovalent subpopulations, wherein the polyvalent antivenom is derived from a first polyvalent antivenom comprised of immunoglobulin of which less than fifty percent is venom-reactive, and has substantially the same spectrum of reactivity as said first polyvalent antivenom.

In still another embodiment, the present invention contemplates a composition comprising, polyvalent antivenom, derived from a first polyvalent antivenom comprised of immunoglobulin of which less than fifty percent is venom-reactive, and having substantially the same spectrum of reactivity as the first polyvalent antivenom. The composition is preferably in an aqueous solution in therapeutic amounts and intravenously injectable. The polyvalent antivenom preferably has reactivity to *C. atrox, B. atrox, C. adamanteus* and *C. durissus terrificus* venom. The polyvalent antivenom preferably comprises horse antibody. The composition preferrably comprises polyvalent antivenom comprising two or more monovalent subpopulations.

In a preferred embodiment, the present invention contemplates a composition comprising venom-neutralizing avian antivenom. The composition is preferably in an aqueous solution in therapeutic amounts and intravenously injectable. Preferrably, the avian antivenom is chicken antivenom and the chicken antivenom is comprised of yolk immunoglobulin. It is desirable that the avian antivenom is comprised of protein comprised of greater than 90% immunoglobulin and greater than 50% venom-reactive immunoglobulin. Preferably, the avian antivenom is comprised of protein comprised of greater than 90% immunoglobulin and greater than 99% venom-reactive immunoglobulin. It is desirable that the avian antivenom is polyvalent. Preferably, the avian antivenom is high avidity chicken antivenom.

The present invention also contemplates an antigen matrix useful for purification of antivenom. In one embodiment, the antigen matrix comprises *C. durissus terrificus* venom attached to an insoluble support. In one embodiment, the antigen matrix comprises a plurality of venoms attached to an insoluble support. Preferably, the attachment is covalent attachment. It is desirable that the insoluble support prior to attachment to the plurality of venoms comprise a resin having aldehyde groups. Preferably, the plurality of venoms comprises *C. atrox, B. atrox, C. adamanteus* and *C. durissus terrificus* venom.

The present invention also contemplates a method for immobilizing whole venom. In one embodiment, the method comprises a) providing an insoluble support; b) providing two or more whole venoms; and c) attaching two or more whole venoms to the insoluble support. Preferably, the attaching is covalent attaching. It is desirable that the insoluble support comprises a resin comprising aldehyde-activated agarose.

In another embodiment, the method for immobilizing whole venom comprises a) providing an insoluble support; b) providing a single whole venom; and c) attaching the single whole venom to the insoluble support by covalent binding.

The present invention also contemplates a method of producing antivenom. In one embodiment, the producing method comprises a) providing one or more immunizing venoms; b) providing at least one avian species; and c) immunizing the avian species with one or more immunizing venoms, so that a neutralizing antivenom is produced. Preferably, the avian species comprises chickens.

The present invention also contemplates a method for purifying antivenom. In one embodiment, the purifying method comprises a) providing, in any order: i) at least one antivenom comprising immunoglobulin of which less than 50% is venom-reactive, ii) at least one antigen matrix comprising at least one venom immobilized on an insoluble support, iii) at least one first and one second eluent; b) applying antivenom to the antigen matrix so that greater than ninety percent of the venom-reactive immunoglobulin binds the venom immobilized on the insoluble support of the antigen matrix; c) dissociating at least fifty percent of the bound venom-reactive immunoglobulin from the venom with the first eluent; and d) stripping the antigen matrix of substantially all of the venom-reactive immunoglobulin with the second eluent so that the antigen matrix is recyclable. It is desirable that the antivenom comprises horse antivenom.

Preferably, the antivenom comprises chicken antivenom and the chicken antivenom comprises yolk immunoglobulin.

The present invention also contemplates a method of analyzing antivenom. In one embodiment, the analyzing method comprises a) providing, in any order, i) a first and a second immunizing venoms, ii) a solution comprising antivenom comprising immunoglobulin subpopulations having reactivity with the immunizing venoms, iii) a first antigen matrix comprised of the first immunizing venom immobilized on an insoluble support, iv) a second antigen matrix comprised of a second immunizing venom immobilized on an insoluble support, and v) one or more eluents; b) applying the solution of antivenom to the first antigen matrix so that greater than 90% of the immunoglobulin reactive with the first immunizing venom is bound to the first antigen matrix and so that the solution passes through the first antigen matrix to create a first flow-through; c) applying the eluent to the first antigen matrix so that at least fifty percent of the bound immunoglobulin reactive with the first immunizing venom is dissociated to create a first eluate; and d) applying, in any order, i) the first flow-through to the second antigen matrix, followed by the eluent to create a second eluate, ii) the first eluate to the second antigen matrix so that the solution passes through the second antigen matrix to create a second flow-through, followed by the eluent to create a third eluate. In one embodiment, the method further comprises, after step d), comparing the venom-reactivity of the first flow-through, the first eluate, the second flow-through, the second eluate, and the third eluate, with the venom reactivity of the antivenom. It is desirable that the antivenom comprises horse antibody. Preferably, the antivenom comprises chicken antibody and the chicken antibody comprises yolk,immunoglobulin. It is desirable that, after applying the eluent, the first and second antigen matrices are rendered recyclable. A desirable recycling eluent is guanidine.

The present invention also contemplates a method of treatment. In one embodiment, the treatment comprises: a) providing i) avian antivenom in an aqueous solution in therapeutic amounts that is intravenously injectable, ii) at least one envenomed subject; b) intravenously injecting the avian antivenom into the subject. Preferably, the avian antivenom is chicken antivenom and the chicken antivenom comprises yolk immunoglobulin. It is desirable that the avian antivenom comprises immunoglobulin of which greater than fifty percent is venom-reactive. Preferably, the subject is a mammal.

In an alternative embodiment, the present invention contemplates a method of treatment, comprising: a) providing i) polyvalent antivenom in an aqueous solution in therapeutic amounts that is intravenously injectable, comprising immunoglobulin of which greater than fifty percent is venom-reactive, and having two or more monovalent subpopulations, ii) at least one envenomed subject; b) intravenously injecting the polyvalent antivenom into the subject. It is desirable that the polyvalent antivenom is horse antivenom.

It is not intended that the present invention be limited by the source of the venom used for immunizing, purifying or analyzing. Similarly, it is not intended that the present invention be limited by the source of the venom for which the antivenom compositions of the present invention are reactive. For example, the present invention contemplates venoms selected from the group consisting of Chordata, Arthropoda and Coelenterata venoms. Venoms selected from the group consisting of snake venoms, spider venoms, scorpion venoms or jelly fish venoms are specifically contemplated. The present invention also contemplates venom selected from the group consisting of *Crotalus scutulatus, Notechis scutatus, Acanthophis antarcticus, Oxyuranus scutellatus, Pseudonaja textilis, Pseudechis australis, Enhydrina schistosa, Ophiophagus hannah, Vipera ammodytes, Vipera aspis, Vipera berus, Vipera xanthina palestinae, Vipera lebetina, Cerastes cerastes, Cerastes vipera, Bitis arietans, Bitis gabonica, Vipera russelli, Echis carinatus, Trimeresurus flavoviridis, Aqkistrodon halys, A. piscivorus, A. contortrix, Naja naja, Naja n. haje, Naja n. kaouthia, Naja n. oxiana, Naja n. sputatrix, Naja n. atra, Naja nivea, Naja niqrocollis, Hemachatus hemachatus, Dendroaspis angusticeps, Dendroaspis jamesonii, Dendroaspis polylepis, Dendroaspis viridis, Bungarus caerulus, Bungarus fasciatus, Bungarus multicinctus, Aqkistrodon rhodostoma, Aqkistrodon acutus, Bothrops atrox, Bothrops jararaca, Bothrops jararacussu, Bothrops alternatus, Lachesis muta, Micrurus corralus, Micrurus fulvius, Micrurus frontalis, Micrurus niagrocinctus, Leiurus quincuestriatus, Tityus serrulatus, Centruroides suffusus, Centruroides noxius, Centruroides sculipturatus, Androctonus australis, Buthotus judaicus, Buthus tamalus, Latrodectus mactans, Latrodectus hesperus, Loxosceles reclusa,* and *Chironex fleckeri* venom. Preferably, the antivenoms of the present invention react with *C. atrox, B. atrox, C. adamanteus* and *C. durissus terrificus* venoms.

DESCRIPTION OF THE DRAWINGS

FIGS. 11A, 11B and 11C show the reactivity by ELISA of mammalian antivenom purified using one embodiment of the method of the present invention.

DESCRIPTION OF THE INVENTION

The present invention is directed to antivenoms and method for making antivenoms. The properties of antivenom of the present invention make the antivenoms multipurpose; antivenoms prepared according to the present invention are useful for analytical studies in vitro and useful as therapeutic agents.

Figure 1:
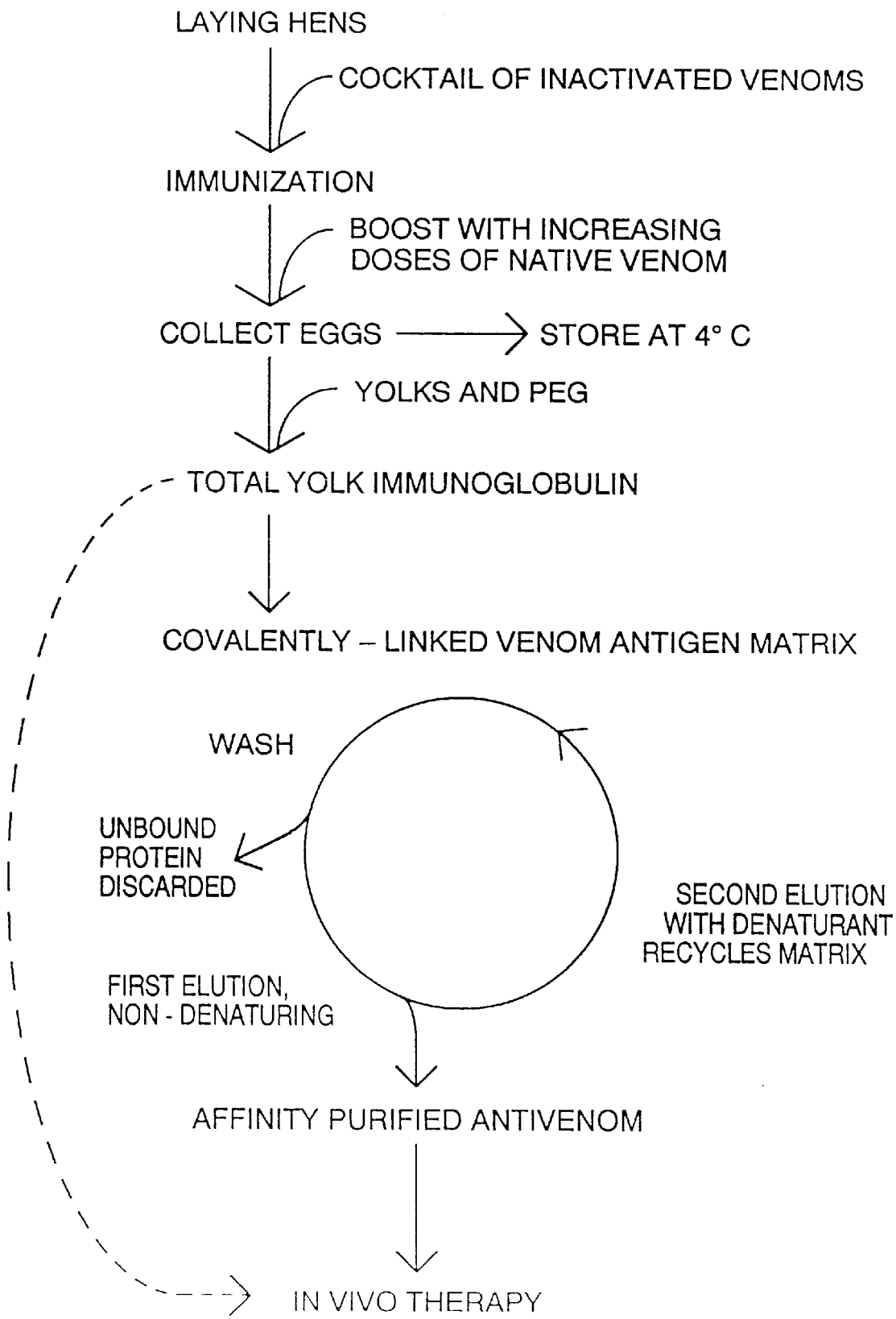
FIG. 1 is a schematic, showing a preferred embodiment of the method of the present invention.

The present invention contemplates I) producing antivenoms in non-mammals, and II) increasing the effectiveness of both non-mammalian antivenoms and mammalian antivenoms, however they might have been produced. The present invention further contemplates III) treating humans and animals by in vivo administration of antivenoms. A preferred embodiment of the method of the present invention is shown in FIG. 1 illustrating the temporal relationship of the method steps. The individual steps are described separately below.

I. Obtaining Antivenoms in Non-Mammals

A preferred embodiment of the method of the present invention for obtaining antivenoms involves immunization. However, it is also contemplated that antivenoms could be obtained from non-mammals without immunization. In the case where no immunization is contemplated, the present invention may use non-mammals with preexisting antibodies to toxins and/or venoms as well as non-mammals that have antibodies to toxins and/or venoms by virtue of reactions with the administered (non-venom) antigen. An example of the latter involves immunization with synthetic peptides or recombinant proteins sharing epitopes with venom components.

In a preferred embodiment, the method of the present invention contemplates immunizing non-mammals with whole venom(s). It is not intended that the present invention be limited to any particular venom. Venom from all venomous sources (see Table 1) are contemplated as immunogens.

When immunization is used, the preferred non-mammal is from the class Aves. All birds are comtemplated (e.g. duck, ostrich, emu, turkey, etc.). A preferred bird is a chicken. Importantly, chicken antibody does not fix mammalian complement. See H. N. Benson et al., J. Immunol. 87:610 (1961). Thus, chicken antibody will normally not cause a complement dependent reaction. A. A. Benedict and K. Yamaga, In: Comparative Immunology (J. J. Marchaloni, Ed.), Ch. 13, Immunoglobulins and Antibody Production in Avian Species (pp. 335–375) (Blackwell, Oxford 1966). Thus, the preferred antivenoms of the present invention will not exhibit complement-related side effects observed with antivenoms known presently.

When birds are used, it is contemplated that the antivenom will be obtained from either the bird serum or the egg. A preferred embodiment involves collection of the antivenom from the egg. Laying hens export immunoglobulin to the egg yolk ("IgY") in concentrations equal to or exceeding that found in serum. See R. Patterson et al., J. Immunol. 89:272 (1962). S. B. Carroll and B. D. Stollar, J. Biol. Chem. 258:24 (1983). In addition, the large volume of egg yolk produced vastly exceeds the volume of serum that can be safely obtained from the bird over any given time period. Finally, the antibody from eggs is purer and more homogeneous; there is far less non-immunogobulin protein (as compared to serum) and only one class of immunoglobulin is transported to the yolk.

It has been noted above that, when considering immunization with venoms, one may consider modification of the venom to reduce its toxicity. In this regard, it is not intended that the present invention be limited by immunization with modified venom. Unmodified ("native") venom is also contemplated as an immunogen.

It is also not intended that the present invention be limited by the type of modification—if modification is used. The present invention contemplates all types of venom modification, including chemical and heat treatment of the venom. The preferred modification, however, is heat-inactivation.

It is not intended that the present invention be limited to a particular mode of immunization; the present invention contemplates all modes of immunization, including subcutaneous, intramuscular, intraperitoneal, and intravascular injection.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant.

When immunization is used, the present invention contemplates a wide variety of immunization schedules. In one embodiment, a chicken is administered venom(s) on day zero and subsequently receives venom(s) in intervals thereafter. It is not intended that the present invention be limited by the particular invervals or doses. Similarly, it is not intended that the present invention be limited to any particular schedule for collecting antibody. However, a preferred schedule for immunization of the present invention is the administration of a cocktail of (heat-inactivated) venoms on day zero at 1 mg/ml for each venom, with subsequent administrations of the same cocktail (heat-inactivated or native) at the same dose on days 14 and 21, and with gradually increasing doses ("boosts") up to 10 mg/ml (native) at approximately two week intervals up to approximately one hundred days. The preferred collection time is sometime after day 100. This preferred immunization schedule results in the production of high quantities of reactive chicken antibody (i.e. reactive with the components of the immunized venom(s)) per ml of egg yolk (i.e. "high titers"). Furthermore, this preferred immunization schedule results in the production of antivenoms with "high avidity." High avidity is defined as antibody reactivity with multiple epitopes on individual venom components as measured by the formation of precipitin lines in Ouchterlony immunodiffusion gels at salt concentrations less than 1.5 M NaCl. Antivenoms requiring salt concentrations of 1.5 M NaCl or greater to form precipitin lines are "low avidity" antivenoms. While not limited to any precise mechanism, high avidity antivenoms have a greater probability of neutralizing venom components in vivo.

Where birds are used and collection of antivenom is performed by collecting eggs, the eggs may be stored prior to processing for antibody. It is preferred that storage of the eggs be performed at 4° C. for less than one year.

It is contemplated that chicken antibody produced in this manner can be buffer-extracted and used analytically. While unpurified, this preparation can serve as a reference for activity of the antibody prior to further manipulations (e.g. immunoaffinity purification).

II. Increasing the Effectiveness of Antivenoms

When purification is used, the present invention contemplates purifying to increase the effectiveness of both non-mammalian antivenoms and mammalian antivenoms. Specifically, the present invention contemplates increasing the percent of venom-reactive immunoglobulin. When evaluated for immunoglobulin content, purity and reactivity, at different stages of purification, preferred antivenoms of the present invention have the following relationship: less than 50% of the immunoglobulin of the polyvalent antivenom prior to purification (i.e. of the "first polyvalent antivenom") is venom-reactive; greater than 50% of the immunoglobulin of the polyvalent antivenom after purification is venom-reactive.

While all types of purification (e.g. purification based on size, charge, solubility, etc.) may be used, the preferred purification approach for mammalian antibody is immunoaffinity purification. The preferred purification approaches for avian antibody are: A) Polyethylene Glycol (PEG) separation, and B) Immunoaffinity purification.

A. PEG Purification

The present invention contemplates that avian antivenom be initially purified using simple, inexpensive procedures. In one embodiment, chicken antibody from eggs is purified by extraction and precipitation with polyethylene glycol (PEG). PEG purification exploits the differential solubility of lipids (which are abundant in egg yolks) and yolk proteins in high concentrations of polyethylene glycol 8000. Poison et al., Immunol. Comm. 9:495 (1980). The technique is rapid, simple, and relatively inexpensive and yields an immunoglobulin fraction that is significantly purer in terms of contaminating non-immunoglobulin proteins than the comparable ammonium sulfate fractions of mammalian sera and horse antivenoms. Indeed, PEG-purified antibody is sufficiently pure that the present invention contemplates the use of PEG-purified antivenoms in the passive immunization of envenomed humans and animals.

B. Immunoaffinity Purification

As noted, immunoaffinity purification is the preferred purification approach for both mammalian and avian antivenom. Immunoaffinity purification is separation based on the affinity of antibody for specific antigen(s); antibody that binds to specific antigen(s) is separated from antibody that does not bind (under the conditions used). The present invention contemplates the use of immunoaffinity purification to dramatically reduce the foreign protein burden of antivenoms by elimination of irrelevant protein (non-immunoglobulin and nonantigen-binding-immunoglobulin) when the antivenom is used therapeutically. While not limited to any specific theory, it is contemplated that a reduction in the protein burden will be accompanied by a reduction in side effects associated with passive immunization of foreign protein.

The present invention contemplates immunoaffinity purification by use of an "antigen matrix" comprised of venom (s) attached to an insoluble support. Antibody to be purified is applied in solution to the antigen matrix. The solution passes through the antigen matrix and comprises the "flow through." Antibody that does not bind, if present, passes with the solution through the antigen matrix into the flow through. To eliminate all non-binding antibody, the matrix is "washed" with one or more wash solutions which, after passing through the matrix, comprise one or more "effluents." "Eluent" is a chemical solution capable of dissociating antibody bound to the antigen matrix (if any) that passes through the antigen matrix and comprises an "eluate." Antibody that is dissociated (if any) is freed from the antigen matrix and passes by elution with the eluent into the eluate.

In one embodiment, the material for the insoluble support (hereinafter "resin") takes the form of spherical beads. In a preferred embodiment, the resin is a synthetic polymer capable of forming a gel in aqueous media (e.g. agarose).

The immunoaffinity purification of the present invention provides a number of benefits. First, the immunoaffinity purification of the present invention provides for maximum attachment of the antigen (e.g. venom) to the resin, i.e. high attachment efficiency. Second, the immunoaffinity purification of the present invention provides for the recovery of as much of the reactive antibody of the unpurified antibody (the preferred unpurified antibody is PEG-purified whole yolk IgY) as possible, i.e. the quantity of antibody purified is optimized. Third, the immunoaffinity purification of the present invention allows for the recovery of the antibody in an active state, i.e. the quality of reactivity is preserved. Fourth, the immunoaffinity purification of the present invention provides that the bound antibody be eluted quantitatively; there is no significant (less than two percent) retained antibody to progressively decrease column capacity after successive cycles of use, i.e. the antigen matrix is recyclable. Fifth, and most importantly, the immunoaffinity purification of the present invention allows for the retention in the purified antivenom of the spectrum of reactivity of the unpurified antivenom.

Most previous studies of polyclonal antibody purification have involved mammalian antibodies. No comparative information is available on the forces affecting the stability of chicken antibody-antigen complexes. Indeed, very little structural or chemical data has been compiled on the properties of chicken immunoglobulins (e.g., amino acid sequence of heavy and light chains, disulfide bond structures, three-dimensional structure, freeze-thaw and thermal stability, etc.).

The majority of immunoaffinity purification of antivenom that has been done has only used individual toxins and not whole venom. No comparative information is available on the forces affecting the stability of the whole venom antigen matrix.

The immunoaffinity purification of the present invention involves consideration of the venom(s) used to raise the antivenom that is to be immunoaffinity purified. In this regard, the present invention provides a method for evaluating the immunochemical similarity or dissimilarity of venoms that allows for i) means of designing cost-effective immunization cocktails for new antivenom formulas, ii) means of designing cost-effective antigen matrices for purifying new or existing antivenoms, iii) means of identifying the monovalent and polyvalent antibody subpopulations of an existing antivenom, and iv) means of determining its spectrum of reactivity of antivenom for the further design of antivenoms for treatment. Additional considerations include the nature of the resin, method of binding the venom(s) to the resin, method of applying the unpurified antivenoms, and method of recovering purified antivenom.

i. Venoms Used To Immunize

Every geographic area has its own unique collection of venomous species. The greater the immunochemical similarity of the venoms produced by these species, the greater the likelihood that antivenoms raised against one species will react with and neutralize other species. The more dissimilar the venoms, the greater the need is for antivenoms that react with a number of species so that individual species need not be identified in the case of an emergency.

Immunochemical similarity is better understood in terms of epitopes. An epitope is defined as an antibody combining site on an antigen. Where venom is the antigen, an epitope is a discrete (typically measured in angstroms) region of a venom component where antibody binds to the venom component. Where an epitope is not present in the venom of other species, it is referred to as a "species-unique epitopes." Where an epitope is common to venom of different species it is referred to as a "species-shared epitope." Where there is a single species-unique epitope in a venom, there is said to be immunochemical dissimilarity between the venom and any other venom. The greater the number of species-unique epitopes the greater the immunochemical dissimilarity.

Because of the practicality of treatment within one geographic area, the present invention contemplates raising antivenoms with a mixture of venoms (a "cocktail") as an immunogen. Using cocktails, the antivenoms of the present invention have reactivity with more than one venom. Furthermore, using the immunoaffinity purification of the present invention, the immunoaffinity purified antivenoms of the present invention retain this spectrum of reactivity. This is in contrast to existing antivenoms. Previously, the purification of antivenoms raised using mixtures of venoms has not preserved the spectrum of reactivity of the unpurified antivenom.

The present invention contemplates that antivenom is a "population" of antibodies. The population may be composed of one or more "subpopulations." Where more than one whole venom is used as an immunogen (and assuming the venoms are immunogenic), the resulting antivenom is "polyvalent." A polyvalent antivenom is herein defined as a population of antibodies having reactivity with all of the immunizing venoms. Where only one whole venom is used as an immunogen, the resulting antivenom is "monovalent."

A polyvalent antivenom may have "monovalent subpopulations," "polyvalent subpopulations," and/or "crossreactive subpopulations." In all cases, valency is defined by venom reactivity with immunizing venom(s) (and not by antibody class or subclass). Monovalent subpopulations of a polyvalent antivenom are herein characterized as subpopulations exhibiting reactivity with some but not all immunizing venoms. Polyvalent subpopulations of a polyvalent antivenom are herein characterized as subpopulations exhibiting reactivity with all of the immunizing venoms. Crossreactive subpopulations of a polyvalent antivenom are herein characterized as subpopulations exhibiting reactivity with non-immunizing venom(s).

Monovalent antivenoms may have "monovalent subpopulations" and "crossreactive subpopulations." Monovalent subpopulations of a monovalent antivenom are herein characterized as subpopulations exhibiting reactivity with the immunizing venom. Crossreactive subpopulations of a monovalent antivenom are herein characterized as subpopulations exhibiting reactivity with non-immunizing venom(s).

Subpopulation characterization is best understood by example and by ignoring reactivity with non-immunizing venoms. Where a first and a second whole venom are used together to immunize, the resulting polyvalent antivenom can in theory have i) a monovalent subpopulation of antibody reactive only with the first venom, ii) a monovalent subpopulation of antibody reactive only with the second venom, and iii) a polyvalent subpopulation of antibody (i.e. antibody reactive with both venoms). On the other hand, the resulting polyvalent antivenom could also comprise two monovalent subpopulations without any polyvalent subpopulation, or a polyvalent subpopulation without any monovalent subpopulations.

Whether in fact the resulting polyvalent antivenom does have monovalent subpopulations depends on whether the venoms used as immunogen have species-unique epitopes. Where there are no species-unique epitopes, there will be no monovalent subpopulations.

Polyvalent antivenom can be made either by a) immunizing with a venom cocktail or b) immunizing with single venoms and mixing two or more monovalent antivenoms. In either case, the reactivity of the subpopulation(s) determine the spectrum of reactivity of the population, i.e. the antivenom. Importantly, whether monovalent or polyvalent, the purification of the present invention allows for the quantitative retention in the purified antivenom of the spectrum of reactivity of the unpurified antivenom.

In nearly all previous studies, antitoxin and antivenom antibodies were purified using only a single toxin. Antibodies purified in this manner do not have the spectrum of reactivity required to neutralize the plurality of distinct toxins present in whole venoms. In the handful of studies using whole venom, the investigators used only single venom antigen matrices. Single venom antigen matrices are not capable of binding and purifying the spectrum of antivenom antibodies present in the polyvalent commercial antivenom investigated. Thus, purification in the manner described by these researchers necessarily resulted in antivenom with a more limited reactivity than the unpurified antivenom.

To retain the spectrum of reactivity, the present invention gives consideration to the venom(s) used to immunize when determining the appropriate venoms for immunoaffinity purification. In a preferred embodiment, the immunoaffinity purification of the present invention contemplates using the same venom or cocktail of venoms for purification as was used for immunization. By using the same venom or cocktail of venoms, the purified antivenom derived from unpurified antivenom has substantially the same spectrum of reactivity as the unpurified antivenom, where "substantially" is defined as greater than 50% of the antigen-binding reactivity of the unpurified antivenom with respect to each immunizing venom. As a relative value, the measurement of "50% reactivity" need not be made by any particular assay. Noetheless, conventional direct antigen-binding ELISA techniques are preferred. In other embodiments, the present invention contemplates using different venom or cocktails for purification as was used for immunization.

ii. Nature of the Resin

The present invention contemplates immobilization of venoms with an insoluble support. There are essentially three ways this can be achieved. First, venom components can be physically trapped in a gel; this approach does not rely upon any particular chemical reactivities of the venom components. Second, venom components can be covalently coupled to an "activated" matrix; this approach relies on the existence of functional groups on the venom components that can covalently bond with the matrix. Third, venom components can be coupled to insoluble supports using bifunctional reagents as linking groups that react with a) side groups on venom components and b) groups on the insoluble support.

As noted earlier, only individual venom components have thus far been covalently attached to a matrix; whole venom has not been immobilized in this manner. With single venom components, a number of factors, including mode of attachment, the type of resin, and the distance between the resin and the attached antigen, can influence the success of the immobilization approach. See e.g., V. Kukongviriyapan et al., J. Immunol. Meth. 49:97 (1982). With whole venoms these factors are multiplied and result in greater uncertainty.

One important issue in immobilizing whole venom is coupling efficiency: are the functional groups accessible such that the bulk of the venom components are coupled? Another issue involves antigenicity: does attachment to the matrix preserve (or destroy) the antigenicity of the venom components? With respect to the first issue, little is known about the chemical structure of most venom components. While the existence of reactive primary amines should allow for attachment to most activated matrices, there is no assurance that this will occur at a sufficient level to be useful. With regard to the second issue, it is possible that the functional groups involved in covalent attachment are part of, or near, important epitopes. Random alteration or steric hindrance of epitopes through covalent bonding of functional groups could dramatically influence the antibody binding capacity of the matrix. Non-random alteration or steric hindrance of epitopes could be expected to significantly impact the ability to recover immunoaffinity purified antivenom with the spectrum of reactivity of the unpurified antivenom.

In a preferred embodiment, the present invention provides a covalent attachment method for whole venom that allows for high coupling efficiency and high antibody binding capacity. It is preferred because of the ease and efficiency of antigen attachment, the stability of the attachment (relative to resins involving non-covalent attachment), and mechanical and chemical strength towards denaturants that are used during chromatographic procedures.

In one embodiment, the covalent attachment method employs cyanogen bromide activated Sepharose 4B (Pharmacia) as a resin for covalent attachment of whole venom. The preferred resins with active groups for covalent attachment are resins with aldehydes as active groups ("aldehyde-activated resins"), such as are described in U.S. Pat. No. 3,836,433 to Wirth et al., which is hereby incorporated by reference. A preferred resin is aldehyde-activated agarose. Chicken antibody eluted from such an antigen matrix exhibits a consistently higher venom binding activity (i.e. quality) than chicken antibody eluted from other antigen matrices.

iii. Binding Venom(s) To The Resin

It is not intended that the immunoaffinity purification of the present invention be limited to any particular venom or mixture of venoms. In the preferred embodiment, however, a cocktail is used. The preferred binding of the venom, whether single whole venoms or cocktails of whole venom, to an aldehyde-activated resin is via sodium cyanoborohydride reduction.

In a preferred embodiment, the antigen matrix is "pre-stripped" with an eluent prior to any further use of the antigen matrix. By pre-stripping, the purification of the present invention avoids contamination of immunoaffinity purified antivenom preparations with venom that failed to attach to the resin.

iv. Applying Unpurified Antivenom

It was noted above that by using the same venom or cocktail of venoms in the antigen matrix as was used in immunization, the purified antivenom derived from unpurified antivenom has substantially the same spectrum of reactivity of the unpurified antivenom. The maximum retention of the spectrum of reactivity is achieved when one, in addition using the same venom or cocktail of venoms in the antigen matrix as was used in immunization, uses the venom or cocktail of venoms in the antigen matrix at a concentration that allows for the presentation of antigen in greater amounts than that needed to bind all of the specific antibody applied to the antigen matrix. The latter is achieved by monitoring the flow through for reactivity as the unpurified antibody is applied; where the flow through shows less than 10% of the reactivity of the unpurified antibody that is applied, the venom or cocktail of venoms in the antigen matrix is viewed to be at a concentration that allows for the presentation of antigen in greater amounts than that needed to bind all of the specific antibody applied to the antigen matrix.

v. Recovering Purified Antivenom

In the preferred embodiment, the purification of the present invention contemplates sequential elution steps. By using sequential elution steps, the purification of the present invention overcomes the problem of poor recyclability that is associated with traditional purification methods.

In the preferred embodiment, the purification of the present invention allows for quantitative purification of the venom-specific antibodies present initially in the egg yolk IgY, retention of antibody antigen-binding activity, and recyclability of the matrix, by a first elution with a non-denaturing eluent and a second elution with denaturing eluent. The second elution recovers the remaining portion of antibody and recycles the antigen matrix. Thus, following application of crude antivenom, a preferred embodiment of the method of the present invention comprises the steps: 1) washing the matrix with a first buffer, 2) washing the matrix with a second buffer, 3) washing the matrix with a third buffer, 4) dissociating specific antibody from the venom with a first eluent, 5) washing the matrix again with the third buffer, 6) stripping the column of substantially all non-venom protein with a second eluent, 7) re-equilibrating the column for recyclability with the first buffer, and 8) removing eluent from the dissociated, specific antibody, wherein the first buffer is a phosphate-containing, low-ionic strength, non-detergent-containing, neutral pH buffer, the second buffer is a high ionic strength, non-ionic detergent-containing, slightly alkaline buffer, the third buffer is a non-phosphate-containing, low ionic strength, non-detergent-containing, neutral pH buffer, the preferred first eluent is a non-denaturing solution compatable with an extended residence time to dissociate bound antibody, the preferred second eluent is a strongly denaturing solution that rapidly dissociates the antibody that was not released by the first eluent, and the removal of both eluents from the dissociated antibody is performed by extensive dialysis against a low ionic strength, non-detergent-containing, neutral pH buffer.

While not limited to any particular theory, it is believed that the first buffer washes the bulk of the unbound protein from the matrix. The second buffer is of high ionic strength in order to wash non-venom-reactive, electrostatically-bound proteins from the matrix, and contains a non-ionic detergent to wash non-venom-reactive, hydrophobically-bound proteins from the matrix. Neither the high ionic strength nor the non-ionic detergent should disrupt specific antibody-antigen interactions. The third buffer does not contain phosphate because phosphate is not compatible with the preferred first eluent. After the first eluent, it is highly desirable that the matrix be equilibrated with the third buffer to wash the remaining eluent from the matrix before the second eluent is applied. After the second eluent, the phosphate-containing first buffer is used to remove the second eluent and to re-equilibrate the matrix in preparation for a new purification cycle.

In a preferred embodiment, the present invention contemplates 4M guanidine-HCl pH 8.0 as a second eluent to dissociate the antigen-antibody complexes formed between the immobilized venom and the chicken antibody specific for the antigen, because of its efficiency, solubility at 4° C. and ease of removal by dialysis.

It was determined that 0.1M glycine pH 2.5 as a first eluent caused unsatisfactory qualitative effects (high background sticking to solid surfaces and aggregation of renatured antibody) on chicken antibodies. Similarly, 4M guanidine-HCl, when used as a first eluent, eluted material that possessed only 17–49% of the original activity of the unpurified chicken IgY.

vi. Assessment of the Spectrum of Reactivity

As noted above, whether in fact the resulting polyvalent antivenom does have monovalent subpopulations depends on whether the venoms used as immunogen have species-unique epitopes. The present invention contemplates determining whether a species' venom has species-unique and/or species-shared epitopes (relative to other species' venom). The present invention contemplates making this determination using both i) antibody raised against single venoms (i.e. monovalent antivenoms), and ii) antibody raised against a plurality of venoms (i.e. polyvalent antivenoms). In this manner, the antivenoms of the present invention are useful in the selection of the appropriate venom and cocktails as immunogens for the production of the preferred polyvalent antibodies for treatment.

Figure 2:
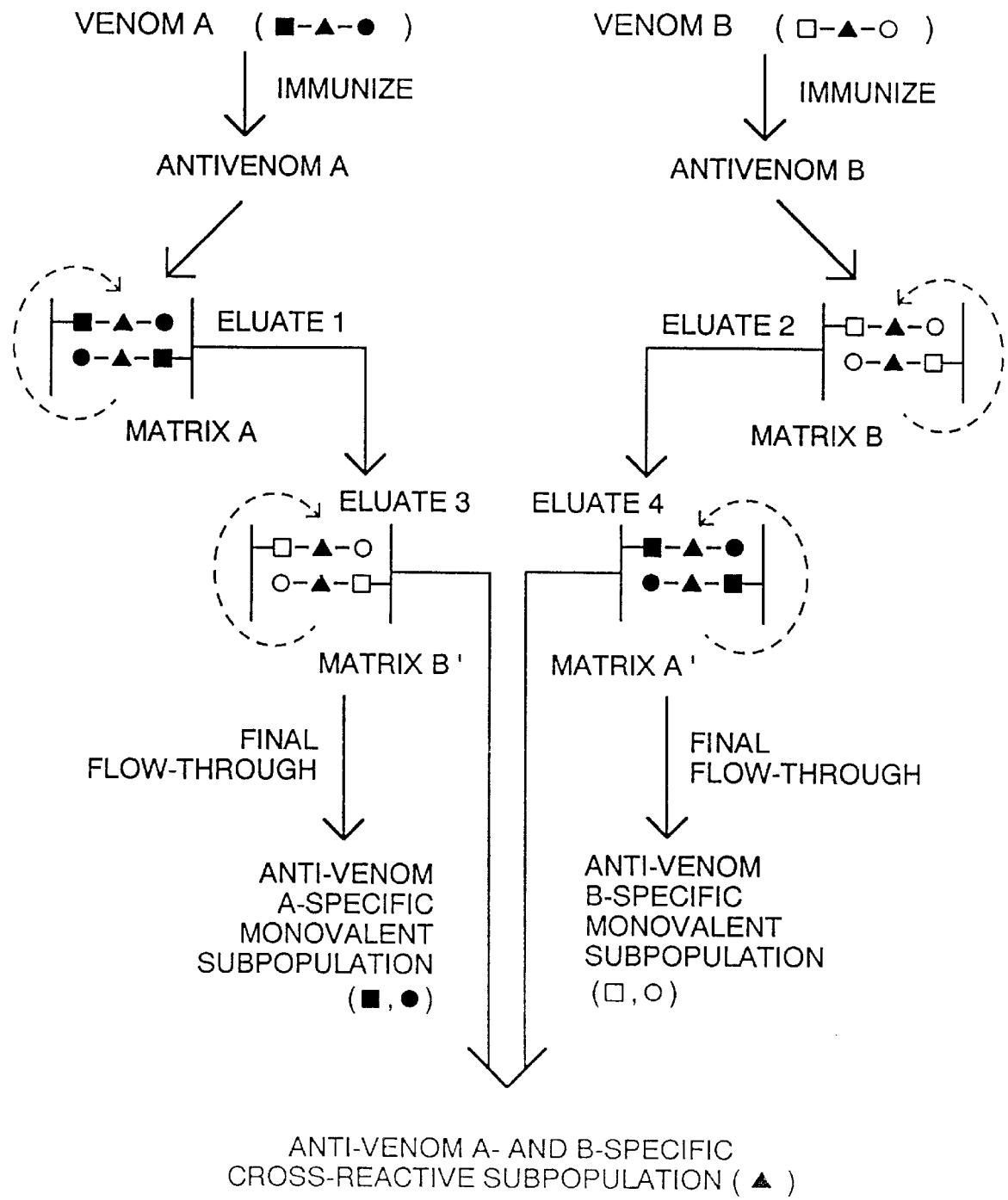
FIG. 2 is a schematic, showing one approach to venom epitope determinations of the present invention.

FIG. 2 shows schematically one approach to determining whether a species' venom has species-unique and/or species-shared epitopes. In this example, two antivenoms are used: one raised by immunization with Venom A and the other raised by immunization with Venom B. Depending on the source of the antivenoms, a prestep (not shown) may be desirable to eliminate viscosity and hydrophobicity problems during purification (e.g. chicken antivenom derived from eggs should be PEG-treated in a prestep procedure to eliminate lipids). For ease of understanding, FIG. 2 has been drawn to show species-unique epitopes (dark squares and circles for Venom A and open squares and circles for Venom B) as well as species-shared epitopes (dark triangles).

Antivenom A and Antivenom B are immunoaffinity purified separately over their respective immunizing venom immobilized to make an antigen matrix (Matrix A and Matrix B). The flow-through in each case is reapplied to assure quantitative recovery and then discarded (dotted lines). After washing, the bound antibody is eluted. The existence of antibody (if present) is detected in each eluate (Eluate 1 is from Matrix A; Eluate 2 is from Matrix B) by ultraviolet light absorption at 280 nm ("$A_{280}$").

The eluates in each case are then applied to the respective non-immunizing venom as an antigen matrix; Eluate 1 is applied to Matrix B' and Eluate 2 is applied to Matrix A' (Matrix A can be the same as Matrix A' or can be a duplicate; Matrix B can be the same as Matrix B' or can be a duplicate). Again, the flow-through in each case is reapplied to assure quantitative recovery (dotted lines). The final flow-throughs are collected for characterization. The existence of non-binding antibody in the flow-through is determined by $A_{280}$. After washing, the bound antibody (if any) is eluted and collected for characterization. The existence of antibody (if present) is detected in each eluate (Eluate 3 is from Matrix B'; Eluate 4 is from Matrix A') by $A_{280}$.

Where antibody is detected in the final flow-throughs, this antibody must be non-crossreactive. This indicates there are one or more species-unique epitopes and consequently one or more monovalent subpopulations. Where antibody is detected in the final eluates, this antibody must be crossreactive. This indicates there are one or more species-shared epitopes and consequently one or more crossreactive subpopulations.

Figure 3:
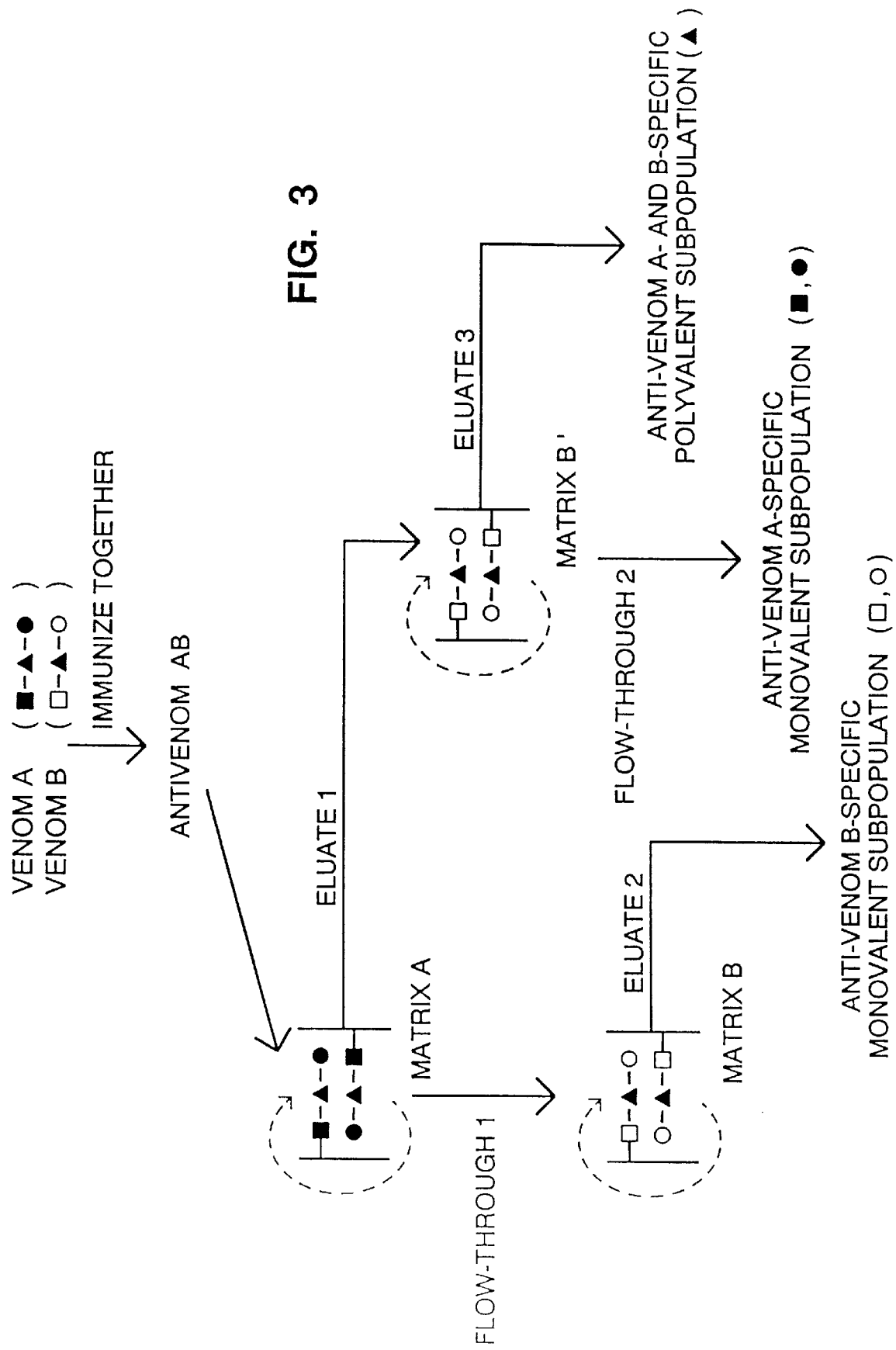
FIG. 3 is a schematic, showing a preferred approach to venom epitope determinations of the present invention.

FIG. 3 shows schematically a preferred approach to determining whether a species' venom has species-unique and/or species-shared epitopes. In this example, one antivenom is used; the antivenom was raised by immunization with Venom A together with Venom B. Again, for ease of understanding, FIG. 3 has been drawn to show species-unique epitopes (dark squares and circles for Venom A and open squares and circles for Venom B) as well as species-shared epitopes (dark triangles).

Antivenom AB is immunoaffinity purified sequentially over the immunizing venoms used individually as antigen matrices (Matrix A, Matrix B and Matrix B'). The flow-throughs in all cases are reapplied (dotted lines) to assure quantitative recovery of specific antibody. The flow-through from Matrix A (Flow-Through 1) is then applied to Matrix B. After washing both Matrix A and Matrix B, the bound antibody is eluted. The existence of antibody (if present) in each eluate (Eluate 1 is from Matrix A; Eluate 2 is from Matrix B) is detected by $A_{280}$.

Eluate 1 is applied to Matrix B' (Matrix B can be the same as Matrix B' or can be a duplicate). The flow-through (Flow-Through 2) is collected for characterization. The existence of non-binding antibody (if present) in the flow-through is determined by $A_{280}$. After washing Matrix B', the bound antibody (if any) is eluted and collected for characterization. The existence of antibody (if present) in this eluate (Eluate 3) is detected by $A_{280}$.

Where antibody is detected in Eluate 2, this antibody must be non-reactive with Venom A, but reactive with Venom B. This indicates there are one or more species-unique epitopes and consequently one or more monovalent subpopulations. Where antibody is detected in Eluate 3, this antibody must be reactive with both Venom A and Venom B. This indicates there are one or more species-shared epitopes and consequently one or more polyvalent subpopulations.

A comparison of FIG. 2 with FIG. 3 shows that the use of a cocktail immunogen (FIG. 3) allows for the same determinations with fewer "runs" (i.e. elutions from antigen matrices). This advantage continues and, indeed, becomes more significant when epitope determinations are desired for greater numbers of venoms. For example, where three venoms need to be analyzed, a cocktail immunogen approach allows for epitope determinations with only seven runs, while a single venom immunogen approach requires twelve runs.

Figure 4:
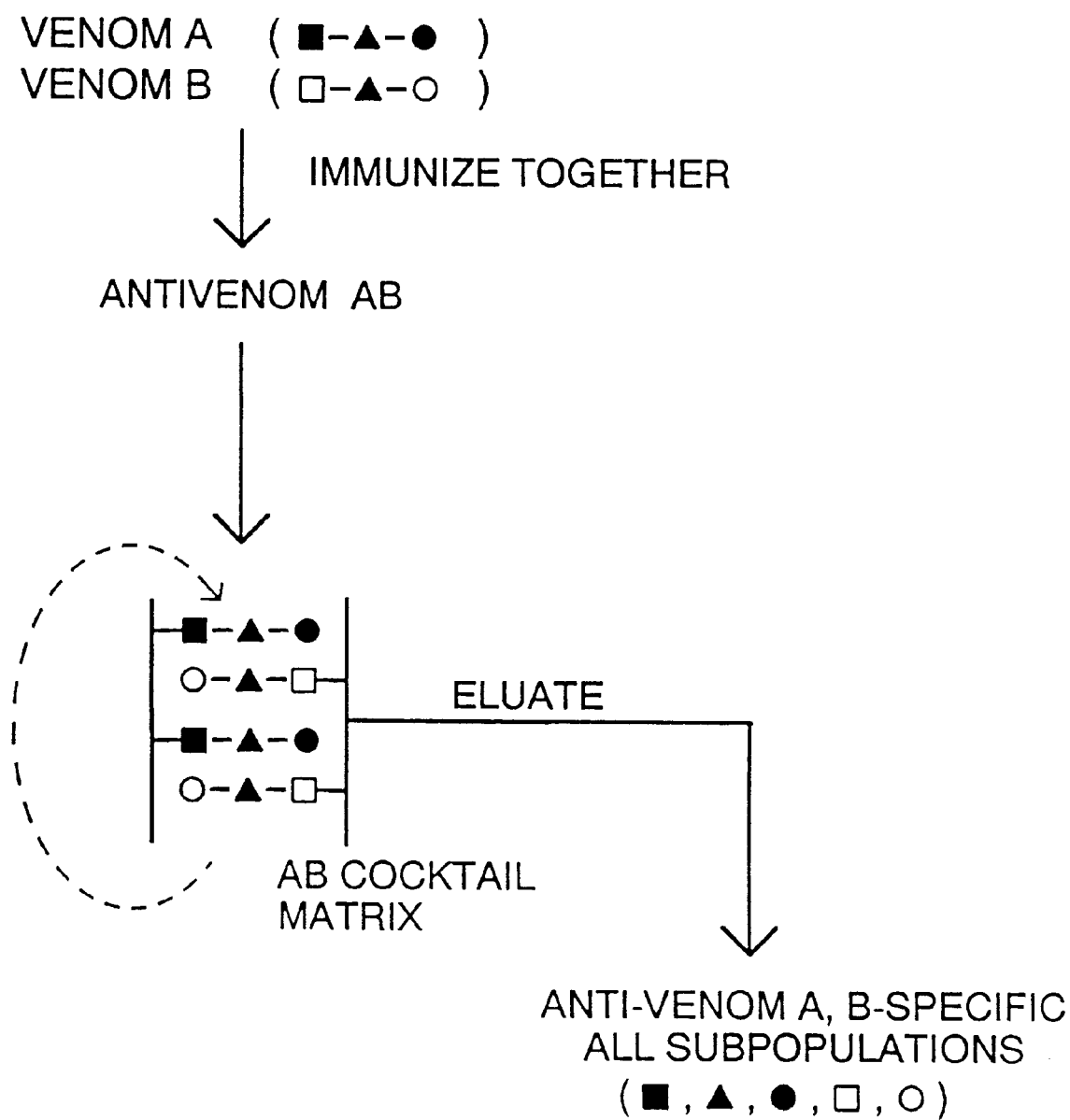
FIG. 4 is a schematic, showing a preferred approach to antivenom immunoaffinity purification of the present invention.

Once epitope determinations are made for the venoms of interest, a preferred cocktail matrix can be designed for immunoaffinity purification such that the purified antivenom retains the spectrum of reactivity of the unpurified antivenom. While a cocktail matrix containing all of the immunizing venoms will (if used in a quantitative protocol) invariable retain the spectrum of reactivity (see FIG. 4), elimination of venoms having no species-unique epitopes may be desired where large-scale (e.g. commercial) purifications are to be performed with scarce and/or expensive venom(s).

III. Treatment

The present invention contemplates antivenom therapy for envenomed humans and animals. The method of antivenom treatment of the present invention involves consideration of a) venom identification, b) degree of envenomation, and c) type and dose of antivenom to be administered.

A. Venom Identification

Commonly, the venomous species is not seen, let alone captured for identification, at the time of envenomation. The lack of reliable species identification, particularly in emergency situations, taken together with the cost of raising antivenom, makes it preferrable that the antivenoms used in treatment not be limited in their reactivity to a single species. Thus, in a preferred embodiment, the present invention contemplates raising polyvalent antivenoms according to the potential for envenomation by venomous inhabitants of any particular geographical area.

B. Degree of Envenomation

Not all venoms are potentially fatal; even bites or stings from the most potent species may not be life-threatening if a relatively low degree of envenomation occurs. A key clinical dilemma, however, results from the fact that the amount of venom delivered is highly variable and the attending medical personnel must rely on the victim's symptoms in assessing the extent of the overall threat of serious injury or death. These symptoms include, but are not limited to, local pain, hemorrhaging, numbness, edema, necrosis, nausea, vomiting, blood clotting abnormalities, faintness, proteinuria, respiratory distress and paralysis. Importantly, the severity of these symptoms must be considered in connection with the time after envenomation. Typically, symptoms are more severe over time. Thus, less severe symptoms early on do not ensure a low level of envenomation. The qualitative nature of these symptoms and the frequent difficulty in establishing a meaningful time frame make a determination of the degree of envenomation approximate at best.

C. Dosage of Antivenom

It was noted by way of background that a balance must be struck when administering currently available antivenom; sufficient antivenom must be administered to neutralize the venom, but not so much antivenom as to increase the risk of untoward side effects. These side effects are caused by i) patient sensitivity to horse proteins, ii) anaphylactic or immunogenic properties of non-immunoglobulin proteins, iii) the complement fixing properties of mammalian antibodies, and/or iv) the overall burden of foreign protein administered. It is extremely difficult to strike this balance when, as noted above, the degree of envenomation (and hence the level of antivenom therapy needed) can only be approximated.

The present invention contemplates significantly reducing side effects so that this balance is more easily achieved. Treatment according to the present invention contemplates reducing side effects by using i) immunoaffinity purified antivenom from mammalian sources, ii) PEG-purified antivenom from birds, and/or iii) immunoaffinity purified antivenom from birds.

In one embodiment, the treatment of the present invention contemplates the use of immunoaffinity purified antivenom from mammalian sources. While complement-fixing, immunoaffinity purification of antivenom from mammalian sources reduces the total protein burden up to approximately twenty fold. This means that approximately twenty times more venom-reactive antibody can be administered before the risk of serum sickness reaches that of the currently available antivenom.

In another embodiment, the treatment of the present invention contemplates the use of PEG-purified antivenom from birds. The use of yolk-derived, PEG-purified antibody as antivenom allows for the administration of 1) non (mammalian)-complement-fixing, avian antibody, 2) a less heterogeneous mixture of non-immunoglobulin proteins, and 3) only one-third as much total protein to deliver the equivalent weight of active antibody present in currently available antivenom. This means that approximately three times more venom-reactive antibody can be administered before the risk of serum sickness reaches that of the currently available antivenom. The non-mammalian source of the antivenom makes it useful for treating patients that are sensitive to horse or other mammalian serums. PEG-purified antivenom is useful for treating victims where the amount of antivenom required is relatively small or the cost of affinity purification is prohibitive. The amount of antivenom required may be relatively small (<250 mg) when the extent of systemic envenomation is slight. For instance, low envenomation may occur in the case of certain scorpion species, very small or immature snakes, or snake species that typically deliver small (<5 mg) of venom in a single bite. Cost is prohibitive in certain regions of the world; such areas cannot sustain the financial burden of immunoaffinity reagents and the skilled labor necessary to produce highly-purified antivenoms.

In a preferred embodiment, the treatment of the present invention uses yolk-derived, immunoaffinity purified antibody as antivenom, which allows for the administration of 1) non-complement-fixing antibody, and 2) only ⅟₂₀th as much total protein to deliver the equivalent weight of active antibody present in currently available antivenom. This means that twenty times more venom-reactive antibody can be administered before the risk of serum sickness reaches that of the currently available antivenom. Thus, physicians may treat victims more aggressively with far greater amounts of active antivenom without fear of increased side effects. Because the initial foreign protein exposure is reduced, the risk of sensitizing a patient to antivenom is also reduced. This is important where the patient must undergo subsequent antivenom treatment.

Experimental

The following examples serve to illustrate certain preferred embodiments and aspects of the present invention and are not to be construed as limiting the scope thereof.

In the disclosure which follows, the following abbreviations apply: $A_{280}$ (Absorbance at 280 nm); eq (equivalents); M (Molar); $\mu M$ (micromolar); N (Normal); mol (moles); mmol (millimoles); $\mu$mol (micromoles);; nmol (nanomoles); gm (grams); mg (milligrams); $\mu g$ (micrograms); L (liters); ml (milliliters); $\mu l$ (microliters); ° C. (degrees Centigrade); CFA (Complete Freund's Adjuvant); IFA (Incomplete Freund's Adjuvant); ELISA (Enzyme-linked Immunosorbent Assay); MW (molecular weight); OD (optical density); EDTA (ethylene-diaminetetracetic acid); PAGE (polyacrylamide gel electrophoresis); Aldrich (Aldrich Chemical Co., Milwaukee, Wis.); Beckman (Beckman Instruments, San Ramon, Calif.); BRL (Bethesda Research Laboratories, Gaithersburg, Md.); Cappel (Cappel Laboratories, Malvern, Pa.); Eastman (Eastman Kodak, Rochester, N.Y.); Fisher (Fisher Biotech, Springfield, N.J.); GIBCO (GIBCO, Grand Island, N.Y.); Gilford (Gilford, Oberlin, Ohio); IBF (IBF Biotechnics, Savage, Md.); Mallinckrodt (Mallinckrodt, St. Louis, Mo.); Pierce (Pierce Chemical Co., Rockford, Ill.); Sigma (Sigma Chemical Co., St. Louis, Mo.); Wyeth (Wyeth Laboratories, Marietta, Pa.).

For convenience when discussing antivenoms, the immunized animal used as the source is used as a modifier in front of the term "antivenom" (e.g. "horse antivenom" means antivenom raised in a horse and "chicken antivenom" means antivenom raised in a chicken).

The antivenom used as starting material and/or control antivenom in some examples below (hereinafter "unpurified horse antivenom") was obtained from Wyeth (lot #M878035) This unpurified horse antivenom has been used extensively by others for the treatment of humans afflicted with venomous bites. D. C. Christopher and C. B. Rodning, S. Med. J. 79:159 (1986). M. J. Ellenhorn and D. G. Barceloux, Medical Toxicology, Ch. 39 (Elsevier Press 1988).

H. M. Parrish and R. H. Hayes, Clin. Tox. 3:501 (1970). F. E. Russell et al., JAMA 233:341 (1975).

EXAMPLE 1

Production of an antivenom to a cocktail of modified snake venoms in a non-mammal.

To determine the best course for raising high titer egg antibodies against venoms, the effect of various methods of venom modification was examined. In order to demonstrate that, as a result of modification, toxicity would be inactivated but antigenicity would be preserved. The example involved a) venom modification, b) immunization, c) antivenom collection, and d) antigenicity assessment.

a) Venom modification: Crotalus atrox venom (Sigma) was modified by formaldehyde, glutaraldehyde or heat treatment. In order to monitor the inactivation of venom, the inhibition of total venom protease activity was measured according to a modified method of V. B. Philpot, Jr. et al., Toxicon 16, 603 (1978). The assay consisted of mixing 10 microliters of venom or buffer control with 25 microliters of azo-coupled cowhide beads (Sigma) in 200 microliters of PBS for five to fifteen minutes. Protease activity is detected when the supernatant turns red due to hydrolysis of the azo dye. Results were quantitated at $A_{525}$ on a spectrophotometer (Gilford).

With respect to inactivation, it is not necessary that complete inhibition be achieved. It is simply desirable as a means of minimizing the impact of immunization in the immunized animal.

For formaldehyde treatment, a 10 mg/ml dilution of whole C. Atrox venom was made in various concentrations of formaldehyde (0.25–8.0% w/v) and left for 1 hour at room temperature. Because it was observed that 8.0% formaldehyde gave complete inhibition of venom protease activity, these conditions were used to prepare the formaldehyde-treated immunogen.

For glutaraldehyde treatment, a 10 mg/ml dilution of whole C. Atrox venom was made in glutaraldehyde and left for 1 hour at room temperature. Because it was observed that 1% glutaraldehyde totally inactivated venom protease activity, this concentration was used to prepare the formaldehyde-treated immunogen.

For heat treatment, a 10 mg/ml dilution of whole *C. Atrox* was heated to 95° C. in a water bath for five minutes and then plunged into ice. This treatment abolished all protease activity and was, therefore, the treatment used to prepare heat-treated immunogen.

b) immunization: Two, one-year old white leghorn hens were each immunized with 1 mg of *Crotalus atrox* venom after it was treated according to one of the inactivation methods described above (total of six immunized hens). The hens were injected with the inactivated venom in CFA (GIBCO) on day zero subcutaneously in multiple sites (both sides of the abdomen, both breasts, and in both wings to involve more of the lymphatic system). The hens were subsequently injected with 1 mg of the same inactivated venom in IFA (GIBCO) on Day 11 and Day 19.

c) antivenom collection: Chicken immunoglobulin (IgY) was extracted according to a modification of the methods of A. Polson et al., Immunol. Comm. 9:495 (1980). A gentle stream of distilled water from a squirt bottle was used to separate the yolks from the whites, and the yolks were broken by dropping them through a funnel into a graduated cylinder. The broken yolks were blended with 7 volumes of egg extraction buffer to improve antibody yield (Egg extraction buffer=0.01 M Sodium phosphate, 0.1 M NaCl, pH 7.5, containing 0.01% $NaN_3$), and PEG 8000 (Baker) was added to a concentration of 3.5%. When all the PEG dissolved, the protein precipitate that formed was pelleted by centrifugation at 9000×g for 10 minutes. The supernatant was decanted and filtered through cheesecloth to remove the lipid layer, and PEG was added to a final concentration of 12% (we assumed the supernatant was 3.5% PEG). The solution was centrifuged as above, the supernatant discarded, the pellet redissolved in 2 times the original yolk volume of egg extraction buffer, and PEG added to 12% for a second precipitation. After centrifugation the supernatant was discarded and the pellet centrifuged twice more to extrude the PEG. This crude IgY pellet was then dissolved in the original yolk volume of egg extraction buffer and stored at 4° C.

d) antigenicity assessment: Eggs were collected during the day 25–day 28 period (and stored intact at 4° C. for approximately six months) to assess whether the venoms were sufficiently antigenic to raise an antibody. Eggs from the two hens in each modification group were pooled and antibody was collected as described above. Antigenicity was assessed on Western Blots according to the method of H. Towbin et al. Proc. Nat. Acad. Sci. USA 76:4350 (1979). 100 µg samples of three distinct venom types (*Crotalus adamanteus, Crotalus atrox,* and *Aqkistrodon piscivorus*) were dissolved in SDS reducing sample buffer (1% SDS, 0.5% 2-mercaptoethanol, 50 mM Tris pH 6.8, 10% glycerol, 0.025% w/v bromophenol blue), heated at 95° C. for 10 minutes and separated on a 1 mm thick, 12% SDS-polyacrylamide gel. K. Weber and M. Osborn, In: The Proteins, 3rd Edition (H. Neurath and R. L. Hill, Eds.) (Academic Press, NY) (pp. 179–223). Part of the gel was cut off and the proteins stained in Coomassie Blue. The proteins in the remainder of the gel were transferred to nitrocellulose using the ABN polyblot electro-blotting system according to the manufacturers instructions (Fisher). The nitrocellulose was temporarily stained with 10% Ponceau S (S. B. Carroll and A. Laughon, In: DNA Cloning: A Practical Approach, Vol. III, D. Glover, Ed., IRL Press, Oxford, pp. 89–111)) to visualize the lanes, then destained by running a gentle stream of distilled water over the blot for several minutes. The nitrocellulose was immersed in PBS containing 3% BSA overnight at 4° C. to block any remaining protein binding sites.

The blot was cut into strips and each strip was incubated with the appropriate primary antibody. The three primary antibodies discussed above were used (along with pre-immune chicken antibody as a control) diluted 1:250 in PBS containing 1 mg/ml BSA for 2 h at room temperature. The blots were washed with 2 changes each of large volumes of PBS, BBS-Tween and PBS successively (10 min/wash). Goat anti-chicken IgG alkaline phosphatase conjugated secondary antibody (Fisher Biotech) was diluted 1:400 in PBS containing 1 mg/ml BSA and incubated with the blot for 2 hours at room temperature. The blots were washed with 2 changes each of large volumes of PBS and BBS-Tween, followed by 1 change of PBS and 0.1M Tris-HCl, pH 9.5. Blots were developed in freshly prepared alkaline phosphatase substrate buffer: 100 µ/ml Nitro-Blue Tetrazolium (Sigma), 50 µg/ml 5-Bromo-4-Chloro-3-Indolyl Phosphate (Sigma), and 5 nM $MgCl_2$ in 50 mM $Na_2CO_3$ pH 9.5.

Figure 5:
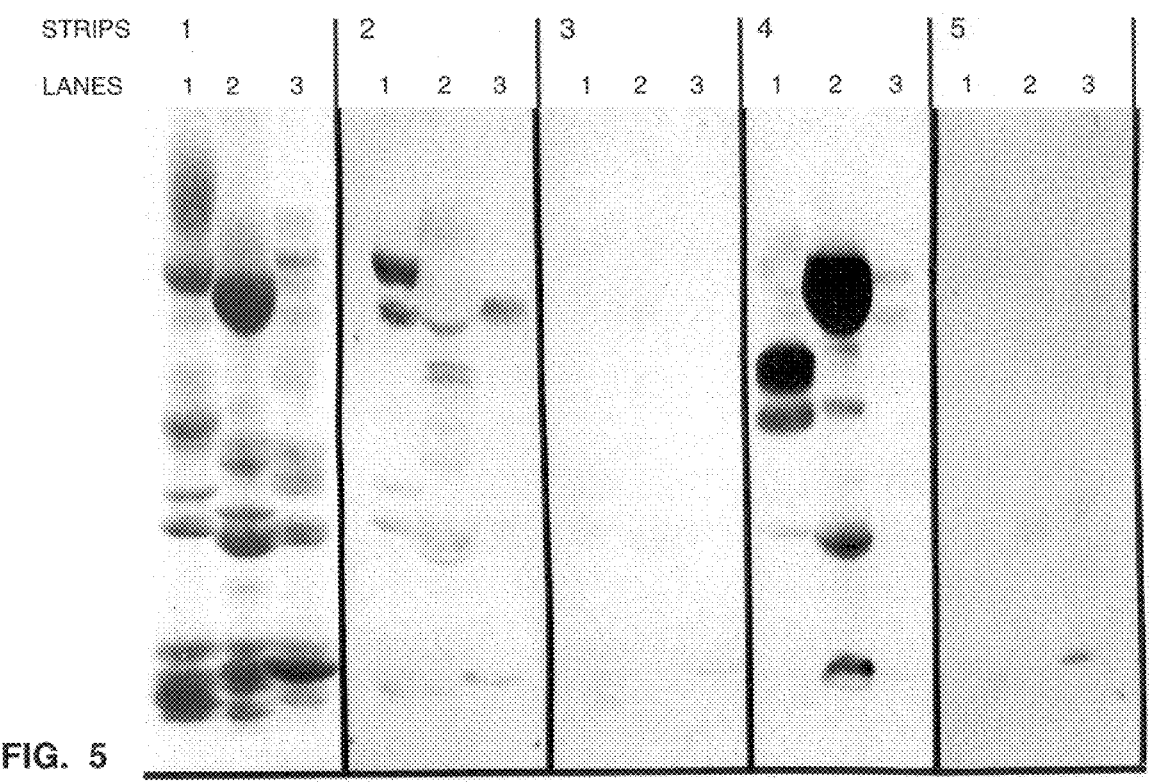
FIG. 5 is a Western Blot, showing the reactivity of antivenoms raised against modified venoms.

The results are shown in FIG. 5. The Coomassie Blue strip (Strip 1) illustrates the order of the venoms put in all the other strips: *Crotalus adamanteus* was placed in Lane 1; *Crotalus atrox,* was placed in Lane 2; *Aqkistrodon piscivorus* was placed in Lane 3. From FIG. 5, antibody reactivity is seen in Strips 2 (formaldehyde-treated immunogen) and 4 (heat-treated immunogen); very little reactivity can be seen in Strips 3 (glutaraldehyde-treated immunogen) and 5 (no immunogen). This suggests that, while the glutaraldehyde treatment was useful to reduce protease activity, the treatment denatured the venom to the point where antigenicity was also severely reduced. In terms of antigenicity, it appears from FIG. 5 that there is the following relationship among the different treatments: heat-treated>formaldehyde-treated>glutaraldehyde-treated.

Importantly, the chicken antibody recovered from the eggs reacts with many protein bands in Lane 2 (the *C. atrox* venom preparation) of Strips 2 and 4. The presence of many protein bands illustrates the complexity of the various venoms. Some of these protein bands from the different venoms appear to co-migrate, suggesting that there might be proteins in common among the venoms. Interestingly, while the antivenom was raised against a single venom (*C. atrox*), the results from Lanes 1 (the *Crotalus adamanteus* preparation) and 3 (the *Aqkistrodon piscivorus* preparation) of Strips 2 and 4 indicate that the chicken antibody reacts with non-immunizing venoms, i.e. is crossreactive. Clearly, there is a set of antigenically related proteins in the three different venoms.

EXAMPLE 2

Adjuvant effects on antivenom titers. To determine the best course for raising high titer egg antibodies against venoms, the impact of different types of adjuvants was demonstrated. The example consisted of a) adjuvant/antigen mixture preparation, b) immunization, c) antibody collection, and d) antigenicity assessment. a) adjuvant/antigen preparation: In all cases the antigen consisted of 1 mg of each of 4 snake venoms (4 mg of total antigen per bird): *Aqkistrodon contortrix, Aqkistrodon piscivorus, Crotalus atrox,* and *Crotalus adamanteus* (Sigma).

To prepare the Ribi adjuvant/venom antigen mixture, three volumes of the heat-inactivated antigen (heat inactivation was as described in Example 1) in PBS were mixed with one volume of Ribi LES+STM adjuvant (Ribi ImmunoChem Research Inc., Hamilton, Mont.) at 37° C. and vortexed to a milky emulsion before injection.

To prepare the Freund's adjuvant/venom antigen mixture, heat-inactivated venom was mixed in with CFA (GIBCO) in a relationship of 5:4 (adjuvant:antigen by volume) and emulsified to a firm consistency by passage through an antigen mixer made from two 18 gauge stainless steel hypodermic needles that had been brazed together.

To prepare the bentonite adjuvant/venom antigen mixture, one volume of native venom was mized with one volume of a sterile, 2% (w/v) bentonite (Sigma) suspension to adsorb the venom proteins to the particulate.

b) immunization: Six, (previously unimmunized) one-year old white leghorn hens (numbered for reference as #337, #339, #340, #353, #354, and #355) were immunized on Day zero. Two birds (#339, #354) received the Ribi adjuvant/antigen mixture. Two other birds (#337, #353) received the antigen with CFA. The remaining two birds (#340, #355) received the antigen absorbed to bentonite. The hens were injected subcutaneously in multiple sites (both sides of the abdomen, both breasts, and in both wings to involve more of the lymphatic system).

All of the birds were re-injected in the same manner with the same amount of antigen (prepared in the same way for each two bird group) on Days 14 and 21, with the exception of birds #337 and #353, which received antigen in IFA.

c) antibody collection: Antibody was extracted from the eggs as described in Example 1. Importantly, the method of extracting antibody from the eggs resulted in approximately 80% recovery of initial antibody recovery according to the following assay:

Yolks were blended with seven volumes of egg extraction buffer (0.01M Na phophate, 0.1M NaCl, pH 7.5 containing 0.01% $NaN_3$). Then a small volume of diluted yolk was further diluted seven-fold in egg extraction buffer, centrifuged at 9000xg for 10 minutes and the supernatant assayed for antibody activity by ELISA [see d) below]. PEG-purified material was compared with the crude yolk sample for antivenom activity.

Eggs were collected from bird #355 beyond Day 28 for later use; PEG-purified antibody from #355 eggs collected from days 31–45 is referred to as "PEG-purified 355" in Examples 13, 16, 25, and 27, below.

d) antigenicity assessment: The impact of the different adjuvants on the antigenicity of the venom was assessed on Day 28 eggs (stored intact at 4° C. until they were assayed on Day 40) by ELISA. To prepare for the ELISA, 96-well Nunc Immuno-Plates were coated overnight at 4° C. in a humidified chamber with 200 μl/well of the appropriate venom (in this case C. atrox) at a concentration of 2 μg/ml. The next day the wells were blocked with PBS containing 0.1% bovine serum albumin (BSA) for 2 hours at room temperature. To perform the ELISA, appropriately diluted antibody was added in PBS containing 0.1% BSA and the plates were incubated for 2 hours at room temperature. The plates were then washed three times with BBS (0.1 M boric acid, 0.025 M sodium borate, 1 M NaCl, pH 8.3) containing 0.1% Tween 20, twice with PBS containing 0.1% Tween, and twice with just PBS. Alkaline phosphatase-conjugated rabbit anti-chick IgG (Fisher) was diluted 1:500 in PBS containing 0.1% BSA, added to the plates, and incubated 2 hours at room temperature. The plates were washed as before, except Tris-buffered saline, pH 7.2, was substituted for PBS in the last wash, and p-nitrophenyl phosphate (Sigma) was added at 1 mg/ml in 0.05 M $Na_2CO_3$ pH 9.5, 10 mM $MgCl_2$. The plates were then evaluated either qualitatively by visual examination or quantitatively by reading at 410 nm on a Dynatech MR300 Micro ELISA reader approximately 30 minutes after the substrate was added.

The ELISA results from the Day 28 eggs showed good reactivity for all the birds (data not shown). However, no clear difference between the three adjuvants was apparent when evaluated qualitatively. Nonetheless, bentonite did cause a palpable abcess in one bird, consistent with its reported tendency to do so. P. A. Christensen, In: Snake Venoms (Springer-Verlag 1979), Chapter 20 (pp. 825–846). Bentonite also caused a decrease in the laying frequency of this bird.

In view of the cost of the RIBI mixture and the side-effects of the bentonite, the fact that Freund's adjuvant works just as well makes Freund's adjuvant a preferred adjuvant.

EXAMPLE 3

Booster immunizations with a cocktail of native venoms.

To optimize the response and increase the titer of antibody, further immunization was demonstrated. The example involved a) adjuvant/antigen mixture, b) immunization, c) antivenom collection, and d) antibody titer assessment. a) adjuvant/antigen mixture: since this example involved the use of immunized birds (contrast Examples 1 and 2), the venoms were not modified and were used in their native form. The venom mixture consisted of 0.5 mg each of Crotalus atrox and Crotalus adamanteus and 0.25 mg of B. atrox (Sigma). IFA was mixed with the venom mixture in a 5:4 volume ratio (adjuvant:antigen) and emulsified to a firm consistency by passage through an antigen mixer made from two 18 guage stainless steel hypodermic needles that had been brazed together. b) immunization: The six one-year old white leghorn hens of Example 2 (#337, #339, #340, #353, #354, and #355) were immunized on Day 49. All the birds received the same adjuvant/antigen mixture. As before, the hens were injected subcutaneously in multiple sites.

c) antibody collection: Antibody was collected from the eggs as described in Example 1.

d) antibody titer assessment: The impact of the Day 49 boost of native venom (including B. atrox for the first time) on antibody titer was assessed on Day 62 using Day 57–61 eggs (stored intact at 4° C. until they were assayed on Day 62) by ELISA as described in Example 2.

Figure 6:
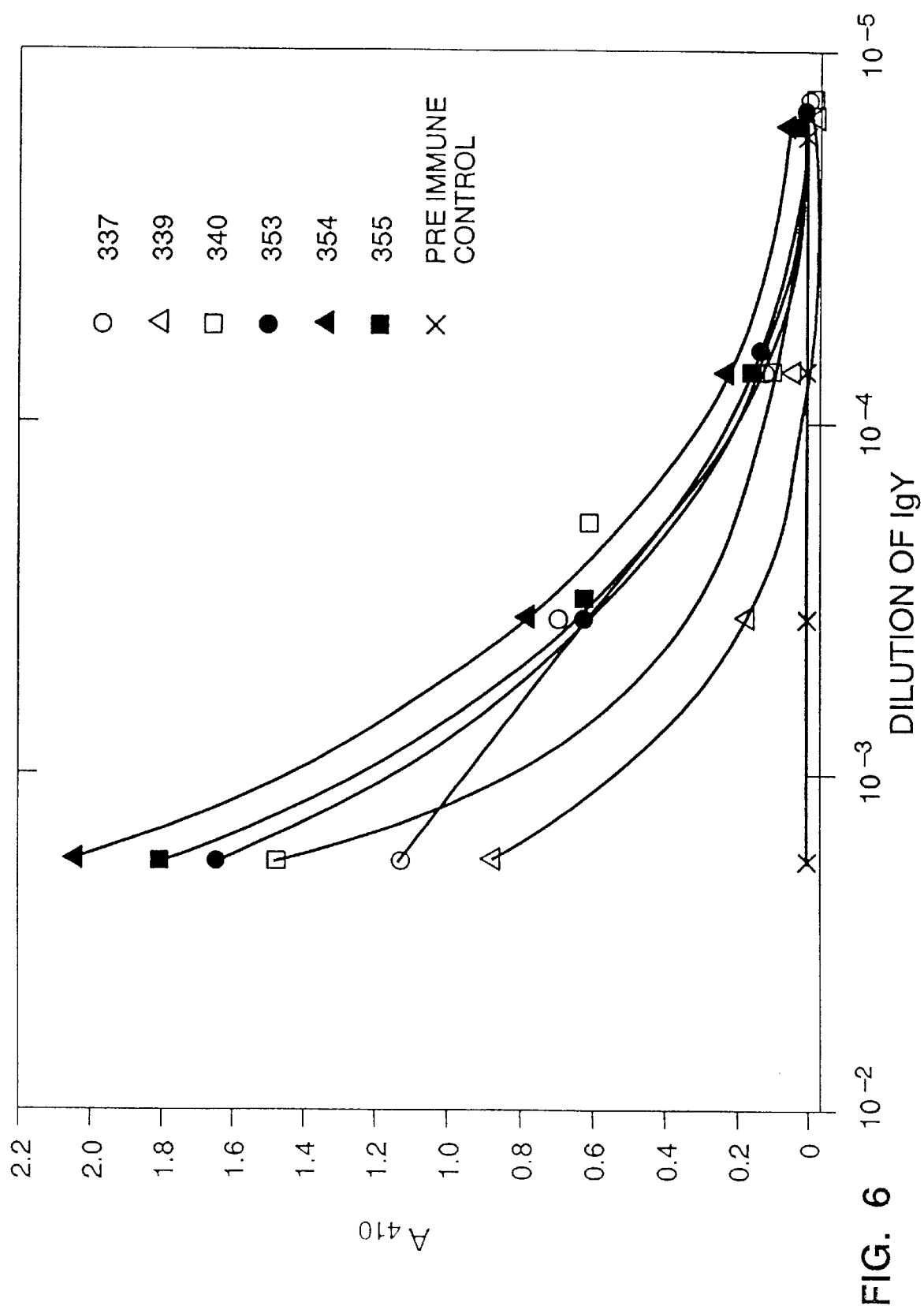
FIG. 6 shows the reactivity by ELISA of antivenom raised in different chickens against snake venom.

The results are shown in FIG. 6. Chicken #354 clearly had the highest titer as measured on Day 60 following the Day 49 boost. Interestingly, the bird with the lowest titer, #339, was previously immunized in the same manner as #354, suggesting that other factors may be involved in generating high titers than immune status. Importantly, all the birds show a significant titer as compared with the unimmunized control.

EXAMPLE 4

Response of a non-mammal to high doses of a cocktail of native venoms.

To optimize the response and increase the titer of antibody, further immunization was demonstrated. In this example, bird #354 was used exclusively. As in Example 3, the example involved a) adjuvant/antigen mixture, b) immunization, c) antivenom collection, and d) antibody titer assessment.

a) adjuvant/antigen mixture: As in Example 3, this example involved the use of immunized birds (contrast Examples 1 and 2). Therefore, the venoms were not modified and were used in their native form. The first venom mixture consisted of 0.5 mg each of Crotalus atrox and Crotalus adamanteus and 0.5 mg of B. atrox (Sigma). The second venom mixture consisted of 2.5 mg each of *Crotalus atrox* and *Crotalus adamanteus* (Sigma). The third venom mixture consisted of 10 mg each of *Crotalus atrox* and *Crotalus adamanteus* (Sigma). The first, second and third venom mixtures were mixed separately with IFA. The three adjuvant/antigen mixtures were mixed and emulsified as in Example 3.

b) immunization: Bird #354 was immunized on Day 72 with the first adjuvant/antigen mixture, on Day 86 with the second adjuvant/antigen mixture, and on Day 106 with the third adjuvant/antigen mixture. In all cases, the injections were made subcutaneously in multiple sites.

c) antibody collection: Antibody was extracted from yolks (as described in Example 1) of Day 58–60 eggs (hereinafter "PEG-purified Pool 1"; PEG-purified Pool 1 is used in Example 18, below), Day 74–81 eggs (hereinafter "PEG-purified Pool 2"); PEG-purified Pool 2 is used in Examples 16, 17, 18 and 19 below), Day 94–99 eggs (hereinafter "PEG-purified Pool 3"; PEG-purified Pool 3 is used in Examples 18 and 28 below) and Day 120–126 eggs (hereinafter "PEG-purified Pool 4"; PEG-purified Pool 4 is used in Examples 5, 14, 18, 23 and 26).

d) antibody titer assessment: The impact of the Day 72 boost of native venom (including an increased dose of *B. atrox*) on antibody titer was assessed on Day 81 using Pool 2 (the eggs were stored intact at 4° C. until they were extracted and assayed on Day 81) by ELISA (see Example 2 for general discription of ELISA). The results indicated a continuing increase in antibody titer.

Importantly, the previously immunized birds tolerated 20 mg of active native venom (3 times the dose required to kill an adult human on a body weight basis) with no apparent ill effects. This demonstrates that far greater immunizing doses (mg/kg) can be used than have been used in immunization schedules in the past. These higher doses allow for higher antivenom titers.

EXAMPLE 5

Duration of the high titer response to venoms in a non-mammal.

To optimize the duration of the response and increase the productive period of the laying hen, further immunization was demonstrated. In this example, bird #354 was used exclusively. As in Example 4, the example involved a) adjuvant/antigen mixture, b) immunization, c) antivenom collection, and d) antibody titer assessment.

a) adjuvant/antigen mixture: As in Example 4, this example involved the use of immunized birds. Therefore, the venoms were not modified and were used in their native form. The first venom mixture consisted of 2.5 mg. each of *Crotalus atrox* and *Crotalus adamanteus* (Sigma); the second venom mixture consisted of 5.0 mg. each of *C. atrox* and *C. adamanteus*; the third mixtures consisted of 10 mg. *C. atrox* and 5 mg. *C. adamanteus*; the fourth mixture consisted of 10 mg. *C. atrox* and 5 mg. *C. adamanteus*; the fifth mixture consisted of 15 mg. *C. atrox* and 10 mg. *C. adamanteus*. All five venom mixtures were mixed separately with IFA and the adjuvant/antigen mixtures emulsified as in Example 3.

b) immunization: Bird #354, which had been last immunized on day 106 (see Example 4), was immunized on day 300 with the first adjuvant/antigen mixture, on day 328 with the second adjuvant/antigen mixture, on day 356 with the third adjuvant/antigen mixture, on day 372 with the fourth adjuvant mixture, and on day 407 with the fifth adjuvant/antigen mixture. In all cases, the injections were made simultaneously in multiple sites.

c) antivenom collection: Antivenom antibody was extracted from the eggs as described in Example 1.

d) antibody titer assessment: The impact of these five boosts of native venom was assessed on day 422 using antibody from day 412–415 eggs ("day 422 prep" indicates the eggs were stored intact at 4° C. until antibody was PEG-purified and assayed on day 422) and compared in an ELISA (see Example 2) with PEG-purified Pool 4.

Figure 7:
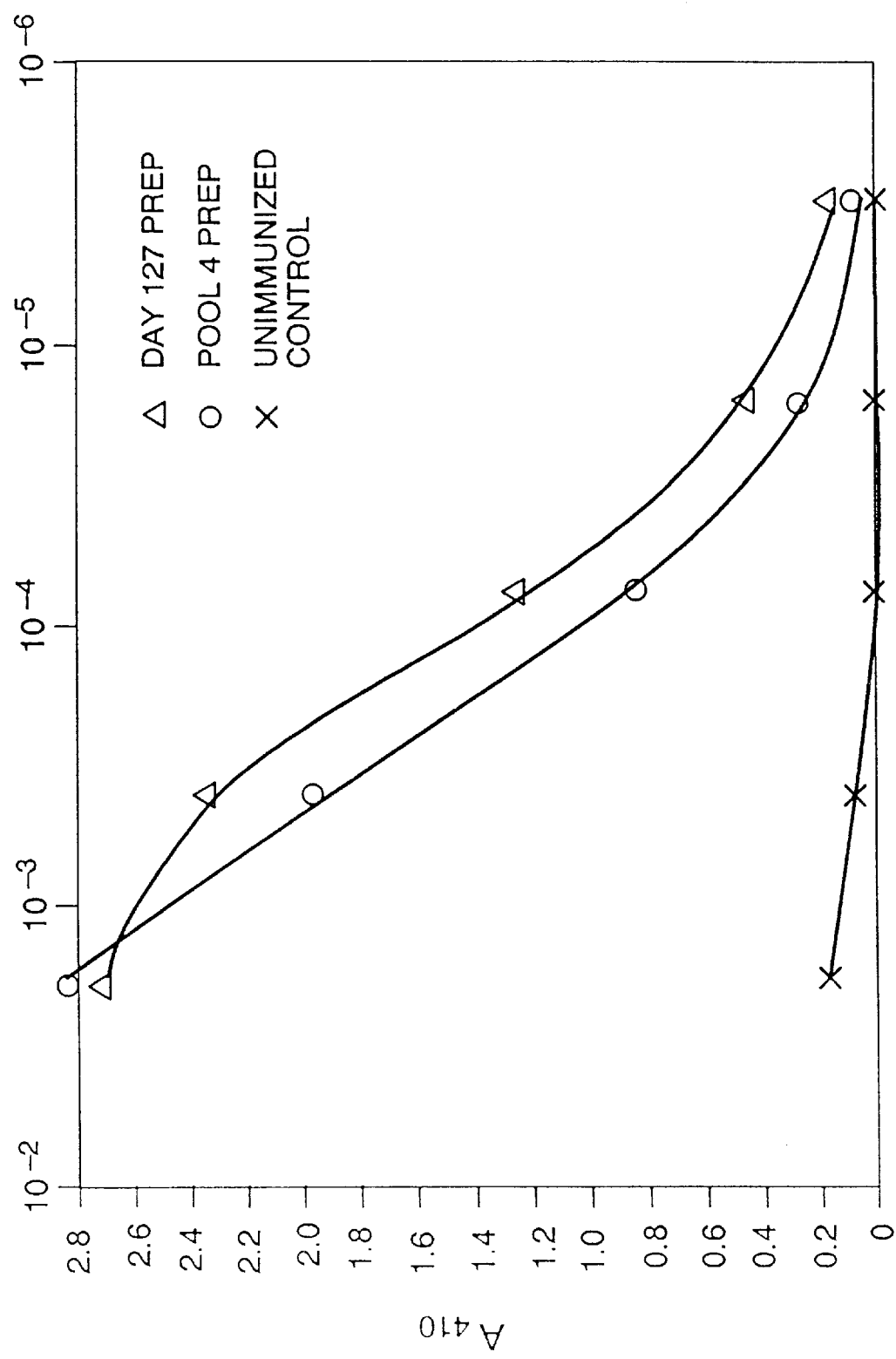
FIG. 7 shows the reactivity by ELISA of two preparations of antivenom raised in one chicken over three hundred days apart.

It can be seen (FIG. 7) that the response of the bird is comparable with both preparations (in terms of reactive antivenom per ml). Thus, a bird, that has not been immunized for almost two hundred days, can be re-immunized with venom in a second immunization program such that the response is equivalent to the response observed after the initial immunization program. Clearly, birds are useful for more than one year for antivenom production.

EXAMPLE 6

Covalent attachment of whole snake venom to cyanogen bromide-activated agarose matrix.

In this example, the coupling efficiency of Sepharose 4B (Pharmacia) (hereinafter "resin I"), was demonstrated using snake venom as antigen. *C. atrox* venom was diluted in PBS (pH 7.2) at a concentration of 10 mg/ml. In a chemical hood, Resin I was washed with 5 volumes of chilled distilled $H_2O0$, suspended in an equal volume of 2.5M potassium phosphate buffer (pH 12.2) in a beaker immersed in an ice bath, and stirred gently. In a separate vessel in the same chemical hood, 1 gram of CNBr (Alrich) was dissolved in 1 ml of acetonitrile per 10 ml of gel to be coupled. Thereafter, the CNBr solution was added to the gently stirring solution of resin I over a period of two minutes. The mixture (hereinafter "activated resin I") was continually stirred for an additional eight minutes and then washed in a scintered glass funnel with 10 volumes of cold distilled $H_2O$ followed by 10 volumes of cold PBS. The venom solution was then added to the activated resin I in the funnel and the mixture (hereinafter "antigen matrix") was agitated overnight. The uncoupled filtrate was collect from the funnel and measured ($A_{280}$). Coupling efficiency was calculated as the amount of coupled protein ($A_{280}$ units) divided by the total starting amount of protein ($A_{280}$). The results showed that the coupling efficiency of activated resin I was in the range of 90–95%. Thus almost 10 mg of venom protein was bound per ml of resin.

For later use, the antigen matrix was suspended in an equal volume of 1M ethanolamine-10mM Tris-HCl (pH 8.5) for 2 hours at 4° C. to block remaining protein-reactive sites. The antigen matrix was then washed with PBS containing 0.02% sodium azide and stored at 4° C.

EXAMPLE 7

Covalent attachment of whole snake venom to an aldehyde-activated polyacrylamide/agarose matrix.

In this example, the coupling efficiency of the aldehyde-activated, polyacrylamide/agarose resin, Ultrogel AcA 22 (IBF) (hereinafter "activated resin II"), was demonstrated. *C. atrox* venom was diluted in PBS (pH 7.2) at a concentration of 10 mg/ml. Activated Resin II was washed with 10 volumes of distilled $H_2O$ and then with 2.5 volumes of 0.5M $NaPO_4$ (pH 7.0). Resin II was then added in an equal volume to the venom solution. The mixture (hereinafter "antigen matrix") was split into two equal volumes. One was agitated for 18 hours at 4° C. The other was agitated for 18 hours at room temperature. Both antigen matrix solutions were washed with PBS on a glass funnel. The filtrates were collected and coupling efficiency was calculated as in Example 6. The antigen matrix agitated at 4° C. showed 52% coupling yield and the antigen matrix agitated a room temperature showed 62% coupling yield. Thus, 5–6 mg of venom protein per ml of matrix was coupled using activated Resin II.

For later use, protein reactive sites were blocked in 1M ethanolamine-10mM Tris-HCl (pH 8.0) at 4° C. for 3 hours. The antigen matrix was then washed and stored in PBS containing 0.02%.

EXAMPLE 8

Covalent attachment of whole snake venom to an aldehyde-activated agarose matrix.

In this example, the coupling efficiency of the aldehyde-activated resin, ACTIGEL A (Sterogene) (hereinafter "activated resin III"), was demonstrated. *C. atrox* venom was dissolved in PBS (pH 7.2) at a concentration of 10 mg/ml. Activated Resin III was washed with 3 volumes of PBS and added (in equal volume) to the venom solution. Thereafter, 1/10 volume of 1M sodium cyanoborohydride (Aldrich) was added. The mixture (hereinafter "antigen matrix") was then split into two equal volumes. One was agitated for 4 hours at room temperature. The other was agitated overnight at 4° C. Both antigen matrix mixtures were washed on glass funnels with PBS. The filtrate was collected and coupling efficiency was calculated as in Example 6. The results showed that coupling efficiency of activated Resin III is in the range of 80 to 90%. The antigen matrix was stored in PBS containing 0.02% sodium azide at 4° C.

EXAMPLE 9

Covalent attachment of whole snake venom from a second species to an aldehyde-activated agarose matrix.

In this example, the coupling efficiency of the aldehyde-activated resin, ACTIGEL A (Sterogene) (hereinafter "activated resin III"), was studied with another venom. *C. durissus terrificus* venom was dissolved in PBS (pH 7.2) at a concentration of 5 mg/ml. Activated Resin III was washed with 3 volumes of PBS and added (in equal volume) to the venom solution. Thereafter, 1/10 volume of 1M sodium cyanoborohydride (Aldrich) was added. The mixture (hereinafter "antigen matrix") was agitated overnight at 4° C. The antigen matrix was then washed on a glass funnel with PBS. The filtrate was collected and coupling efficiency was calculated as in Example 6. The results showed that coupling efficiency of activated Resin III was 95%. The antigen matrix was stored in PBS containing 0.02% sodium azide at 4° C..

EXAMPLE 10

Covalent attachment of whole snake venom from a third species to an aldehyde-activated agarose matrix.

In this example, the coupling efficiency of the aldehyde-activated resin, ACTIGEL A (Sterogene) (hereinafter "activated resin III"), was studied with another venom. *C. adamanteus* venom was dissolved in PBS (pH 7.2) at a concentration of 10 mg/ml. Activated Resin III was washed with 3 volumes of PBS and added (in equal volume) to the venom solution. Thereafter, 1/10 volume of 1 M sodium cyanoborohydride (Aldrich) was added. The mixture (hereinafter "antigen matrix") was agitated for 4 hours at room temperature. The antigen matrix was then washed on a glass funnel with PBS. The filtrate was collected and coupling efficiency was calculated as in Example 6. The results showed that coupling efficiency of activated Resin III was 78%. The antigen matrix was stored in PBS containing 0.02% sodium azide at 4° C.

EXAMPLE 11

Covalent attachment of a mixture of whole snake venoms to an aldehyde-activated agarose matrix.

In this example, the coupling efficiency of the aldehyde-activated resin, ACTIGEL A (Sterogene) (hereinafter "activated resin III") was studied with a cocktail of four venoms. *C. atrox, C. adamanteus, A. piscivorus* and *A. contortrix* venoms were dissolved together in PBS (pH 7.2) with each venom at a concentration of 10 mg/ml. Activated resin III was washed with 6 volumes of PBS and added (in equal volume) to the venom solution. Thereafter, 1/10 volume of 1M sodium cyanoborohydride (Aldrich) was added. The mixture (hereinafter "antigen matrix") was then agitated for seven hours at room temperature and left overnight at 4° C. The antigen matrix was then washed on a glass funnel with PBS. The filtrate was collected and coupling efficiency was calculated as in Example 6. The results showed that coupling efficiency of activated resin III was 54%. The antigen matrix was stored in PBS containing 0.02% sodium azide at 4° C.

EXAMPLE 12

Elution of specifically-bound antibodies from an affinity matrix with different eluents.

In this example, the elution efficiency of various eluents on chicken antibody is demonstrated. Chicken antibody is generated, collected and extracted from eggs as described in Example 1. Resin I is used to prepare an antigen matrix as in Example 6. Five eluents are studied in successive elutions. Between each elution, the antigen matrix is washed with TBS, the eluate is collected and measured ($A_{280}$), the antigen matrix is stripped of remaining antibody with 4M guanidine-HCl, this stripped antibody is collected and measured ($A_{280}$), the antigen matrix is washed and the same amount of PEG-purified, chicken antibody (diluted in egg extraction buffer) is loaded on the antigen matrix at a flow rate of 1 ml per min, and washed successively with several bed volumes of PBS, BBS-Tween (0.1 M boric acid, 0.025 M sodium borate, 1 M NaCl, 0.1% (v/v) Tween 20 pH 8.3), and PBS until the effluent is free of protein ($A_{280}$).

In the first elution, bound chicken antibody is eluted immediately with 4M Guanidine-HCl (pH 8.0) and the antigen matrix is washed with PBS. The eluate is collected and measured ($A_{280}$). The elution efficiency of 4M guanidine-HCl is functionally defined as 100%; there is no antibody remaining on the column that can be further eluted with 4M guanidine-HCl. Elution efficiencies calculated for other eluents (see below) are relative efficiencies using 4M guanidine-HCl as 100%.

The same antigen matrix is reacted with the same amount of PEG-purified chicken antibody and washed as discussed above. Bound chicken antibody is eluted immediately with 2M Guanidine-HCl (ph 8.0) and the antigen matrix is washed with PBS. The eluate is collected and measured ($A_{280}$). Relative elution efficiency is calculated as the total $A_{280}$ units collected here divided by the total $A_{280}$ units collected for 4M guanidine-HCl.

The same antigen matrix is reacted a third time with the same amount of PEG-purified chicken antibody and washed as above. Bound chicken antibody is immediately eluted with 8M Urea (ph 8.0) and the antigen matrix is washed with PBS. The eluate is collected and measured ($A_{280}$). Relative elution efficiency is calculated as above.

The same antigen matrix is reacted a fourth time with the same amount of PEG-purified chicken antibody and washed as above. Bound chicken antibody is immediately eluted with 4M Urea (ph 8.0) and the antigen matrix is washed with PBS. The eluate is collected and measured ($A_{280}$). Relative elution efficiency is calculated as above.

The same antigen matrix is reacted a fifth time with the same amount of PEG-purified chicken antibody and washed as above. Bound chicken antibody is immediately eluted with 0.5 M diethylamine (pH 11.5) and the antigen matrix is washed with PBS. The eluate is collected and measured ($A_{280}$). Relative elution efficiency is calculated as the percent of maximum yield (see above). The efficiency of elution for the five eluents is shown in Table 2. It can be seen that 4M Urea and 0.5M diethylamine are poor eluents; they fail to remove all the bound chicken antibody. The other three eluents remove 90% or more of the bound antibody.

TABLE 2

Efficiency of Eluents

| Eluent | Efficiency |
| --- | --- |
| 4M Guanidine-HCl, pH 8.0 | 100 |
| 2M Guanidine-HCl, pH 8.0 | 90 |
| 8M Urea, pH 8.0 | 100 |
| 4M Urea, pH 8.0 | 65 |
| 0.5M diethylamine, pH 11.5 | 38 |

EXAMPLE 13

Elution of non-mammalian antivenom antibodies from an aldehyde-activated agarose venom antigen matrix using guanidine.

In this example, chicken antibody was eluted with 4M guanidine-HCl (ph 8.0) from an antigen matrix made up with resin I. Approximately 10 mg *C. atrox* venom was coupled per ml of CNBr-activated Sepharose 4B as in Example 6 above. 100 ml of PEG-purified 355 (see Example 2) was loaded on a 5 ml antigen matrix at a flow rate of 1 ml per minute. The flow through ("355 flow through") was collected and the antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted immediately with 4M guanidine-HCl (ph 8.0) and the antigen matrix was washed with PBS. The eluate ("Resin I purified 355") was collected and measured ($A_{280}$) and found to contain 125 μg of antibody per ml of PEG-purified 355 applied.

EXAMPLE 14

Elution of non-mammalian antivenom antibodies from an aldehyde-activated agarose venom antigen matrix with a non-denaturing eluent.

In this example, chicken antibody was eluted from an aldehyde-activated resin with 4M guanidine-HCl (ph 8.0). 5 mg *C. atrox* venom was coupled per ml of ULTROGEL AcA 22 as in Example 7 above. 5 mls of PEG-purified Pool 4 (9 mg/ml total protein) antibody was loaded on a 3 ml antigen matrix at a flow rate of 1 ml per minute. The flow through ("Pool 4/ultro flow through") and the antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was immediately eluted with 4M guanidine-HCl (ph 8.0) and the antigen matrix was washed with PBS. The eluate ("ultro-purified Pool 4") was collected and measured ($A_{280}$) and found to contain 742 μg of antibody per ml of PEG-purified Pool 4 applied.

EXAMPLE 15

Increasing the elution efficiency of a non-denaturing eluent by increasing column residence time.

In this example, the elution efficiency of a recently developed elution medium on an aldehyde-activated resin was demonstrated. 10 mg *C. atrox* venom was coupled per ml of ACTIGEL as in Example 8 to make the antigen matrix. 10 mls of PEG-purified 355 (see Example 2) was loaded on a 5 ml antigen matrix at a flow rate of 1 ml per minute. The flow through ("355 flow through") was collected and the antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted with ACTISEP Elution Medium (Sterogene) according to the manufacturer's instructions, i.e. eluent was applied in a manner such that it was in contact with the antigen matrix ("residence time") for 30 minutes. The eluate ("actigel/actisep-purified 355") was collected and measured ($A_{280}$), and the antigen matrix was washed with TBS. Remaining antibody on the antigen matrix was eluted with 4M guanidine-HCl. This eluate ("actigel/guano-purified 355") was collected and measured ($A_{280}$), and the antigen matrix was then washed with PBS. Elution efficiency was calculated as the percent of the total antibody eluted by ACTISEP and was found to be 26% (400 μg total protein). The remaining 74% (1.5 mg total protein) was eluted by quanidine.

EXAMPLE 16

Further increasing the elution efficiency of a non-denaturing eluent.

In this example, the elution efficiency of ACTISEP on an activated aldehyde resin was optimized by a modified protocol; the residence time was increased to 2 hours (Assay 1) and then to 2 hours and 45 minutes (Assay 2).

Assay 1

The cocktail matrix of Example 11 (above) was used to immunoaffinity purify 10 mls of PEG-purified 355 (see Example 2). The antibody was applied as in Example 15 except that the residence time was increased to 90 minutes (time 0 is just before the eluent is detectable in the effluent of the column). The eluate was collected and measured ($A_{280}$), the antigen matrix was stripped of remaining antibody with 4M guanidine-HCl, and this stripped antibody was collected and measured ($A_{280}$). Elution efficiency was calculated as in Example 15 and found to be 47%.

Assay 2

The *C. atrox* matrix of Example 8 was used to immunoaffinity purify 10 mls of PEG-purified Pool 2 (see Example 4). The antibody was applied as in Example 15 except that the residence time was increased to 2 hours and 45 minutes (time 0 is just before the eluent is detectable in the effluent of the column). The eluate was collected and measured ($A_{280}$), the antigen matrix was stripped of remaining antibody with 4M guanidine-HCl, and this stripped antibody was collected and measured ($A_{280}$). Elution efficiency was calculated as in Example 15 and found to be 73%.

Figure 8:
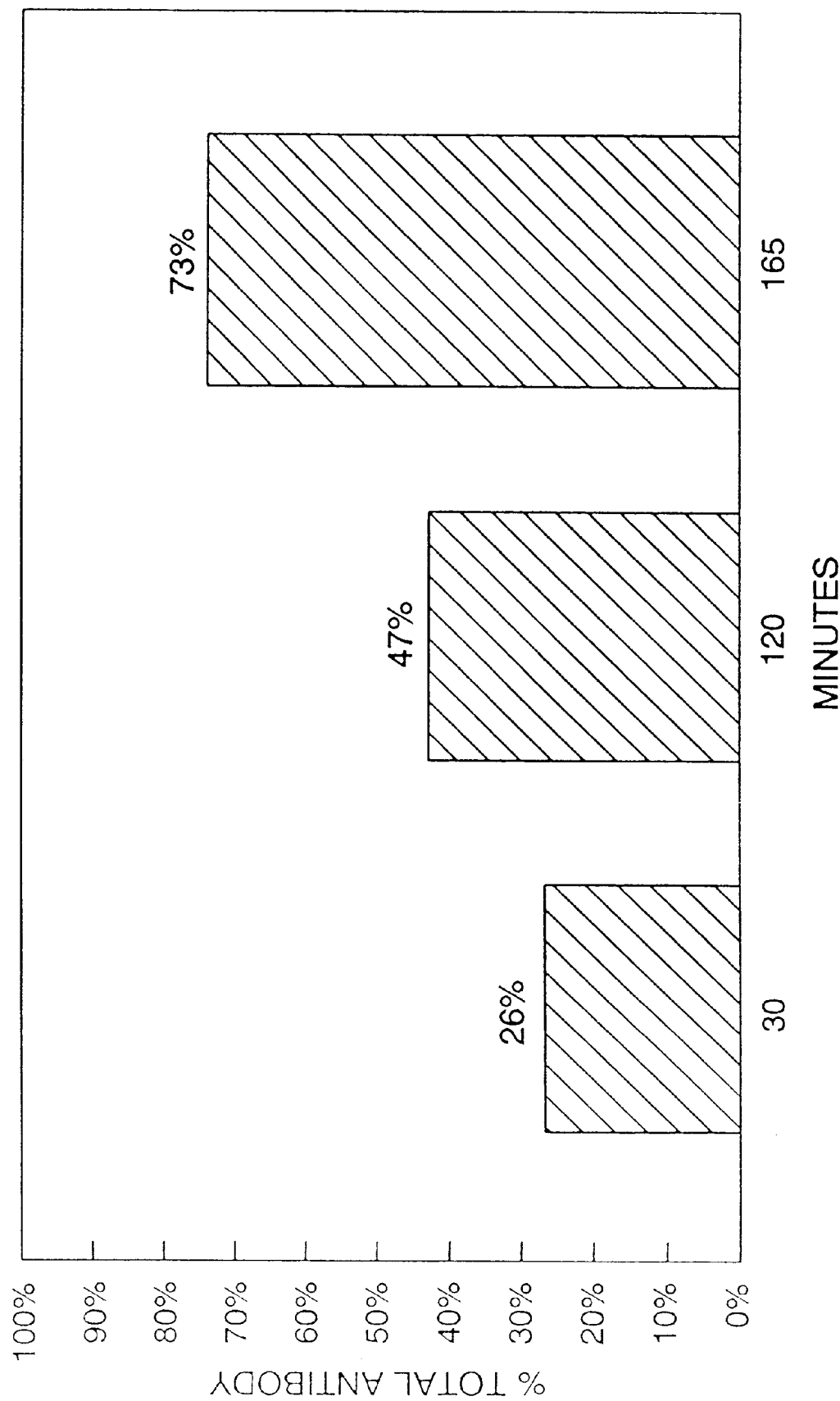
FIG. 8 shows the increase in elution efficiency observed with increased residence time of a non-denaturing eluent.

The results of this example are shown in FIG. 8 (the results of Example 15 are plotted in FIG. 8 for purposes of comparison). The efficiency of antibody elution was increased to 47% with 90 minutes of residence time and to 73% with 2 hours and 45 minutes of residence time.

EXAMPLE 17

Optimization of elution efficiency.

In this example, the elution efficiency of ACTISEP on an activated aldehyde resin was optimized by a further modified protocol. 10 mg C. atrox venom was coupled per ml of ACTIGEL to make an antigen matrix as in Example 8 above. Affinity purification was carried out as in FIG. 9. 25 mls of PEG-purified Pool 2 (see Example 4) was loaded on the antigen matrix at a flow rate of 1 ml per minute. The antigen matrix was washed and the bound antibody eluted with ACTISEP as in Example 15 except the residence time was increased by stopping the flow of the column at the point where the peak of eluted protein concentration was reached. As before, the antigen matrix was washed with TBS, the eluate was collected and measured ($A_{280}$), the antigen matrix was stripped of remaining antibody with 4M guanidine-HCl, this stripped antibody was collected and measured ($A_{280}$), the antigen matrix was washed with buffer and stored at 4° C. for later use.

Figure 9:
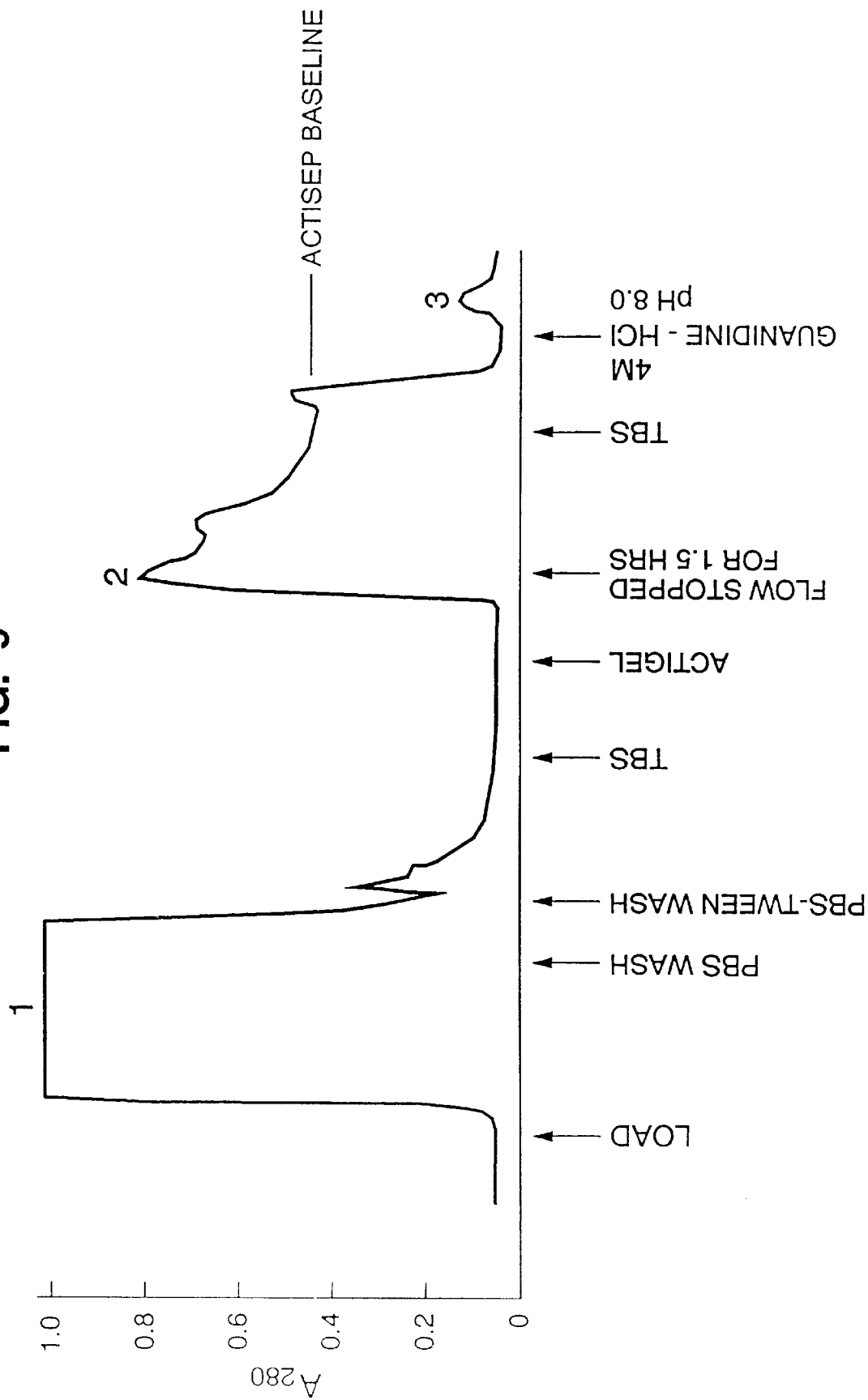
FIG. 9 shows an immunoaffinity purification profile for a preferred embodiment of the method of the present invention.

The peaks in FIG. 9 are numbered to correspond to chicken antibody flow through (peak 1), non-specifically bound antibody (peak 2), ACTISEP eluted antibody (peak 3) (note ACTISEP baseline, i.e. absorbance attributable to the eluent alone), and 4M guanidine-stripped antibody (peak 4). Importantly, by stopping the flow of the column at the point where the peak of eluted protein concentration was reached, the efficiency of antibody elution could be further increased to 89% (efficiency calculated as in Example 14) for an ACTISEP elution of 128 µg of antibody per ml of PEG-purified antibody applied. An additional 16 µg of antibody (per ml of PEG-purified antibody applied) was recovered with quanidine (for a total of 144 µg/ml of specific antibody per ml of PEG-purified antibody applied).

EXAMPLE 18

The increase in titer of antivenom antibody with further immunization.

In this example, chicken antibody was quantitatively immunoaffinity purified from an aldehyde-activated resin to show increasing antibody titer with increasing immunization. 10 mg C. atrox venom was coupled per ml of ACTIGEL A as in Example 8 above. The four, chicken #354, PEG-purified pools described in Example 4 were used. After each elution, the antigen matrix was washed with TBS, the eluate was collected and measured ($A_{280}$), the antigen matrix was stripped of remaining antibody with 4 M guanidine-HCl, this stripped antibody was collected and measured $A_{280}$, the antigen matrix was washed and a new pool of chicken antibody was loaded to the antigen matrix. Each pool (5–20 mls) was loaded on the same 5 ml antigen matrix at a flow rate of 1 ml per min, and washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted immediately with 4 M guanidine-HCl (pH 8.0) and the antigen matrix was washed with PBS. The eluates were collected and measured ($A_{280}$) for amounts of specific antibody. The results are shown Table 3. The results demonstrate that the C. atrox-specific antibody titer increased nearly ten-fold over a period of approximately 60 days due to further immunizations.

TABLE 3

| Antivenom Antibody Titers | |
|---|---|
| #354 Pool | Titer (µg Ab/ml egg yolk) |
| 1 | 98 |
| 2 | 144 |
| 3 | 600 |
| 4 | 905 |

EXAMPLE 19

Purity of mammalian and non-mammalian antivenoms immunoaffinity purified on an aldehyde-activated whole venom antigen matrix.

In this example, the purity of antivenoms before and after immunoaffinity purification was demonstrated. 10 mg C-atrox venom was coupled per ml of ACTIGEL A as in Example 8. 2 mls of unpurified horse antivenom (Wyeth; log #M878035) containing 210 mg/ml (total 420 mg) were applied to a 5 ml antigen matrix, the flow-through was washed through the column initially with PBS and saved for further. analysis, the matrix was then washed with BBS-Tween until the effluent was substantially free of protein ($A_{280}$) and then with PBS. Bound antibody was eluted immediately with 4M guanidine, collected and measured ($A_{280}$) after complete dialysis. The antigen matrix was then re-equilibrated with PBS. This eluate contained 19.7 $A_{280}$ units of antibody.

The flow-through was then re-applied to the 5 ml C. atrox venom antigen matrix and washed and eluted as described above in order to affinity purify any antibody not isolated in the first pass above. The guanidine-HCl eluate from the second pass contained only 3.4 $A_{280}$ units of antibody, indicating that approximately 85% of the C. atrox specific antibody was purified in the first pass. Importantly, the 23.1 $A_{280}$ units (16.5 mg) of total antibody purified from both passes represents only 3.7% (16.5 mg/420 mg) of the total $A_{280}$ units of protein present in the crude horse antivenom, indicating that 95% or more of the protein present in the antivenom does not react with C. atrox venom. This is in contrast with the pool #4 affinity purified chicken anti-C. atrox described in Example 18 where 905 µg/ml of a 9 mg/ml PEG prep or 10% of the total protein was C. atrox-specific antibody. Because of the higher concentration of antivenom antibodies and increased protein homogeneity (see below) of the chicken IgY, we contemplate that this antivenom, without affinity purification, is useful for passive immunization (as well as in vitro analytical work).

To examine the composition of the crude and affinity purified antivenoms, analytical SDS-PAGE was performed on antivenoms at different stages of purification. A fresh 2 ml sample of crude horse antivenom (Wyeth; lot #M878035) was applied to the same 5 ml C. atrox venom antigen matrix described above and the column washed with PBS, BBS-Tween, and TBS until the effluent was substantially free of protein ($A_{280}$). Bound antibody was eluted with ACTISEP using the optimized protocol in Example 17 and collected and measured after complete dialysis. The antigen matrix was then washed with TBS and the remaining antibody eluted immediately with 4M guanidine-HCl, collected and measured ($A_{280}$) after complete dialysis. The antigen matrix was then re-equilibrated by washing with PBS. Samples of the unpurified, flow-through, ACTISEP and guanidine fractions were retained for further analysis.

Figure 10:
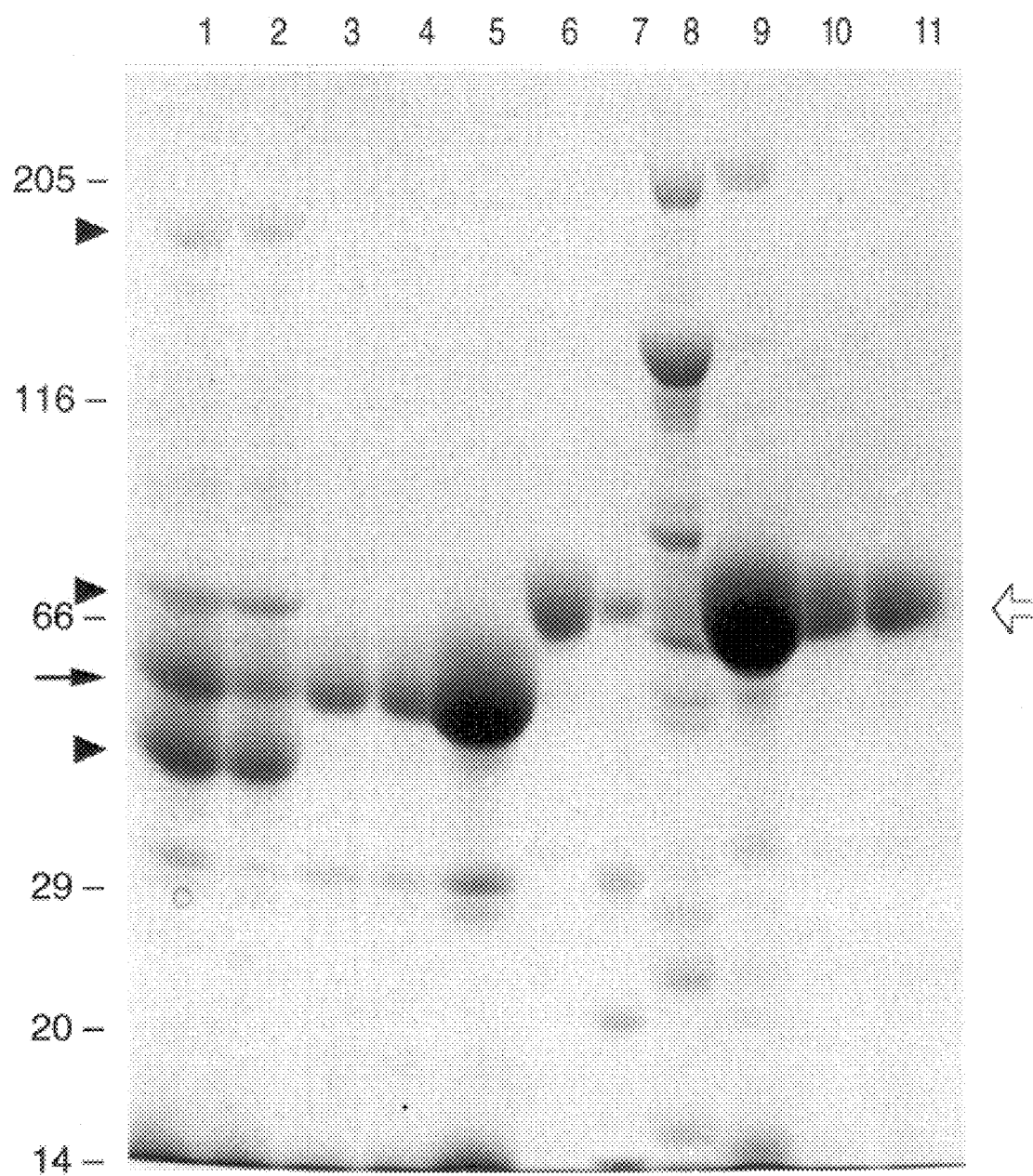
FIG. 10 shows SDS-PAGE analysis of chicken and horse antivenoms.

Samples from the affinity purification of 25 mls of Pool 2 described in Example 17 were analyzed along with the horse antivenom samples by SDS-PAGE on a 10% reducing gel (FIG. 10). Comparison of 100 μg of the applied crude horse antiserum (Lane 1) with 100 μg of the crude horse antiserum flow through (Lane 2) revealed no detectable differences in composition. However, 30 μg (Lane 3) and 150 μg (Lane 5) of the guanidine-eluted horse antibody and 30 μg of the ACTISEP-eluted horse antibody (Lane 4) all exhibited a pattern of fewer polypeptides; the predominant polypeptide was found to be a 55,000 dalton band (size is estimated from molecular weight markers in Lane 7) corresponding to the relative mobility of the heavy chain of horse immunoglobulin. None of the higher molecular weight polypeptides present in the crude antivenom (Lanes 1 and 2) were found in the eluates (Lanes 3, 4 and 5), indicating that these high molecular weight proteins are not immunoglobulin and are removed during affinity purification. Densito-metric scanning of gel lane 1 indicated that no more than 37% of the total protein present in the crude Wyeth antivenom was immunoglobulin (data not shown). Since 3.7% of the total protein is venom-reactive (see above), it follows that 10% (3.7%/37%) of the total horse immunoglobulin is venom-reactive.

Similarly, 30 μg of the PEG-purified, chicken antibody flow through (Lane 9) contains high molecular weight polypeptides that are not recovered in the guanidine (Lane 10) and ACTISEP (Lane 11) eluates. The bands associated with these eluates (Lanes 10 and 11) correspond to the polypeptides of a commercial (Cappel) sample of pure chicken immunoglobulin (Lane 6). (The proteins from unpurified chicken yolks are shown in Lane 8). These results demonstrate that: i) the PEG-purified chicken antivenom (Lane 9) is less heterogenous than the crude horse antivenom (Lane 1), in that far fewer non-immunoglobulin proteins are present in the PEG-purified chicken IgY preparation (greater than 90% of the total PEG-purified protein is immunoglobulin and, given that 10% of the protein is venom reactive, it follows that 11% (10%/90%) of the immunoglobulin is venom-reactive); ii) the affinity purification removes substantially all of the non-immunoglobulin protein from the crude antivenoms (greater than 99% of the protein in these preparations is immunoglobulin); and iii) both the ACTISEP and guanidine eluates containing the horse and chicken antivenoms are essentially pure (greater than 99%) antigen-specific immunoglobulin. Table 4 summarizes the immunoglobulin content, purity and reactivity of the horse and chicken antivenoms at different stages of purification. Note that before affinity purification (see "crude horse" and "PEG IgY"), less than 50% of the antivenom immunoglobulin ("Ig") is venom-reactive. After affinity purification ("AP"), greater than 50% of the antivenom immunoglobulin ("Ig") is venom-reactive.

TABLE 4

| Immunoglobulin Content, Purity & Reactivity | | | |
|---|---|---|---|
| Antivenom | % Ig | % reactive protein | % reactive Ig |
| Crude Horse | 37 | 3.7 | 10 |
| AP Horse | >99 | >99 | >99 |
| PEG: IgY | >90 | 10 | 11 |
| AP IgY | >99 | >99 | >99 |

EXAMPLE 20

Spectrum of reactivity of horse antivenom before and after affinity purification on a C. atrox antigen matrix.

In this example, the ability of a C. atrox antigen matrix to bind and purify the spectrum of antibodies present in a crude polyvalent horse antivenom was examined. 2 ml of Wyeth Polyvalent Crotalid antivenom (lot #M878035), raised against C. atrox, C. adamanteus, B. atrox, and C. durissus terrificus venoms, was applied to a 5 ml C. atrox Actigel A antigen matrix prepared as described in Example 8. The flow-through was collected, the column washed, and antibody eluted as described in Example 17. The flow-through fraction was applied to two more C. atrox-Actigel A antigen matrices in succession in order to remove as much C. atrox reactive antibody as possible. The total amount of C. atrox reactive antibody, calculated from the $A_{280}$ of all three column eluates, was 7.5 mg per ml of this lot of Wyeth antivenom.

To assess the spectrum of activity of the purified C. atrox-reactive antibody, and to compare it with the activity of both the crude antivenom and the non-C. atrox reactive fraction of the antivenom that flowed through all three C. atrox matrices, we examined antibody reactivity by ELISA using the four original venoms used for immunization as antigens (see above). 96-well Nunc Plates were coated overnight at 4° C. in a humidified chamber with 200 μl/well of the appropriate venom dissolved in PBS at 5 μg/ml. The venoms used in this example were C. atrox, C. adamanteus, C. durissus terrificus, and B. atrox (Sigma). The next day the wells were blocked with PBS containing 0.1% bovine serum albumin for 2 hours at room temperature. Antibodies to be tested for binding to each of the four venoms were diluted in PBS containing 2% (v/v) normal goat serum (GIBCO). In order to directly compare the crude Wyeth antivenom, the antigen matrix flow-through fraction, and the affinity purified anti-C. atrox with respect to their reactivities, the antibodies were diluted in such a way as to normalize i) the volume of the flow-through fraction with the volume of the crude Wyeth antivenom starting material, and ii) the concentration of C. atrox-specific antibodies in the crude antivenom, i.e., since the crude antivenom contain 7.5 mg/ml of C. atrox-specific antibody, to compare the unpurified crude antivenom to a set concentration of purified antibody dilutions were made of the crude material such that the concentrations of C. atrox-specific antibody were the same (e.g., 2.5 μg/ml of specific antibody is equivalent to a 1:3000 dilution of crude antivenom).

200 μl/well of four 3-fold serial dilutions of each antibody and a normal unimmunized horse serum control (Sigma) were incubated for 2 hours at room temperature. The plates were then washed three times with BBS containing 0.1% Tween 20, twice with PBS-Tween 20, and twice with PBS.

Alkaline phosphatase-conjugated goat anti-horse IgG (Fisher Biotech) was diluted 1:500 in PBS containing 2% (v/v) normal goat serum, added to the plates, and incubated 2 hours at room temperature. The plates were washed as before, except Tris-buffered saline was substituted for the last wash, and p-nitrophenyl phophate was added and the hydrolysis of the substrate measured at 410 nm as described in Example 2. The ELISA results of the

TABLE 5

Reactivity of Purified Horse Antivenom

| | % of initial reactivity with | | | |
|---|---|---|---|---|
| | C. atrox | C. adamanteus | B. atrox | C. durissus terrificus |
| Starting Material (crude Wyeth) | 100 | 100 | 100 | 100 |
| C. atrox Flow Through | 11 | 7 | 21 | 49 |
| C. atrox affinity purified | 88 | 97 | 85 | 40 | relative reactivity of the crude horse antivenom, the C. atrox antigen matrix flow-through, and the affinity purified anti-C. atrox antibody at a concentration of antibody that fell within the linear range of the ELISA (the normal horse serum control values have been subtracted) on each of the four venoms are shown in Table 5. The results show that affinity purification of this antivenom with the C. atrox antigen matrix recovers the majority of the antibody activity against three of the original venoms used for immunization, C. atrox, C. adamanteus, and B. atrox, indicating that these three venoms contain many similar antigens. However, the fourth venom, C. durissus terrificus, is not as strongly reactive with the C. atrox purified antibody. In fact, the majority of the C. durissus terrificus reactivity by this assay still remains in the flow-through fraction from the C. atrox antigen matrix. These examples demonstrate the existence of at least two antibody populations in the crude Wyeth antivenom, one that is polyvalent and reactive with C. atrox and the other three venoms, and one that is C. durissus terrificus reactive but not C. atrox-reactive (C. durissus terrificus monovalent).

EXAMPLE 21

Identification and purification of two monovalent antivenon antibody subpopulations and one polyvalent subpopulation in a horse antivenom by sequential imunoaffinity chromatography.

In this example, the reactivity and cross-reactivity of different subpopulations of antibodies derived from the Wyeth antivenom were examined in order to determine their valency. In addition, a means is demonstrated for purifying two or more monovalent subpopulations of antivenom antibodies by affinity chromatography of whole venom over successive antigen matrices composed of antigenically distinct venoms.

In Example 20, it was demonstrated that the antivenom fraction that did not bind to the C. atrox antigen matrices contained a large fraction of the original C. durrisus terrificus venom reactivity of the crude venom. To purify, quantitate, and analyze this subpopulation of antibodies, ½th of the flow-through fraction from three successive C. atrox antigen matrices was applied to a 3 ml C. durissus terrificus Actigel A antigen matrix prepared as described in Example 9. The flow-through fraction was saved, the matrix washed, and antibody eluted with 4 M guanidine-HCl, collected, and measured ($A_{280}$) as described in Example 13. The results showed that there exists approximately 1.2 mg of C. durissus-reactive antibody per ml of Wyeth antivenom that will not bind to a C. atrox antigen matrix. This is the C. durissus terrificus—specific monovalent antibody subpopulation. To examine the efficiency of the C. durissus terrificus antigen matrix at isolating the C. durissus terrificus—reactive antibody and to examine the activity of the affinity purified anti-C. durissus terrificus antibody, an ELISA was performed to assess the reactivity and cross-reactivity of the original Wyeth antivenom, the flow-through fraction of the C. atrox matrices before application to the C. durissus terrificus matrix, the flow-through fraction after application to the C. durissus terrificus matrix, the affinity purified anti-C. durissus terrificus antibody, and the affinity purified anti-C. atrox antibody from Example 20. All four of the original immunizing venom antigens were coated on Nunc immunoplates and the antigen binding activity of various dilutions of the different antivenom antibody fraction assessed exactly as described in Example 20. In order to compare the antigen-binding activities of different fractions, values were normalized to either the original starting volume of antibody, or to the original starting concentration of C. atrox-reactive antibody. The ELISA results of the relative reactivity of the different preparations at a specific antibody concentration that fell within the linear range of the assay are shown in Table 6. By passing the crude Wyeth antivenom sequentially over the C. atrox antigen matrix followed by the C. durissus terrificus antigen matrix, one recovers in

TABLE 6

Retention of the Spectrum of Reactivity of a Horse Antivenom by Sequential Immunoaffinity Chromatography

| | C. atrox. | C. adamanteus | B. atrox | C. durissus terrificus |
|---|---|---|---|---|
| Crude Wyeth AV | 100 | 100 | 100 | 100 |
| C. atrox flow-through before C. durissus matrix | 8 | 10 | 22 | 55 |
| C. atrox/C. durissus terrificus matrices flow-through | 8 | 8 | 20 | 10 |
| Affinity purified anti-C. durissus terrificus | 1 | <1 | <1 | 38 |
| Affinity purified anti-C. atrox (Ex.20) | 84 | 70 | 66 | 38 |
| Sum of two affinity purified antibodies | 85 | 70 | 66 | 76 | the sum of the two purified antibodies more than 66% of the crude antivenom's initial reactivity with all four venoms. The important function of the second matrix was to purify the vast majority of the C. durissus terrificus-reactive antibody that would not bind to the first (C. atrox) matrix.

The anti-C. atrox-reactive antibody population that bound to the C. atrox matrix was further fractionated by applying 3.2 $A_{280}$ units of affinity purified antibody prepared as described in Example 20 to the same C. durissus terrificus Actigel A antigen matrix described above. Two antibody subpopulations were obtained. The first was the flow-through fraction that did not bind to the C. durissus terrificus matrix. The second was eluted from the column with 4M guanidine-HCl pH 8.0 after washing the matrix with PBS, BBS-Tween and PBS as in Example 13. The eluate was collected, dialyzed against PBS, and measured ($A_{280}$). The results showed that 0.63 of the original $A_{280}$ units applied were bound to and eluted from the antigen matrix, thus 20% of the *C. atrox*-reactive antibody isolated on a *C. atrox* matrix is also reactive with *C. durissus terrificus*. This antibody comprises one polyvalent (with respect to *C. atrox* and *C. durissus terrificus*) antibody subpopulation of the original antivenom.

The unbound flow-through fraction constitutes the *C. atrox*-reactive, *C. durissus terrificus* non-reactive antibody subpopulation of the original antivenom, or the *C. atrox*-specific monovalent subpopulation.

To confirm the venom binding reactivity of the three different antibody subpopulations identified in this example, an ELISA was performed exactly as described above and the *C. atrox*-reactivity and *C. durissus terrificus*-reactivity of the *C. durissus terrificus*-specific monovalent antibody subpopulation, the *C. atrox*-specific monovalent antibody subpopulation, and the *C. atrox*/*C. durissus*-specific polyvalent antibody subpopulation compared as the two antigens. The results are shown in FIGS. 11A, 11B and 11C for the three subpopulations, respectively. The results demonstrate that the monovalent subpopulations are strongly reactive only with their respective single venoms while the polyvalent subpopulation is strongly reactive with both venoms.

EXAMPLE 22

Purification of the broad spectrum of venom-reactive antibodies present in a crude mammalian antivenom in one step using a cocktail matrix.

An alternative to purifying antivenom antibodies on successive antigen matrices was demonstrated. In this example, 2.5 ml. of a *C. atrox*-Actigel A antigen matrix prepared as described in Example 8 and 2.5 ml. of a *C. durissus terrificus* antigen matrix prepared as described in Example 9 were mixed together to form one combination antigen matrix. 0.25 ml of Wyeth antivenom was diluted with 10 mls of PBS and applied to the combination antigen matrix, the flow-through fraction was saved and the matrix was washed with PBS, BBS-Tween, and TBS and specific antibody eluted with Actisep elution medium as described in Example 17. The eluate was collected, dialyzed against PBS, and measured ($A_{280}$). The results showed that approximately 2.2 mg of specific antibody was eluted from the matrix, which corresponds to a specific antibody titer of 8.8 mg. per ml. of Wyeth antivenom. This correlates well with previous determinations of 7.5 mg. of *C. atrox*-and 1.2 mg. of *C. durissus terrificus* reactive antibody (7.5+1.2=8.7 which is very close to 8.8) per ml of Wyeth antivenom (see Examples 19 and 21).

The unbound and eluted fractions were assayed by ELISA as described in Example 20 in order to determine the spectrum of reactivity of the chromatographic fractions before and after purification. To calculate the percent of the initial reactivity on each of the four venoms, values were normalized to either the original starting volume of antivenom, the original concentration of *C-durissus terrificus*-reactive antibody, or the original concentration of *C. atrox*-reactive antibody. The reactivity of different samples at a concentration of antibody that fell within the linear range of the ELISA assay were compared and are shown in Table 7.

These results demonstrate that antibodies reactive with all four venoms can be substantially purified by application to a combination antigen matrix composed of the two most antigenically distinct venoms used for immunization. Importantly, the spectrum of reactivity of the antivenom antibody purified in a single step in this example is comparable to the sum of reactivities of the *C. atrox*- and *C. durissus terrificus* reacting antibodies that were sequentially purified in Example 21.

TABLE 7

Reactivity of Cocktail-Matrix-Purified Antivenom

| | C. atrox | C. adamanteus | B. atrox | C. durissus terrificus |
|---|---|---|---|---|
| Crude Wyeth AV | 100 | 100 | 100 | 100 |
| Combination matrix flow-through | 11 | 16 | 20 | 12 |
| Affinity purified antibody from combination matrix | 73 | 77 | 69 | 71 |
| Sum of affinity purified anti-C. atrox and C. durissus terrificus from Example 21 | 85 | 70 | 66 | 76 |

EXAMPLE 23

Purification of avian antibodies by sequential immunoaffinity chromatography over individual antigen matrices and in one step using a cocktail matrix.

In this example, chicken antibody was eluted from a cocktail antigen matrix and compared with antibody eluted from single-antigen matrices. 8 mg *C. atrox* venom was coupled per ml of ACTIGEL A as in Example 8. 8 mg *C. adamanteus* venom was coupled per ml of ACTIGEL A as in Example 9. Pool 4 PEG-prep (see Example 4) from chicken #354 was used in three separate assays.

Assay 1

2 mls of PEG-purified 127 (containing approximately 3.0 $A_{280}$ units of specific antibody) was loaded on a 2 ml *C. atrox* antigen matrix (approximately 16 mg of total venom protein) at a flow rate of 1 ml per minute. The flow through was carefully collected and the *C. atrox* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate A") immediately with 4M guanidine-HCl (pH 8.0) and the *C. atrox* antigen matrix was washed with PBS.

The flow through was thereafter loaded on the *C. adamanteus* antigen matrix (2 mls; approximately 16 mg of total venom protein) at a flow rate of 1 ml per minute. The *C. adamanteus* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate B") immediately with 4M guanidine-HCl (pH 8.0) and the antigen matrix was washed with PBS. Eluates A and B were measured ($A_{280}$) and found to contain the following amounts of specific antibody:

| Eluate | Protein ($A_{280}$) |
|---|---|
| A | 2.86 |
| B | 0.11 |

Thus, when antibody is passed sequentially over a *C. atrox* antigen matrix and a *C. adamanteus* antigen matrix, the vast majority of venom-specific antibody is pulled out by the *C. atrox* antigen matrix.

Assay 2

2 mls of Pool 4 PEG-prep (approximately 3.0 $A_{280}$ units of specific antibody) was loaded on a 2 ml *C. adamanteus* antigen matrix (approximately 16 mg of total venom protein) at a flow rate of 1 ml per minute. The flow through was carefully collected and the *C. adamanteus* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate C") immediately with 4M guanidine-HCl (pH 8.0) and the *C. adamanteus* antigen matrix was washed with PBS.

The flow through was thereafter carefully loaded on the *C. atrox* antigen matrix (2 mls; approximately 16 mg of total venom protein) at a flow rate of 1 ml per minute. The *C. atrox* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate D") immediately with 4M guanidine-HCl (pH 8.0) and the *C. atrox* antigen matrix was washed with PBS. Eluates C and D were measured ($A_{280}$) and found to contain the following amounts of specific antibody:

| Eluate | Protein ($A_{280}$) |
|---|---|
| C | 1.98 |
| D | 0.92 |

Thus, when antibody is passed sequentially over a *C. adamanteus* antigen matrix and a *C. atrox* antigen matrix, a significant portion of venom-specific antibody is left behind by the *C. adamanteus* antigen matrix.

Assay 3

2 mls of the *C. atrox* antigen-matrix was mixed with 2 mls of the *C. adamanteus* antigen matrix to make a 4 ml cocktail antigen matrix. 2 mls of Pool 4 PEG-prep (approximately 3.0 $A_{280}$ units of specific antibody) was loaded on the cocktail antigen matrix at a flow rate of 1 ml per minute. The flow through ("first flow through") was carefully collected and the cocktail antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate E") immediately with 4M guanidine-HCl (pH 8.0) and the cocktail antigen matrix was washed with PBS.

The first flow through was thereafter loaded on a *C. atrox* antigen matrix (2 mls; approximately 16 mg of total venom protein) at a flow rate of 1 ml per minute. Again, the flow through ("second flow through") was carefully collected. The *C. atrox* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate F") immediately with 4M guanidine-HCl (pH 8.0) and the *C. atrox* antigen matrix was washed with PBS.

The second flow through was thereafter loaded on a *C. adamanteus* antigen matrix (2 mls; approximately 16 mg of total venom protein) at a flow rate of 1 ml per minute. The *C. adamanteus* antigen matrix was washed successively with several bed volumes of PBS, BBS-Tween (0.1 M boric acid, 0.025 M sodium borate, 1 M NaCl, 0.1% (v/v) Tween 20 pH 8.3), and PBS until the effluent was free of protein ($A_{280}$). Bound chicken antibody was eluted ("eluate G") immediately with 4M guanidine-HCl (pH 8.0) and the *C. adamanteus* antigen matrix was washed with PBS.

Eluates E, F and G were measured ($A_{280}$) and found to contain the following amounts of specific antibody:

| Eluate | Protein ($A_{280}$) |
|---|---|
| E | 2.77 |
| F | 0.17 |
| G | 0.06 |

Thus, the cocktail antigen matrix pulls out the vast majority of venom-specific antibody in the chicken antibody preparation.

The results of all three assays demonstrate that the *C. atrox* and *C. adamanteus* venoms are immunologically similar (consistent with the results of Examples 20–22 obtained with a mammalian antivenom). Because of this immunochemical similarity (and the fact that boosting venoms were only *C. atrox* and *C. adamanteus*), it was expected that either antigen matrix alone would be efficient at retaining the spectrum of antibody reactivity of the unpurified avian antivenom. Surprisingly, *C. adamanteus* is not efficient in this respect. For this reason, all further tests of chicken anti-Crotalid antivenom was performed with antibody affinity purified on a *C. atrox* antigen matrix.

EXAMPLE 24

Recyclability of an aldehyde-activated agarose venom antigen matrix.

In this example, the stability and recyclability of an aldehyde-activated venom antigen matrix was demonstrated. *C. atrox* venom was dissolved at 10 mg 1 ml in PBS and coupled to Actigel A (Sterogene) as described in Example 8. 2 ml of crude horse antiserum (lot # M878035) was loaded on this antigen matrix (5 ml column) at 1 ml per minute to begin each purification cycle (one complete cycle is described in Example 15; see FIG. 6). The antigen matrix was subjected to repeated cycles of antivenom application, matrix washing, and specific antibody elution. The amount of antibody purified from was quantitated at four different time points over a 260 day period. The results are shown in Table 8. The mean $A_{280}$ units recovered were 20.4 with approximately 15% variation. The results show that no significant loss of capacity occurred after eleven complete column cycles and 254 days of column life. Thus, the aldehyde-activated venom antigen matrix is stable and recyclable.

TABLE 8

Matrix Recyclability

| Day | # of Previous Cycles | Total $A_{280}$ Units |
|---|---|---|
| 6 | 2 | 23.1 |
| 7 | 4 | 17.4 |
| 62 | 9 | 19.0 |
| 254 | 11 | 22.1 |

EXAMPLE 25

Antigen-binding activity of guanidine-eluted antivenom antibodies from a CNBr-agarose venom antigen matrix.

The quality of venom-specific antibody eluted from an antigen matrix using Resin I was determined by reactivity in an ELISA. 96-well Nunc (VWR Scientific, San Francisco) ImmunoPlates were coated overnight at 4° C. in a humidified chamber with 200 µl/well of C. atrox venom at a concentration of 2 µg/ml. The next day the wells were blocked with PBS containing 0.1% bovine serum albumin (BSA) for 2 hours at room temperature. To perform the ELISA, i) unimmunized whole chicken serum, ii) PEG-purified 355, iii) 355 flow through, and iv) Resin I purified 355 (see Example 13 for description of 355 preparation) were appropriately diluted (PEG-purified 355 and 355 flow through were diluted according to the specific antibody concentration of Resin I purified 355) in PBS (containing 0.1% BSA) and added to the wells in duplicate. The plates were incubated for 2 hours at room temperature. The plates were then washed three times with BBS (0.1 M boric acid, 0.025 M sodium borate, 1 M NaCl, pH 8.3) containing 0.1% Tween 20, twice with PBS containing 0.1% Tween, and twice with just PBS. Alkaline phosphatase-conjugated rabbit anti-chick IgG (Fisher) was diluted 1:500 in PBS containing 0.1% BSA, added to the plates, and incubated 2 hours at room temperature. The plates were washed as before, except Tris-buffered saline, pH 7.2, was substituted for PBS in the last wash, and p-nitrophenyl phosphate (Sigma) was added at 1 mg/ml in 0.05 M $Na_2CO_3$ pH 9.5, 10 mM $MgCl_2$. The plates were then evaluated quantitatively by reading at 410 nm on a Dynatech MR300 Micro ELISA reader approximately 30 minutes after the substrate was added.

Figure 12:
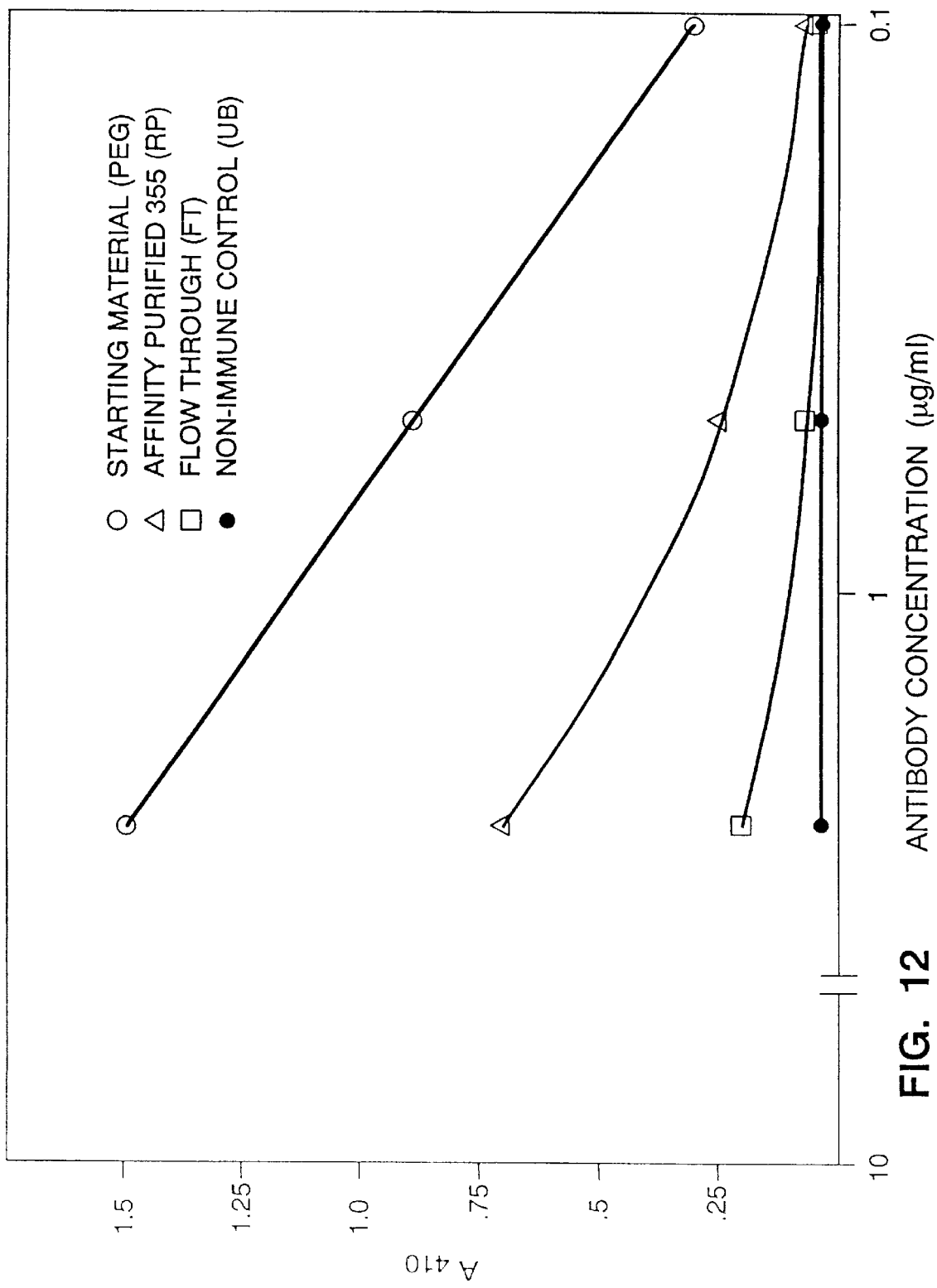
FIG. 12 shows the reactivity by ELISA of avian antivenom purified using one embodiment of the method of the present invention.

The results are shown in FIG. 12. Appropriately, no reactivity is seen with IgY from an unimmunized bird (UB). Similarly, very little reactivity is seen in the 355 flow through (FT). The PEG-purified 355 is highly reactive (PEG). The Resin I purified 355 (RP) is also reactive but is found to be only approximately 50% as reactive as PEG-purified 355 starting material.

EXAMPLE 26

Antigen-binding activity of antivenom antibodies eluted from different venom antigen matrices with different eluents.

The quality of venom-specific antibody eluted from two different aldehyde-activated antigen matrices was determined by reactivity in an ELISA. 96-well plates were coated with C. atrox venom and blocked as in Example 20. To perform the ELISA, i) PEG-purified Pool 4, ii) ultro-purified Pool 4 (see Example 14) and iii) actigel/actisep-purified Pool 4 (see Example 17) were appropriately diluted (PEG-purified Pool 4 was diluted according to the specific antibody concentration of purified Pool 4) in PBS (containing 0.1% BSA) and added to the wells in duplicate. The plates were incubated and washed, and alkaline phosphatase-conjugated rabbit anti-chick IgG was diluted, added to the plates, and incubated; the plates were washed, p-nitrophenyl phosphate was added and the plates were read (see Example 20).

Figure 13:
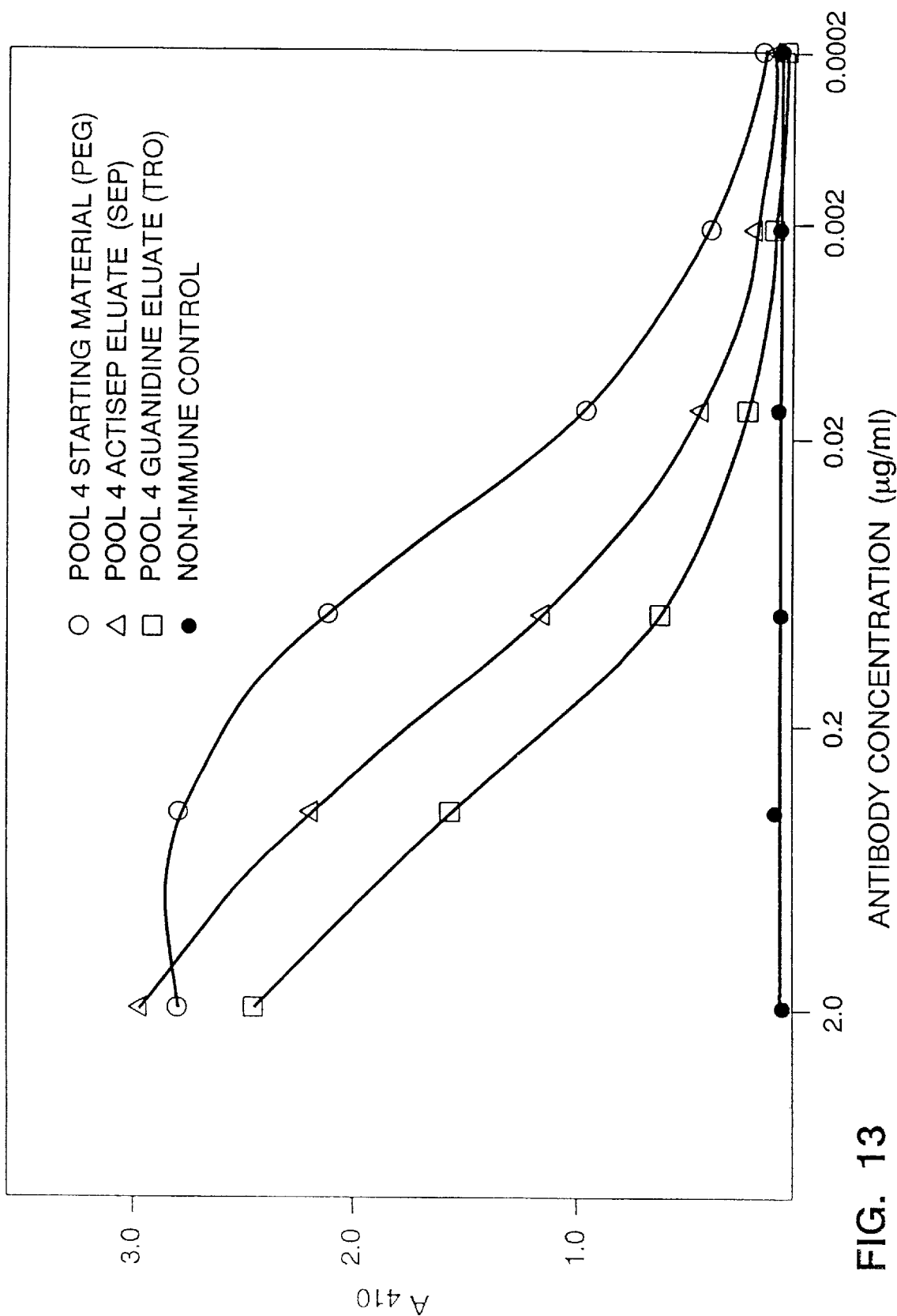
FIG. 13 compares the reactivity by ELISA of two antivenom preparations, purified using two different embodiments of the method of the present invention.

The results are shown in FIG. 13. The PEG-purified Pool 4 is highly reactive (PEG). The actigel/actisep-purified Pool 4 (SEP) is also highly reactive; 75% or more of the reactivity of the starting material is retained. The ultro-purified Pool 4 (TRO) is less reactive; only approximately 50% of the reactivity of the starting material is retained.

EXAMPLE 27

Improved activity of antivenom antibodies when eluted with non-denaturing eluents.

The quality of venom-specific antibody eluted from aldehyde-activated antigen matrices with two different eluents was determined by reactivity in an ELISA. 96-well plates were coated with C. atrox venom and blocked as in Example 20. To perform the ELISA, i) actigel/actisep-purified 355 and ii) actigel/guano-purified 355 (see Example 15) were appropriately diluted in PBS (containing 0.1% BSA) and added to the wells in duplicate. The plates were incubated and washed, and alkaline phosphatase-conjugated rabbit anti-chick IgG was diluted, added to the plates, and incubated; the plates were washed, p-nitrophenyl phosphate was added and the plates were read (see Example 20).

Figure 14:
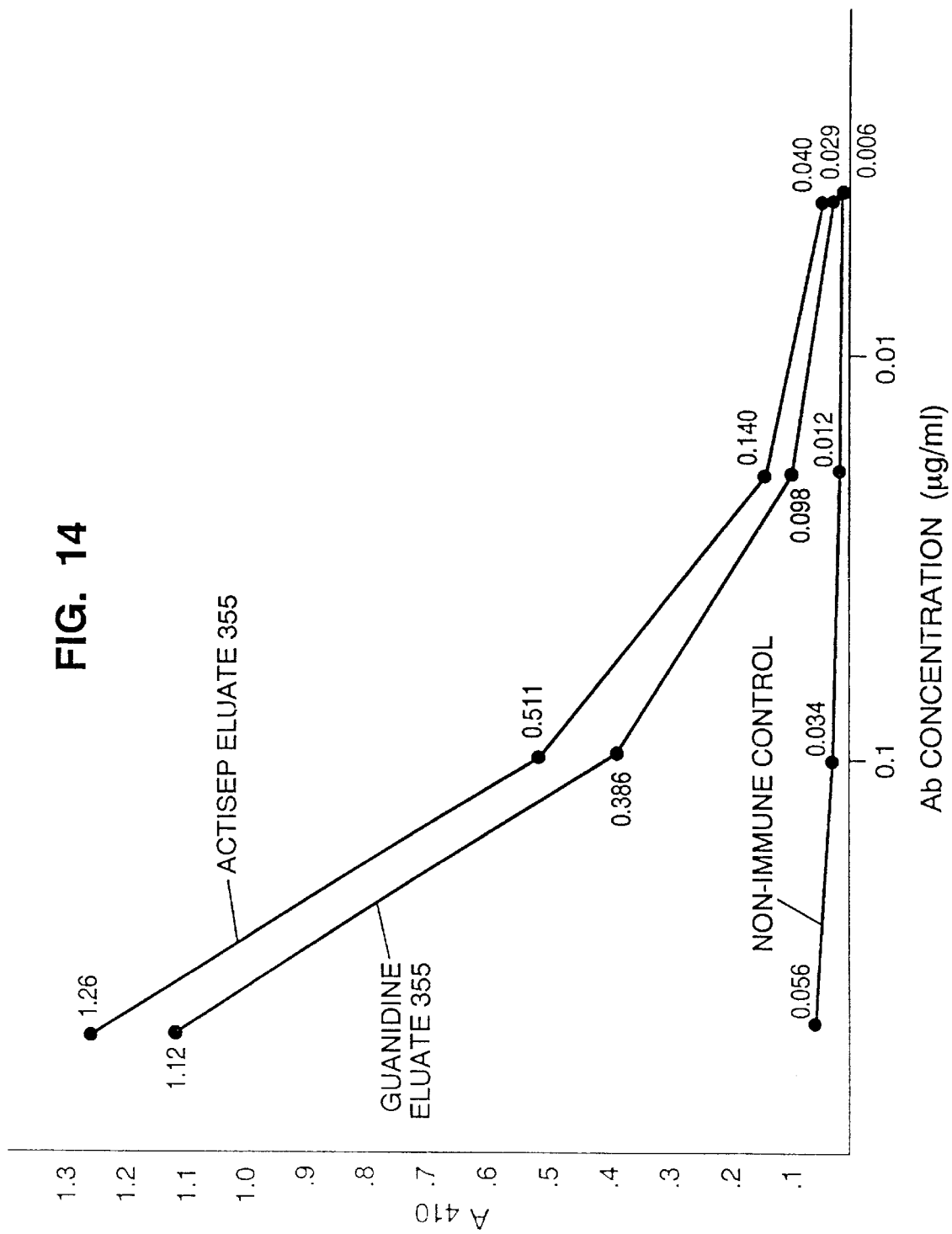
FIG. 14 compares the reactivity by ELISA of two antivenom preparations, purified using two different embodiments of the method of the present invention.

The results are shown in FIG. 14 and indicate that, when identical antibody concentrations of antibody are compared, ACTISEP-eluted antibody is more reactive than guanidine-eluted antibody.

EXAMPLE 28

Reactivity of antivenom antibodies with individual venom components before and after affinity purification.

The nature of the reactivity of affinity-purified antivenom was demonstrated by western blot. 100 µg samples of Crotalus adamanteus, Crotalus atrox, and Agkistrodon piscivorus venom were dissolved in SDS reducing sample buffer and heated at 95° C. for 10 minutes as in Example 1. The samples were then separated on a 10–20% gradient reducing SDS-PAGE. One strip of the gel was stained with Coomassie Blue. The proteins in the remaining portion of the gel were transferred to nitrocellulose, the nitrocellulose was temporarily stained to visualize the lanes, destained, and blocked (see Example 1). The blot was cut into strips and each strip incubated with the appropriate primary antibody. PEG-purified pool 3 of chicken #354 and affinity-purified pool 3 of chicken #354 (see Example 18) were diluted in PBS (containing 1 mg/ml BSA) at a concentration of 2.5 µg/ml of specific antibody and added to the appropriate strip for 2 hours at room temperature. The strips were washed with 2 changes each of large volumes of PBS, BBS-tween and PBS successively (10 min/wash). Goat anti-chicken IgG alkaline phosphatase conjugated secondary antibody (Fisher Biotech) was diluted 1:400 in PBS containing 1 mg/ml BSA and incubated with the blot for 2 hours at room temperature. The blots were washed with 2 changes each of large volumes of PBS and BBS-Tween, followed by 1 change of PBS and 0.1M Tris-HCl, pH 9.5. Blots were developed in freshly prepared alkaline phosphatase substrate buffer: 100 mg/ml Nitro-Blue Tetrazolium (Sigma), 50 mg/ml 5-Bromo-4-Chloro-3-Indolyl Phosphate (Sigma), and 5 mM $MgCl_2$ in 50 mM $Na_2CO_3$ pH 9.5.

Figure 15:
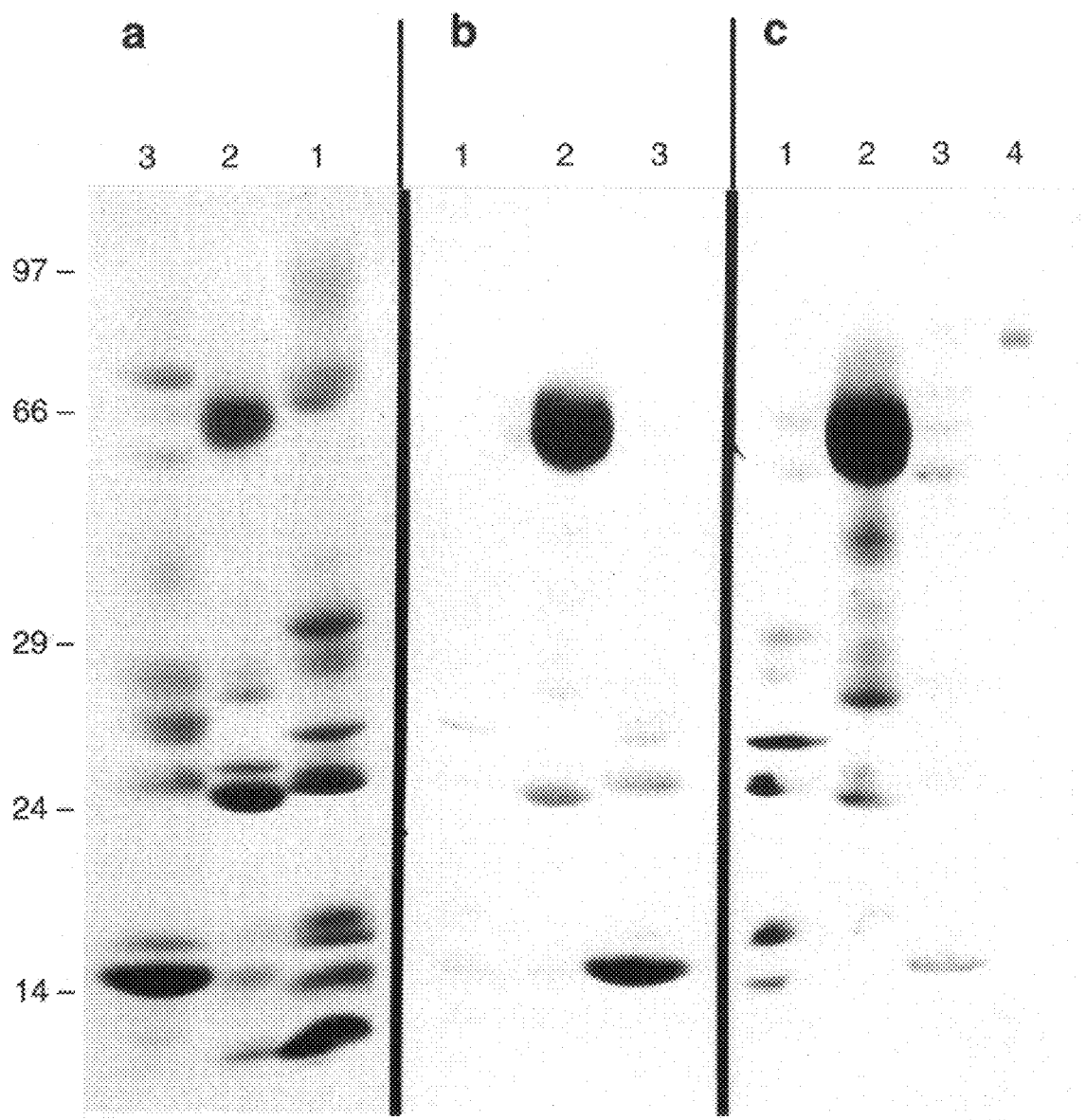
FIG. 15 shows the spectrum of reactivity by Western Blot of antivenoms before and after immunoaffinity purification.

The results are shown in FIG. 15. Lane numbers correspond to the venoms: Crotalus adamanteus was placed in Lane 1; *Crotalus atrox*, was placed in Lane 2; *Agkistrodon piscivorus* was placed in Lane 3. The Coomassie Blue strip (Strip a) show the proteins of the different venoms. Strip b was blotted with PEG-purified pool 3. Strip c was blotted with the affinity-purified pool 3. A comparison of Strips b and c shows that the two purified preps exhibit reactivities against the same individual components of the three venoms, indicating that there has been no significant loss of antibody reactivity against any particular components of the venom.

EXAMPLE 29

Reactivity and crossreactivity of an immunoaffinity purified non-mammalian antivenom with immunizing and non-immunizing venoms.

The crossreactivity of affinity-purified antivenoms was demonstrated by western blot. 100 μg venom samples from 14 different snakes were dissolved in sample buffer, heated and separated on a 10–20% gradient reducing SDS-PAGE. Protein transfer, staining, destaining, and blocking were as in Example 28. The entire blot was incubated for 2 hours at room temperature with anti-*C. atrox* immunoaffinity-purified antibody (Pool #4) that was diluted in PBS (containing 1 mg/ml BSA) to a concentration of 2.5 μg/ml. The blot was washed, alkaline phosphatase-conjugated, goat anti-chicken Ig (Fisher) secondary antibody was added, and the blot was washed again and developed as in Example 28.

Figure 16:
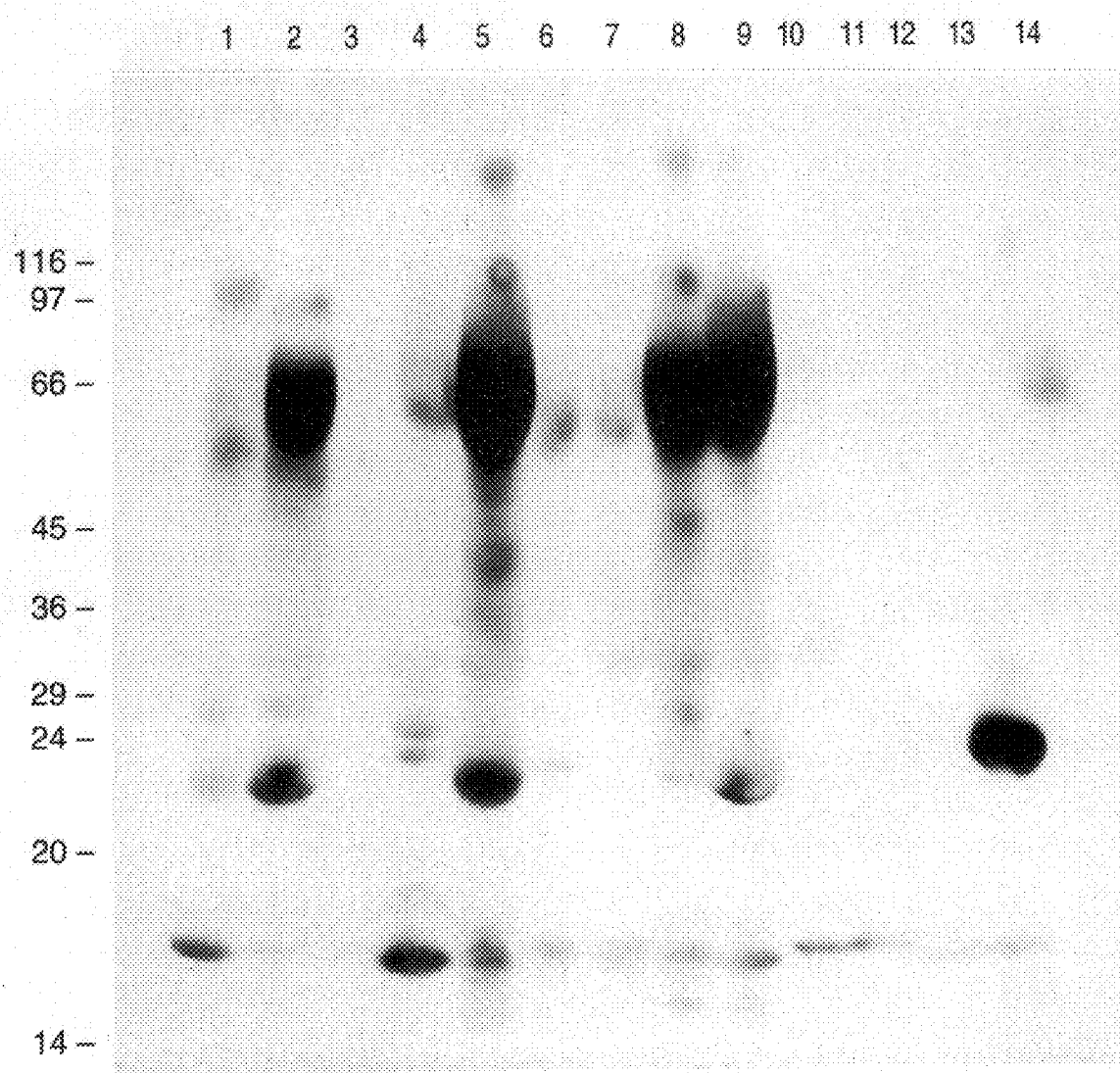
FIG. 16 shows the spectrum of reactivity by Western Blot of immunoaffinity purified antivenoms with immunizing and non-immunizing venoms.

The results are shown in FIG. 16. Lane numbers correspond to the venoms: Lane 1, *A. piscivorus;* lane 2, *A. contortrix;* lane 3, *A. rhodostoma;* lane 4, *B. atrox;* lane 5, *C. atrox;* lane 6, *C. adamanteus;* lane 7, *C. viridis viridis;* lane 8, *C. horridus horridus;* lane 9, *C. ruber;* lane 10, *C. scutulatus;* lane 11, *C. durissus terrificus;* lane 12, *Vipera russelli;* lane 13, *Trimereserus elegans;* lane 14, *Echis carinatus.*

The degree of crossreactivity reflected geographic and evolutionary relationships. The antivenom reacted most strongly against venom from *C. horridus horridus* (central and eastern U.S.), *C. ruber* (Mexico), and *C. viridis viridis* (Central U.S.); no reactivity was observed against venoms from *C. durissus terrificus* (South America), *A. rhodostoma* (Southeast Asia), and *Trimereserus elegans* (Asia). Significantly, the immunoaffinity purified, anti-*C. atrox* antivenom reacted poorly with venom from *C. scutulatus,* an extremely neurotoxic venom from a southwestern United States rattlesnake. Since *C. scutulatus* was not present in the original immunizing cocktail, these results indicate that i) there is practically no anti-*C. atrox* antibody that is crossreactive with *C. scutulatus* venom and ii) there may be very little crossreactive antibody generated with the particular cocktail used for immunization. This underscores the importance of both the cocktail used on the antigen matrix and the cocktail selected for immunization. This also illustrates the utility of the antivenoms of the present invention in selecting appropriate cocktails.

EXAMPLE 30

In vivo neutralization of rattlesnake venom lethality by affinity purified non-mammalian antivenom antibody.

In this example, the ability of antivenom immunoaffinity purified on a *C. atrox* antigen matrix to neutralize the lethal effect of *C. atrox* venom in mice was demonstrated. To first establish the lethal dose of *C. atrox* venom in mice, whole venom was dissolved and diluted in saline (0.85% NaCl) to give different doses of venom per unit of mouse body weight. It was observed that 7 mg of *C. atrox* venom per kg of body weight was usually fatal within 24 hours when injected intraperitoneally.

To determine the venom-neutralizing activity of the affinity purified antivenom antibodies, the Actisep eluted antibody from Pool 3 in Example 18 was concentrated on a Centricon-30 concentration unit (Amicon; Bedford, Mass.) to 4 mg of antibody per ml of PBS. Identical amounts of this antibody and a control non-immune chicken antibody (Cappel) were separately mixed with a fixed amount of *C. atrox* venom in saline, incubated for one hour, and a 110–130 μl dose (the particular dose varied according to individual body weights) of each mixture was injected into 9–10 live mice of between 25–34 grams in weight. The mice were observed for 24 hours and the results of the example are shown in Table 9. Thus, the affinity purified anti-*C. atrox* antibody exhibited complete protection of the experimental mice from the lethal effects of the venom. The statistical significance of the effect of the antivenom antibody treated mice survival frequency was examined by Chisquare analysis and the value for p was determined to be <0.01. This is the first demonstration of in vivo neutralization of a venom by an avian antivenom.

TABLE 9

| | Neutralization of Venom In Vivo | | |
|---|---|---|---|
| Venom Dose (mg/kg) | Antibody Type and Dose (mg/kg) | Number of Mice Alive | Number of Mice Dead |
| 7 mg *C. atrox*/kg | 14 mg non-immune-Chick 1 gG/kg | 1 | 8 |
| 7 mg *C. atrox*/kg | 14 mg affinity purified anti-*C. atrox* 1 gG/kg | 10 | 0 |

EXAMPLE 31

Antivenom to *Notechis scutatus* venom.

*Notechis scutatus,* an Australian elapid, produces a potent neurotoxic venom ($LD_{50}$ approximately 40 μg/kg in mice). R. G. D. Theakston, In: Natural Toxins. Animal, Plant, and Microbial, (J. B. Harris, ed.) Clarendon Press, Oxford 1986, pp. 287–303. In this example, anti-*N. scutatus* antivenom is made according to the following steps: a) venom detoxification, b) primary immunization, c) secondary and further immunizations, d) antivenom collection, and e) antivenom purification.

a) Venom detoxification. *N. scutatus* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.

b) Primary immunization. 1 ml of bentonite suspension containing 1 mg of *N. scutatus* venom is injected subcutaneously into three month old hens at multiple sites on day 0.

c) Secondary and further immunizations. 0.25 mg of *N. scutatus* venom is emulsified in a 4:5 volume ratio of IFA (GIBCO) and injected into multiple subcutaneous sites on days 14, 21, and 42.

d) Antivenom collection. Eggs, beginning on day 28, are extracted using the polyethylene glycol 8000 precipitation method described here in Example 1.

e) Antivenom purification. 5 mg of *N. scutatus* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 32

Antivenom to *Acanthophis antarcticus* venom.

This example describes the production of a specific antivenom for *A. antarcticus*. This Australian elapid produces a potent neurotoxic venom. R. G. D. Theakston, In: Natural Toxins. Animal, Plant, and Microbial, (J. B. Harris, ed.) Clarendon Press, Oxford 1986, pp. 287–303. The example comprises the following steps: a) venom detoxification, b) primary immunization, c) secondary and further immunizations, d) antivenom collection, and e) antivenom purification.

a) Venom detoxification. *A. antarcticus* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.

b) Primary immunization. 1 ml of bentonite suspension containing 1 mg of *A. antarcticus* venom is injected subcutaneously into three month old hens at multiple sites on day 0.

c) Secondary and further immunizations. 0.25 mg of *A. antarcticus* venom is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of *A. antarcticus* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 33

Antivenom to *Oxyuranus scutellatus* venom.

In this example, production of antivenom to *Oxyuranus scutellatus* snake venom is described. This Australian elapid produces a potent neurotoxic venom ($LD_{50}$ approximately 150 µg/kg in mice). R. G. D. Theakston, In: Natural Toxins. Animal, Plant, and Microbial, (J. B. Harris, ed.) Clarendon Press, Oxford 1986, pp. 287–303. The example comprises the following steps: a) venom detoxification, primary immunization, c) secondary and further immunizations, d) antivenom collection, and e) antivenom purification.

a) Venom detoxification. *O. scutellatus* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.

b) Primary immunization. 1 ml of bentonite suspension containing 1 mg of *O. scutellatus* venom is injected subcutaneously into three month old hens at multiple sites on day 0.

c) Secondary and further immunizations. 0.25 mg of *O. scutellatus* venom is emulsified in a 4:5 volume ratio of incomplete freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of *O. scutellatus* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 34

Antivenom to *Pseudonaia textilis* venom.

In this example, the production of antivenom to *Pseudonaja textilis* snake venom is described. This Australian elapid produces a potent neurotoxic venom. R. G. D. Theakston, In: Natural Toxins. Animal, Plant, and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.

a) Venom detoxification. *P. textilis* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.

b) Primary immunization. 1 ml of bentonite suspension containing 1 mg of *P. textilis* venom is injected subcutaneously into three month old hens at multiple sites on day 0.

c) Secondary and further immunizations. 0.25 mg of *P. textilis* venom is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of *P. textilis* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 35

Antivenom to *Pseudechis australis* venom.

In this example the production of antivenom to *Pseudechis australis* snake venom is described. This Australian elapid produces a potent neurotoxic venom. R. G. D. Theakston, In: Natural Toxins. Animal, Plant, and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.

a) Venom detoxification. *P. australis* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.

b) Primary immunization. 1 ml of bentonite suspension containing 1 mg of *P. australis* venom is injected subcutaneously into three month old hens a multiple sites on day 0.

c) Secondary and further immunizations. 0.25 mg of *P. australis* venom is emulsified in a 4:5 volume ratio of incomplete Freund's adjuvant (GIBCO, Grand Island, N.Y.) and injected into multiple subcutaneous sites on days 14, 21, and 42.
d) Antivenom collection is from eggs beginning on day 28 and shall be extracted using the polyethylene glycol 8000 precipitation method described in Example 1.
e) Antivenom purification. 5 mg of *P. australis* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 36

Antivenom to *Enhydrina schistosa* venom.

In this example, the production of antivenom to *Enhydrina schistosa* snake venom is described. This Australian elapid produces a potent neurotoxic venom. R. G. D. Theakston, In: Natural Toxins. Animal, Plant, and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.
a) Venom detoxification. *E. schistosa* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.
b) Primary immunization. 1 ml of bentonite suspension containing 1 mg of *E. schistosa* venom is injected subcutaneously into three month old hens at multiple sites on day 0.
c) Secondary and further immunizations. 0.25 mg of *E. schistosa* venom is emulsified in a 4:5 volume ratio of incomplete Freund's adjuvant (GIBCO, Grand Island, N.Y.) and injected into multiple subcutaneous sites on days 14, 21, and 42.
d) Antivenom collection is from eggs beginning on day 28 and shall be extracted using the polyethylene glycol 8000 precipitation method described in Example 1.
e) Antivenom purification. 5 mg of *E. schistosa* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 37

Antivenom to *Ophiophagus hannah* venom.

In this example, the production of antivenom to *Ophiophagus hannah* snake venom is described. This elapid produces a potent neurotoxic venom ($LD_{50}$ approximately 2.5 mg/kg in mice). R. G. D. Theakston, In: Natural Toxins. Animal, Plant, and Microbial, (J. B. Harris, ed.) Clarendon Press, Oxford 1986, pp. 287–303. The example involves the following steps:
a) venom detoxification, b) primary immunization, c) secondary and further immunizations, d) antivenom collection, and e) antivenom purification.

a) Venom detoxification. *O. hannah* venom (Sigma Chemical Co. St. Louis, Mo.; Miami Serpentarium, Salt Lake City, Utah) is completely absorbed to bentonite by adding 1 mg of venom per ml of a 2% suspension of sterile bentonite particles.
b) Primary immunization. 1 ml of bentonite suspension containing 1 mg of *O. hannah* venom is injected subcutaneously into three month old hens at multiple sites on day 0.
c) Secondary and further immunizations. 0.25 mg of *O. hannah* venom is emulsified in a 4:5 volume ratio of incomplete Freund's adjuvant (GIBCO, Grand Island, N.Y.) and injected into multiple subcutaneous sites on days 14, 21, and 42.
d) Antivenom collection is from eggs beginning on day 28 and shall be extracted using the polyethylene glycol 8000 precipitation method described in Example 1.
e) Antivenom purification. 5 mg of *O. hannah* venom is coupled per ml of aldehyde-activated agarose matrix using the cyanoborohydride reduction method as described in Example 8. 5 ml of PEG purified crude antivenom is applied per ml of column matrix and the unbound protein is washed away, the specific antibody sequentially eluted and the eluent removed, and the column regenerated as described in Example 17.

EXAMPLE 38

Antivenom to *Vipera* venoms.

In this example, the production of antivenom to *Vipera ammodytes, Vipera aspis,* and *Vipera berus* snake venoms is described. These vipers produce venoms with strong hemorrhagic and neurotoxic properties ($LD_{50}$ approximately 350–750 μg/kg in mice). R. G. D. Theakston, In: Natural Toxins. Animal, Plant. and Microbial, (J. B. Harris, ed.) Clarendon Press, Oxford 1986, pp. 287–303. A. Ohsaka. In: *Snake Venoms,* (C. Y. Lee, ed.) Handbook of Experimental Pharmacology, Vol. 52, Springer Verlag, Berlin 1979, pp. 480–546. The example involves the following steps: a) venom detoxification, primary immunization, c) secondary and further immunizations, d) antivenom collection, and e) antivenom purification.
a) Venom detoxification. *V. ammodytes, V. berus* (Sigma Chemical Co., St. Louis, Mo.; Miami Serpentarium, Salt Lake City, Utah) and *V. aspis* venom (Miami Serpentarium, Salt Lake City, Utah) is completely absorbed to bentonite by adding 1 mg of each venom per ml of a 2% suspension of sterile bentonite particles.
b) Primary immunization. 1 ml of bentonites suspension containing 1 mg of each venom (*V. ammodytes, V. aspis, V. berus*) is injected subcutaneously into three month old laying hens at multiple sites on day 0.
c) Secondary and further immunizations. 0.25 mg of each venom is emulsified in a 4:5 volume ratio of incomplete Freund's adjuvant and injected into multiple subcutaneous sites on days 14, 21, and 42.
d) Antivenom collection is from eggs beginning on day 28 and shall be extracted from egg yolks using the polyethylene glycol 8000 precipitation method described herein (Example 1(c), pg. 22).
e) Antivenom purification. 5 mg of each venom is coupled individually per ml of aldehyde-activated agarose matrix using the cyanoborohydride reduction method as described in Example 8. The coupled matrices are blended into one column and 5 ml of PEG-purified crude antivenom is applied per ml of column matrix. The unbound protein is washed away, the specific antibody sequentially eluted, the eluent removed, and the column regenerated as described in Example 17.

EXAMPLE 39

Antivenom to Vipera and Cerastes venoms.

In this example, the production of antivenom to *Vipera xanthina palestinae, Vipera lebetina, Cerastes cerastes, Cerastes vipera* snake venoms is described. These vipers produce venoms with strong hemorrhagic and neurotoxic properties ($LD_{50}$ approximately 0.5–2.0 mg/kg in mice). R. G. D. Theakston, In: Natural Toxins. Animal, Plant. and Microbial, (J. B. Harris, ed.) Clarendon Press, Oxford 1986, pp. 287–303. A. Ohsaka. In: *Snake Venoms*, (C. Y. Lee, ed.) Handbook of Experimental Pharmacology, Vol. 52, Springer Verlag, Berlin 1979, pp. 480–546. The example involves the following steps: venom detoxification, b) primary immunization, c) secondary and further immunizations, d) antivenom collection, and e) antivenom purification.

a) Venom detoxification. *V. x. palestinae, V. lebetina, C. cerastes* (Sigma Chemical Co., St. Louis, Mo.; Miami Serpentarium, Salt Lake City, Utah) and *C. vipera* venom (Miami Serpentarium, Salt Lake City, Utah) is completely absorbed to bentonite by adding 1 mg of each venom per ml of a 2% suspension of sterile bentonite particles.

b) Primary immunization. 1 ml of bentonite suspension containing 1 mg of each venom (*V. x. palestinae. V. lebetina, C. cerastes,* and *C. vipera*) is injected subcutaneously into three month old laying hens at multiple sites on day 0.

c) Secondary and further immunizations. 0.25 mg of each venom is emulsified in a 4:5 volume ratio of incomplete Freund's adjuvant and injected into multiple subcutaneous sites on days 14, 21, and 42.

d) Antivenom collection is from eggs beginning on day 28 and shall be extracted from egg yolks using the polyethylene glycol 8000 precipitation method described in Example 1.

e) Antivenom purification. 5 mg of each venom is coupled individually per ml of aldehyde-activated agarose matrix using the cyanoborohydride reduction method as described in Example 8. The coupled matrices are blended into one column and 5 ml of PEG-purified crude antivenom is applied per ml of column matrix. The unbound protein is washed away, the specific antibody sequentially eluted, the eluent removed, and the column regenerated as described in Example 17.

EXAMPLE 40

Antivenom to Bitis, Vipera, and Echis venoms.

In this example, the production of antivenom to *Bitis arietans, Bitis gabonica, Vipera russelli,* and *Echis carinatus* snake venom is described. These vipers produce venoms with strong hemorrhagic and neurotoxic properties ($LD_{50}$ approximately 0.25–2.0 mg/kg in mice). R. G. D. Theakston, In: Natural Toxins. Animal, Plant. and Microbial, (J. B. Harris, ed.) Clarendon Press, Oxford 1986, pp. 287–303. A. Ohsaka. In: *Snake Venoms*. (C. Y. Lee, ed.) Handbook of Experimental Pharmacology, Vol. 52, Springer Verlag, Berlin 1979, pp. 480–546. The example involves the following steps:

a) Venom detoxification, *B. arietans, B. gabonica, V. russelli, E. carinatus* (Sigma Co., St. Louis, Mo.; Miami Serpentarium, Salt Lake City, Utah) is completely absorbed to bentonite by adding 1 mg of each venom per ml of a 2% suspension of sterile bentonite particles.

b) Primary immunization. 1 ml of bentonite suspension containing one ml of each venom (*B. arietans, B. gabonica, V. russelli,* and *E. carinatus* is injected subcutaneously into three month old laying hens at multiple sites on day 0.

c) Secondary and further immunizations. 0.25 mg of each venom is emulsified in a 4:5 volume ratio of incomplete Freund's adjuvant and injected into multiple subcutaneous sites on days 14, 21, and 42.

d) Antivenom collection is from eggs beginning on day 28 and shall be extracted from egg yolks using the polyethylene glycol 8000 precipitation method described in Example 1.

e) Antivenom purification. 5 mg of each venom is coupled individually per ml of aldehyde-activated agarose matrix using the cyanoborohydride reduction method as described in Example 8. The coupled matrices are blended into one column and 5 ml of PEG-purified crude antivenom is applied per ml of column matrix. The unbound protein is washed away, the specific antibody sequentially eluted, the eluent removed, and the column regenerated as described in Example 17.

EXAMPLE 41

Antivenom to Trimeresurus and Agkistrodon venoms.

In this example, the production of antivenom to *Trimeresurus flavoviridis* and *Agkistrodon halys* snake venom is described. These two snakes inflict the most bites in Japan and their venoms contain strong hemorrhagic toxins ($LD_{50}$ approximately 0.8–2.7 mg/kg in mice). R. G. D. Theakston, In: Natural Toxins. Animal, Plant, and Microbial, (J. B. Harris, ed.) Clarendon Press, Oxford 1986, pp. 287–303. A. Ohsaka. In: *Snake Venoms*, (C.-Y. Lee, ed.) Handbook of Experimental Pharmacology, Vol. 52, Springer Verlag, Berlin 1979, pp. 480–546. The example involves the following steps: a) venom detoxification, biprimary immunization, c) secondary and further immunizations, d) antivenom collection, and e) antivenom purification.

a) Venom detoxification. *T. flavoviridis* and *A. halys* venoms (Sigma Chemical Co., St. Louis, Mo.; Miami Serpentarium, Salt Lake City, Utah) is completely absorbed to bentonite by adding 1 mg of each venom per ml of a 2% suspension of sterile bentonite particles.

b) Primary immunization. 1 ml of bentonite suspension containing 1 mg of both *T. flavoviridis* and *A. halys* venoms is injected subcutaneously into three month old laying hens at multiple sites on day 0.

c) Secondary and further immunizations. 0.25 mg of both *T. flavoviridis* and *A. halys* venoms is emulsified in a 4:5 volume ratio of incomplete Freund's adjuvant (GIBCO, Grand Island, N.Y.) and injected into multiple subcutaneous sites on days 14, 21, and 42.

d) Antivenom is from eggs beginning on day 28 and shall be extracted from egg yolks using the polyethylene glycol 8000 precipitation method described in Example 1.

e) Antivenom purification. 5 mg of each venom is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 42

Antivenom to Naja and Hemachatus venoms.

In this example, the production of antivenom to *Naja naja, Nala n. haje, Naja n. kaouthia, Naja n. oxiana, Naja n. sputatrix, Naja n. atra, Naja nivea, Naja nigrocollis,* and *Hemachatus hemachatus* snake venom is described. These snakes produce potent neurotoxic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification b) primary immunization, c) secondary and further immunizations, d) antivenom collection, and e) antivenom purification.

a) Venom detoxification. *N. naja, N. n. haje, N. n. kaouthia, N. n. oxiana, N. n. sputatrix, N. n. atra, N. nivea, N. nigrocollis*, and *H. hemachatus* venoms (Sigma Chemical Co., St. Louis, Mo.; Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each venom (*N. naja, N. n. haje, N. n. kaouthia, N. n. oxiana, N. n. sputatrix, N. n. atra, N. nivea, N. nigrocollis,* and *Hemachatus hemachatus*) is injected subcutaneously into three month old hens at multiple sites on day 0.

c) Secondary and further immunizations. 0.25 mg of each venom above is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom *N. naja, N. n. haje, N. n. kaouthia, N. n. oxiana, N. n. sputatrix, N. n. atra, N. nivea, N. nigrocollis,* and *Hemachatus hemachatus* is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 43

Antivenom to Dendroaspis venoms.

In this example, the production of antivenom to *Dendroaspis angusticeps, Dendroaspis jamesonii, Dendroaspis polylepis, Dendroaspis viridis* snake venoms is described. These snakes produce potent neurotoxic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) anti-venom purification.

a) Venom detoxification. *O. angusticeps, O. lamesonii, O. polylepis* and *O. viridis* venoms (Sigma Chemical Co., St. Louis, Mo.; Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each *O. angusticens, O. jamesonii, O. polylepis,* and *O. viridis* venom is injected subcutaneously into three month old hens a multiple sites on day 0.

c) Secondary and further immunizations. 0.25 mg of each venom above is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom (*O. angusticeps, O. jamesonii, O. polylepis* and *O. viridis*) is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 44

Antivenom to Bungarus venoms.

In this example, the production of antivenom to *Bungarus caerulus, Bungarus fasciatus, Bungarus multicinctus* snake venoms is described. These snakes produce potent neurotoxic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.

a) Venom detoxification. *B. caerulus. B. fasciatus,* and *B. multicinctus* venoms (Sigma Chemical Co., St. Louis, Mo.; Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each *B. caerulus, B. fasciatus* and *B. multicinctus* venom is injected subcutaneously into three month old hens at multiple sites on day 0.

c) Secondary and further immunizations. 0.25 mg of each venom above is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom (*B. caerulus, B. fasciatus,* and *B. multicinctus*) is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 45

Antivenom to Agkistrodon venoms.

In this example, the production of antivenom to *Agkistrodon rhodostoma* and *Agkistrodon acutus* snake venoms is described. These snakes produce potent hemorrhagic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification, b)primary immunization, c) secondary and further immunizations, d) antivenom collection, and e) antivenom purification.

a) Venom detoxification. *A. rhodostoma* and *A. acutus* venoms (Sigma Chemical Co., St. Louis, Mo.; Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each *A. rhodostoma* and *A. acutus* venom is injected subcutaneously into three month old hens at multiple sites on day 0.

c) Secondary and further immunizations. 0.25 mg of each venom above is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom (*A. rhodostoma* and *A. acutus*) is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 46

Antivenom to Bothrops and Lachesis venoms.

In this example, the production of antivenom to *Bothrops atrox, Bothrops jararaca, Bothrops jararacussu, Bothrops alternatus,* and *Lachesis muta* snake venoms is described. These snakes produce potent hemorrhagic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.

a) Venom detoxification. *B. atrox, B. jararaca, B. jararacussu, B. alternatus* and *L. muta* venoms (Sigma Chemical Co., St. Louis, Mo.; Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each *B. atrox, B. jararaca, B. jararacussu, B. alternatus* and *L. muta* venom is injected subcutaneously into>three month old hens at multiple sites on day 0.

c) Secondary and further immunizations. 0.25 mg of each venom above is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom *B. atrox, B. jararaca, B. jararacussu, B. alternatus* and *L. muta* is coupled individually per ml of aldehyde-activated agarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 47

Antivenom to Micrurus venoms.

In this example, the production of antivenom to *Micrurus corralus, Micrurus fulvius, Micrurus frontalis,* and *Micrurus nigrocinctus* snake venoms is described. These snakes produce potent neurotoxic venoms. R. G. D. Theakston, In: Natural Toxins. Animal, Plant and Microbial, (J. B. Harris, ed.) Clarendon Press, Oxford 1986, pp. 287–303. The example involves the following steps: a) venom detoxification, b) primary immunization, c) secondary and further immunizations, d) antivenom collection, and e) antivenom purification.

a) Venom detoxification. *M. fulvius* and *M. frontalis* venoms (Sigma Chemical Co., St. Louis, Mo.; Miami Serpentarium, Salt Lake City, Utah) and *M. corralus* and *M. nigrocinctus* venoms (Miami Serpentarium, Salt Lake City, Utah) are completely absorbed to bentonite by adding 1 mg of each venom per ml of a 2% suspension of sterile bentonite particles.

b) Primary immunization. 1 mg of bentonite suspension containing 1 mg of each *M. corralus, M. fulvius, M. frontalis* and *M. nigrocinctus* venom is injected subcutaneously into>three month old hens at multiple sites on day 0.

c) Secondary and further immunizations. 0.25 mg of each venom above is emulsified in a 4:5 volume ratio of incomplete Freund adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of each venom *M. corralus, M. fulvius, M. frontalis* and *M. nigrocinctus* are coupled individually per ml of aldehyde-activatedagarose matrix using the cyanoborohydride reduction method as described in Example 8. The coupled matrices are blended into a single column and 5 ml of PEG-purified crude antivenom is applied per ml of column matrix. The unbound protein is washed away, the specific antibody sequentially eluted, the eluent removed, and the column regenerated as described in Example 17.

EXAMPLE 48

Production of an avian antivenom to a scorpion venom.

In this example, birds were immunized with venom from a scorpion *Leiurus guinguestriatus hebraeus* (L.gg.). The example involved a)adsorbent/antigen mixture preparation, b) immunization, and c) antibody collection.

a) Adjuvant/antigen mixture preparation: L.gg. venom (Sigma) was dissolved in distilled water and the soluble fractions used as an antigen in several mixtures with a 2% sterile bentonite suspension. The first bentonite/antigen mixture consisted of 500 µg of the water soluble extract of L.gg. venom, the second bentonite antigen mixture also consisted of 500 µg of the water soluble extract of L.gg. venom, the third mixture was 400 µg of the water soluble extract of L.gg. venom. A fourth mixture was of either 0.33 mg or 0.66 mg of L.gg. venom mixed with incomplete Freund's adjuvant in a relationship of 5:4 (adjuvant: antigen by volume) and emulsified to a firm consistency by passage through an antigen mixer made from two 18 gauge stainless steel hypodermic needles that had been brazed together.

b) Immunization: Two, (previously unimmunized) one-year old white leghorn hens (numbered for reference as #338 and #347) were immunized on day zero. Both #338 and #347 received the first adjuvant/antigen mixture on day 0, the second adjuvant/antigen mixtures on day 14, and the third adjuvant/antigen mixtures on day 23. On day 57, bird #338 received 0.33 mg of venom in IFA while bird #347 received 0.66 mg of venom in IFA.

c) Antibody collection: Antibody was collected from the eggs as described in Example 1.

EXAMPLE 49

Covalent attachment of the water soluble toxic fraction of a scorpion venom to an aldehyde-activated agarose matrix.

In this example, the coupling efficiency of the aldehyde activated Actigel A (Sterogene) resin (resin III) with L.gg. venom as the ligand was demonstrated. L.gg. venom was diluted in PBS (pH 7.2) at a concentration of 2.5 mg/ml. Resin III was washed with three volumes of PBS and added (in equal volume) to the venom solution. Thereafter, 1/10 volume of 1M sodium cyanoborohydride (Aldrich) was added and the mixture (antigen matrix) was agitated for four hours at 4° C. The antigen matrix was washed on a glass funnel with PBS. The filtrate was collected and coupling efficiency was calculated as the percent of the starting protein that was covalently attached to the matrix as described in Example 6. The results showed that the resin III coupling efficiency for L.gg. venom was 88%. The antigen matrix was stored in PBS containing 0.02% sodium azide at 4° C.

EXAMPLE 50

Immunoaffinity purification of non-mammalian anti-scorpion antivenom from an aldehyde-activated scorpion venom antigen matrix.

In this example, the purification of scorpion venom-specific antibodies on a venom antigen matrix was demonstrated. 2.5 mg L.gg. venom was coupled per ml of Actigel A as described in Example 49 above. Two large pools of anti-scorpion antibody were purified separately on the antigen matrix. The first pool was 50 ml of PEG-purified antibody (8–10 mg protein/ml; from eggs collected on day 23–32 from birds #338 and #347), the second pool was 170 ml of PEG-purified antibody (8–10 mg protein/ml; from eggs collected on days 60–68 from birds #338 and #347). Each pool was loaded on a 2 ml scorpion venom antigen matrix at a flow rate of 1 ml per minute, and washed successively with several bed volumes of PBS, BBS-Tween, and TBS until the effluent was free of protein ($A_{280}$). Anti-venom antibody was eluted with ACTISEP Elution Medium (Sterogene) with a residence time of 2 hours, and the matrix was washed with TBS. The eluate was collected and measured ($A_{280}$) after complete dialysis against TBS and PBS. The results showed that 0.45 mg of antibody was purified from the first pool and 0.68 mg of antibody from the second pool.

EXAMPLE 51

Neutralization of scorpion venom lethality by an affinity purified non-mammalian antivenom.

In this example, the ability of affinity purified chicken anti-*L. guinguestriatus hebraeus* venom antibodies to neutralize the lethal effects of the L.gg. venom in vivo was demonstrated. To first establish the lethal dose of L.gg. venom in mice, water soluble extracts of venom were diluted in saline (0.85% NaCl) to give different doses per unit of mouse body weight. It was observed that 0.6 mg of venom per kg of body weight was usually fatal within 24 hours when injected intravenously.

To determine the venom neutralizing activity of the antivenom antibodies purified as described in Example 50, the two pools of purified antibody were combined and concentrated on a Centricon-30 concentration unit (Amicon; Bedford, Mass.) to 2.1 mg of antibody per ml of PBS. Identical amounts of this antibody and a control non-immune chicken antibody (Cappel) were separately mixed with a fixed amount of the water soluble extract of L.egg. venom in saline, incubated for 1 hours and 100–200 µl of each mixture injected intravenously into 6–8 mice. The mice were observed for 24 hours and the results of this example are shown in Table 10.

The statistical significance of the effect of the antivenom antibody treated mice survival frequency was examined by Chi-square analysis and the value for p was determined to be <0.05.

TABLE 10

Neutralization of Scorpion venom In Vivo

| Venon Dose (mg/kg) | Antibody type and dose (mg/kg) | Number of mice alive | Number of mice dead |
|---|---|---|---|
| 0.63 mg *L. quinquestriatus*/kg | 3.1 mg non-immune chicken IgG/kg | 1 | 5 |
| 0.63 mg *L. quinoquestriatus* 1 kg | 3.1 mg effinity purified anti-*L. quinquestriatus*/kg IgG | 7 | 1 |

EXAMPLE 52

Antivenom to Centruroides venoms.

In this example, the production of antivenom to *Centruroides suffusus*, *Centruroides noxius*, and *Centruroides sculpturatus* scorpion venoms is described. These North American scorpions produce venoms containing several distinct neurotoxins. M. F. Martin et al., 1987. *J. Biol. Chem.* 262: 4452–4459. We contemplate the production of an antivenom specific for these three scorpion venoms that comprises the following steps: a) venom detoxification, b) primary immunization, c) secondary and further immunizations, d) antivenom collection, and e) antivenom purification.

a) Venom detoxification. *C. sculpturatus* (available commercially through Sigma Chemical Co., St. Louis, Mo.), *C. suffusus* and *C. noxious* venoms (obtained by milking as described by M. F. Martin et al., 1987. *J. Biol. Chem.* 262: 4452–4459) water soluble fractions are completely absorbed by adding 0.5 mg of each venom per ml of a 2% suspension of sterile bentonite particles.

b) Primary immunization. 1 ml of a bentonite suspension containing 0.5 mg of each venom is injected subcutaneously into three month old hens at multiple sites on day 0.

c) Secondary and further immunizations. 0.25 mg of each venom is emulsified in a 4:5 volume ratio of incomplete Freund's adjuvant (GIBCO, Grand Island, N.Y.) and injected into multiple subcutaneous sites on days 14, 21, and 42.

d) Antivenom collection is from eggs beginning on day 28 and shall be extracted using the polyethylene glycol 8000 precipitation method described in Example 1.

e) Antivenom purification. 5 mg of the water soluble fractions of *C. sculpturatus*, *C. noxius*, and *C. suffusus* venoms are coupled individually per ml of aldehyde-activated agarose matrix using the cyanoborohydride method described in Example 8 and blended into a single column. 5 ml of PEG-purified crude antivenom is applied per ml of column matrix and the unbound protein is washed away, the specific antibody sequentially eluted, the eluent removed, and the column regenerated as described in Example 17.

EXAMPLE 53

Antivenom to Tityus venom.

In this example, the production of antivenom to *Tityus serrulatus* scorpion venoms is described. Largely a problem in South and Central America the genus Tityus includes many dangerous species including *T. serrulatus* ($LD_{50}$ approximately 1.5 mg/kg in mice). G. G. Habermehl, Venomous Animals and Their Toxins. Springer Verlag 1981, Berlin. The example involves the following steps: a) venom detoxification, b) primary immunization, c) secondary and further immunizations, d) antivenom collection, and e) antivenom purification.

a) Venom detoxification. *T. serrulatus* venom (available commercially through Sigma Chemical Co., St. Louis, Mo.), water soluble fraction is completely absorbed by adding 0.5 mg of each venom per ml of a 2% suspension of sterile bentonite particles.
b) Primary immunization. 1 ml of a bentonite suspension containing 0.5 mg of each venom is injected subcutaneously into three month old hens at multiple sites on day 0.
c) Secondary and further immunizations. 0.25 mg of each venom is emulsified in a 4:5 volume ratio of incomplete Freund's adjuvant (GIBCO, Grand Island, N.Y.) and injected into multiple subcutaneous sites on days 14, 21, and 42.
d) Antivenom collection is from eggs beginning on day 28 and shall be extracted using the polyethylene glycol 8000 precipitation method described in Example 1.
e) Antivenom purification. 5 mg of the water soluble fraction of *T. serrulatus* venom is coupled per ml of aldehyde-activated agarose matrix using the cyanoborohydride method described in Example 8. 5 ml of PEG-purified crude antivenom is applied per ml of column matrix and the unbound protein is washed away, the specific antibody sequentially eluted, the eluent removed, and the column regenerated as described in Example 17.

EXAMPLE 54

Antivenom to Androctonus, Buthotus, and Buthus venoms.

In this example, the production of antivenom to *Androctonus australis, Buthotus judaicus,* and *Buthus tamalus* scorpion venoms is described. These Old World scorpions produce potent neurotoxic venoms ($LD_{50}$ 6–8 mg/kg in mice). G. G. Habermehl, Venomous Animals and Their Toxins, Springer Verlag, 1981, Berlin. The example involves the following steps: a) venom detoxification, b) primary immunization, c) secondary and further immunizations, d) antivenom collection, and e) antivenom purification.

a) Venom detoxification. *A. australis, B. judaicus,* and *B. tamalus* (available commercially through Sigma Chemical Co., St. Louis, Mo.), water soluble venom fractions are completely absorbed by adding 0.5 mg of each venom per ml of a 2% suspension of sterile bentonite particles.
b) Primary immunization. 1 ml of a bentonite suspension containing 0.5 mg of each venom is injected subcutaneously into>three month old hens at multiple sites on day 0.
c) Secondary and further immunizations. 0.25 mg of each venom is emulsified in a 4:5 volume ratio of incomplete Freund's adjuvant (GIBCO, Grand Island, N.Y.) and injected into multiple subcutaneous sites on days 14, 21, and 42.
d) Antivenom collection is from eggs beginning on day 28 and shall be extracted using the polyethylene glycol 8000 precipitation method described in Example 1.
e) Antivenom purification. 5 mg of the water soluble fractions of *A. australis, B. judaicus,* and *B. tamalus* venoms are coupled individually per ml of aldehyde-activated agarose matrix using the cyanoborohydride method described in Example 8 and blended into a single column. 5 ml of PEG-purified crude antivenom is applied per ml of column matrix and the unbound protein is washed away, the specific antibody sequentially eluted, the eluent removed, and the column regenerated as described in Example 17.

EXAMPLE 55

Antivenom to *Chironex fleckeri* venom.

In this example, the production of antivenom to the jelly fish *Chironex fleckeri* venom is described. The box jelly fish or sea wasp, *Chironex fleckeri* is found in the tropical waters off Northern Australia. The nematocysts in its tentacles contains a potent venom that can be lethal to humans ($LD_{50}$ in mice of crude venom approximately 0.4 mg/kg) C. E. Olson et al., 1984. Toxicon 22: 733–742. The example involves the following steps: a) venom detoxification, b) primary immunization, c) secondary and further immunizations, d) antivenom collection, and e) antivenom purification.

a) Venom detoxification. *C. fleckeri* venom is obtained from captured specimens as described by R. Endean, 1987. Toxicon 25: 483–492. 0.5 mg of the crude venom will completely absorbed to each ml of a 2% suspension of sterile bentonite particles.
b) Primary immunization. 1 ml of a bentonite suspension containing 0.5 mg of each venom is injected subcutaneously into>three month old hens at multiple sites on day 0.
c) Secondary and further immunizations. 0.25 mg of *C. fleckeri* venom is emulsified in a 4:5 volume ratio of incomplete Freund's adjuvant (GIBCO, Grand Island, N.Y.) and injected subcutaneously at multiple sites on days 14, 21, and 42.
d) Antivenom collection is from eggs beginning on day 28 and shall be extracted using the polyethylene glycol 8000 precipitation method described in Example 1.
e) Antivenom purification. 5 mg of *C. fleckeri* venom is covalently coupled per ml of aldehyde-activated agarose matrix using the cyanoborohydride reduction method described in Example 8. 5 ml of PEG-purified crude anti-*C. fleckeri* antivenom is applied per ml of column matrix and the unbound protein is washed away, the specific antibody sequentially eluted, the eluent removed, and the column regenerated as described in Example 17.

EXAMPLE 56

Antivenom to black widow spider venom.

In this example, the production of antivenom to black widow spider *Latrodectus mantans* and *Latrodectus hesperus* venom is described. The black widows (*L. mactans* and *L. hesperus*) are an especially venomous group of spiders ($LD_{50}$ approximately 1 mg/kg in mice) G. G. Habermehl. Venomous Animals and Their Toxins, Springer Verlag, Berlin 1981. The example involves the following steps: a) venom detoxification, b) primary immunization, c) secondary and further immunization, d) antivenom collection, and e) antivenom purification.

a) Venom detoxification. *Latrodectus hesperus* venom and *L. m. mactans* venom saca (Sigma Chemical Co., St. Louis, Mo.) are completely absorbed to bentonite by adding 0–5 mg *L. hesperus* venom and the water soluble fraction from 20 mg of *L. mactans* venom sacs per ml of a 2% suspension of sterile bentonite particles.

b) Primary immunization. 1 ml of a bentonite suspension containing 0.5 mg of each venom is injected subcutaneously into>three month old laying hens at multiple sites on day 0.

c) Secondary and further immunizations. 0.25 mg of *L. hesperus* venom and the water soluble fraction from 10 mg of *L. mactans* venom sacs are emulsified in a 4:5 volume ratio of incomplete Freund's adjuvant (GIBCO, Grand Island, N.Y.) and injected subcutaneoulsy at multiple sites on days 14, 21, and 42.

d) Antivenom collection is from eggs beginning on day 28 and shall be extracted using the polyethylene glycol 8000 precipitation method described in Example 1.

e) Antivenom purification. 5 mg. of *L. hesperus* venom and all of the water soluble fraction from 100 mg. of *L. mactans* venom sacs are coupled individually per ml of aldehyde-activated agarose matrix using the cyanoborohydride method described in Example 8 and pooled into a single column. 5 ml of PEG-purified crude antivenom is applied per ml of column matrix and the unbound protein is washed away, the specific antibody sequentially eluted, the eluent removed, and the column regenerated as described in Example 17.

EXAMPLE 57

Antivenom to recluse spider venom.

In this example, the production of antivenom to *Loxosceles reclusa* spider venom is described. The Loxosceles genus is an important group of venomous group of spiders in many parts of the world. G. G. Habermehl, Venomous Animals and Their Toxins, Ch. 3, p. 22, Springer Verlag, Berlin 1981. The example involves the following steps: a) venom detoxification, b) primary immunization, c) secondary and further immunizations, d) antivenom collection, and e) antivenom purification.

a) Venom detoxification. *L. reclusa* venom (Sigma Chemical Co., St. Louis, Mo.) is completely absorbed to bentonite by adding 0.5 mg *L. reclusa* venom per ml of a 2% suspension of sterile bentonite particles.

b) Primary immunization. 1 ml of a bentonite suspension containing 0.5 mg of venom is injected subcutaneously into three month old laying hens at multiple sites on day 0.

c) Secondary and further immunizations. 0.25 mg of *L. reclusa* venom is emulsified in a 4:5 volume ratio of incomplete Freund's adjuvant (GIBCO, Grand Island, N.Y.) and injected subcutaneous at multiple sites on days 14, 21, and 42.

d) Antivenom collection is from eggs beginning on day 28 and shall be extracted using the polyethylene glycol 8000 precipitation method described in Example 1.

e) Antivenom purification. 5 mg of *L. reclusa* venom is coupled per ml of aldehyde-activated agarose matrix using the cyanoborohydride method described in Example 8. 5 ml of PEG-purified crude antivenom is applied per ml of column matrix and the unbound protein is washed away, the specific antibody sequentially eluted, the eluent removed, and the column regenerated as described in Example 17.

EXAMPLE 58

Assessment of Antivenom Avidity by Immunodiffusion

In this example, antivenoms to snake venoms are assessed for avidity by Ouchterlony immunodiffusion gels. E. A. Kabat, Structural Concepts in Immunology and Immunochemistry (Holt, Rinehart and Winston, N.Y. 1968). A double diffusion assay is performed using the antivenoms described in Example 17. A 1% agarose solution in phosphate buffered saline (0.15 M NaCl) is poured into a standard 60 mm petri dish (VWR Scientific, San Francisco, Calif.). After the gel hardens, a center well and six surrounding wells are punched out and the agarose plug removed. 10 $\mu$l of a 100 $\mu$g/ml solution of antivenom is placed in the center well. 10 $\mu$l of 100 $\mu$g/ml solutions of *C. atrox* and *C. adamanteus* venoms are placed separately in two of the surrounding wells. The petri dish is placed at 4° C. overnight and then inspected for precipitin lines.

The inspection of the petri dish revealed the presence of precipitin lines (data not shown). This indicates that the antivenom is a high avidity antivenom.

EXAMPLE 59

In vivo administration of avian antivenom.

In this example, we contemplate the treatment of humans by in vivo administration of affinity purified antivenom following crotalid envenomation. Treatment comprises the following steps: a) identification of the venomous snake that has bitten the victim; b) determination of the severity of the envenomation; and c) intravenous administration of purified antivenom.

a) Identification of the venomous snake: The snake species is identified as a Crotalid on the basis of morphological criteria (triangular head shape, rattles, scale patterns, etc.). In view of the venomous nature of the offending species, the bite could involve envenomation.

b) Severity of the envenomation: clinical signs of envenomation include but are not limited to the presence of fang marks, local swelling, pain, and necrosis at the bite site and systemic symptoms with partial paralysis, weakness, dizziness, nausea, and hemorrhage. The severity of the envenomation is classified on the basis of the extent of systemic symptoms with minimal envenomation reflected by symptoms restricted to the bite area, moderate envenomation involving tissue damage beyond the bite area, and severe envenomation characterized by tissue destruction extending beyond the bite area and strong systemic symptoms.

c) Intravenous administration of purified antivenom: Antivenom purified as described in Example 17 and equilibrated with phosphate buffered saline is sterilized by filtration through a 0.22 $\mu$m filter (Nalgene; VWR, San Francisco, Calif.), thimerosal (Sigma) added to 0.005% as a preservative, and stored in liquid form at 4° C. This sterile antivenom solution is administered in the following dosages: 250 mg for minimal envenomation; 1000 mg for moderate envenomation; and 2500 mg for severe Crotalid bites. The appropriate amount of antivenom is added to 500 ml of normal saline for adult victims, and to 100 ml of normal saline for children and administered intravenously using an intravenous drip line.

CONCLUSION

From the above, it is evident that the compositions and methods of the present invention allow for A) immunoaffinity purification of antivenom that provides i) maximum attachment of the antigen (e.g. venom) to the resin (i.e. high attachment efficiency), ii) efficient isolation of antigen-specific immunoglobulin that is essentially free of non-antigen-specific protein (i.e. the purity and quantity of antibody obtained is optimized), iii) recovery of the antibody in an active state (i.e. the quality of reactivity is largely preserved), iv) quantitative elution of bound antibody, v) no significant retained antibody to progressively decrease antigen matrix capacity after successive cycles of use (i.e. the antigen matrix is recyclable), vi) reduced burden of foreign protein in the purified antivenom, vii) retention in the purified antivenom of the spectrum of reactivity of the unpurified antivenom, and viii) production of purified antivenom for treatment with reduced side effects; B) epitope determinations that provide i) means of identifying the monovalent and polyvalent antibody subpopulations of an existing antivenom, ii) means of designing cost-effective immunization cocktains for new antivenom formulas, and iii) means of designing cost-effective antigen matrices for purifying new or existing antivenoms.

With respect to retention in the purified antivenom of the spectrum of reactivity of the unpurified antivenom, the handful of previous studies using whole venom describe using only single venom antigen matrices. Single venom antigen matrices are not capable of binding and purifying the spectrum of antivenom antibodies present in the polyvalent commercial antivenom investigated. Thus, purification in the manner described by these researchers necessarily resulted in antivenom with a more limited reactivity than the unpurified antivenom.

In a preferred embodiment, the compositions and methods of the present invention allow for A) production of venom-neutralizing antivenoms in birds which provides i) means for detoxifying venoms while preserving their inmunogenicity, ii) means for raising large quantities of antivenom antibodies while utilizing relatively small amounts of costly immunogens (i.e. the dose per unit body weight is high, but the total dose is small), iii) means for obtaining antivenom antibodies without risking injury to the animal (i.e. bleeding is not required), iv) simple means for obtaining whole yolk antivenom immunoglobulin that is of greater purity than existing horse serum antivenom ammonium sulfate fractions, and v) ant venom preparations without side-effects involving the host complement system.

There are several factors underlying the success of the present invention at obtaining the first venom-neutralizing antivenoms from birds. Among the contributing factors are: i) the preparation of antigens which are detoxified but immunogenic (earlier attempts at raising antivenoms to snake venom in birds were unsuccessful and involved glutaraldehyde-modified venom which, based upon the results herein described, was in all likelihood a poor immunogen), ii) the use of high doses of antigen per unit body weight (the earlier, unsuccessful attempts at producing antivenoms to snake venom in birds may have utilized insufficient doses of antigen to generate a broad high titer response to venom components), iii) purification of venom-reactive immunoglobulin (the earlier, unsuccessful attempts at raising antivenom to snake venom in birds utilized whole yolk immunoglobulin which did not contain a high percentage of venom-reactive immunoglobulin, and iv) generation of high avidity antivenom (the earlier, unsuccessful attempts at raising antivenom to snake venom in birds yielded antivenom that was unreactive at 0.15 M NaCl).

I claim:
1. A method of treatment, comprising:
   a) providing
      a purified chicken antivenom in an aqueous solution in therapeutic amount that is intravenously injectable, wherein said antivenom is obtained from a host immunized with whole venom that is not glutaraldehyde pretreated and wherein said antivenom comprises yolk immunoglobulin of which greater than fifty percent is venom-reactive; and;
   b) intravenously injecting said chicken antivenom into at least one envenomed mammalian subject.
2. The method of claim 1 wherein said avian antivenom reacts with venom selected from the group consisting of Chordata, Arthropoda and Coelenterata venoms.
3. The method of claim 1 wherein said avian antivenom reacts with venom selected from the group consisting of snake venoms, spider venoms, scorpion venoms or jelly fish venoms.
4. The method of claim 1 wherein said avian antivenom reacts with venom selected from the group consisting of *Crotalus scutulatus, Notechis scutatus, Acanthophis antarcticus, Oxyuranus scutellatus, Pseudonaja textilis, Pseudechis australis, Enhydrina schistosa, Ophiophagus hannah, Vipera ammodytes, Vipera aspis, Vipera berus, Vipera xanthina palestinae, Vipera lebetina, Cerastes cerastes, Cerastes vipera, Bitis arietans, Bitis gabonica, Vipera russelli, Echis carinatus, Trimeresurus flavoviridis, Agkistrodon halys, A. piscivorus, A. contortrix, Naja naja, Naja n. haje, Naja n. kaouthia, Naja n. oxiana, Naja n. sputatrix, Naja n. atra, Naja nivea, Naja nigrocollis, Hemachatus hemachatus, Dendroaspis angusticeps, Dendroaspis jamesonii, Dendroaspis polylepis, Dendroaspis viridis, Bungarus caerulus, Bungarus fasciatus, Bungarus multicinctus, Agkistrodon rhodostoma, Agkistrodon acutus, Bothrops atrox, Bothrops jararaca, Bothrops jararacussu, Bothrops alternatus, Lachesis muta, Micrurus corralus, Micrurus fulvius, Micrurus frontalis, Micrurus niagrocinctus, Leiurus guinguestriatus, Tityus serrulatus, Centruroides suffusus, Centruroides noxius, Centruroides sculpturatus, Androctonus australis, Buthotus judaicus, Buthus tamalus, Latrodectus mactans, Latrodectus hesperus, Loxosceles reclusa,* and *Chironex fleckeri.*
5. The method of claim 1 wherein said avian antivenom reacts with *C. atrox, B. atrox, C. adamanteus* and *C. durissus terrificus* venoms.
6. A method of treatment, comprising:
   a) providing
      i) a purified polyvalent antivenom in an aqueous solution in therapeutic amount that is intravenously injectable, comprising immunoglobulin of which greater than fifty percent is venom-reactive, said purified antivenom being derived from a first polyvalen antivenom having two or more monovalent subpopulations, and being purified such that greater than fifty percent of said monvalent subpopulations are recovered by weight,
      ii) at least one envenomed mammalian subject; and
   b) intravenously injecting said polyvalent antivenom into said subject.
7. The method of claim 6 wherein said polyvalent antivenom is horse antivenom.
8. The method of claim 6 wherein said polyvalent antivenom reacts with venom selected from the group consisting of Chordata, Arthronoda and Coelenterata venoms.
9. The method of claim 6 wherein said polyvalent antivenon reacts with venom selected from the group consisting of snake venoms, spider venoms, scorpion venoms or jelly fish venoms.

10. The method of claim 6 wherein said polyvalent antivenom reacts with venom selected from the group consisting of *Crotalus scutulatus, Notechis scutatus, Acanthophis antarcticus, Oxyuranus scutellatus, Pseudonala textilis, Pseudechis australis, Enhydrina schistosa, Ophiophagus hannah, Vipera ammodytes, Vipera aspis, Vipera berus, Vipera xanthina palestinae, Vipera lebetina, Cerastes cerastes, Cerastes vipera, Bitis arietans, Bitis gabonica, Vipera russelli, Echis carinatus, Trimeresurus flavoviridis, Agkistrodon halys, A. piscivorus, A. contortrix, Naja naja, Naja n. haje, Naja n. kaouthia, Naja n. oxiana, Naja n. sputatrix, Naja n. atra, Naja nivea, Naja nigrocollis, Hemachatus hemachatus, Dendroaspis angusticeps, Dendroaspis jamesonii, Dendroaspis polylepis, Dendroaspis viridis, Bungarus caerulus, Bungarus fasciatus, Bungarus multicinctus, Agkistrodon rhodostoma, Agkistrodon acutus, Bothrops atrox, Bothrops jararaca, Bothrops jararacussu, Bothrops alternatus, Lachesis muta, Micrurus corralus, Micrurus fulvius, Micrurus frontalis, Micrurus niagrocinctus, Leiurus guinguestriatus, Tityus serrulatus, Centruroides suffusus, Centruroides noxius, Centruroides sculpturatus, Androctonus australis, Buthotus judaicus, Buthus tamalus, Latrodectus mactans, Latrodectus hesperus, Loxosceles reclusa,* and *Chironex fleckeri* venoms.

11. The method of claim 6 wherein said polyvalent antivenom reacts with *C. atrox, B. atrox, C. adamanteus* and *C. durissus* terrificus venoms.

12. A method of treatment, comprising:
  a) providing:
    i) an affinity purified antivenom capable of neutralizing both *C. atrox* and *C. durissus terrificus* venoms, and comprising immunoglobulin of which greater than fifty percent is venom-reactive, and
    ii) at least one envenomed mammalian subject,
  b) intravenously injecting said antivenom into said subject.

* * * * *